(12) United States Patent
Böhringer et al.

(10) Patent No.: US 6,218,379 B1
(45) Date of Patent: *Apr. 17, 2001

(54) TRICYCLIC CARBACEPHEMS

(75) Inventors: Markus Böhringer, Möhlin (CH);
Philippe Pflieger, Folgensburg (FR)

(73) Assignee: Hoffmann-la Roche Inc., Nutley, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/857,280

(22) Filed: May 16, 1997

(30) Foreign Application Priority Data

May 24, 1996 (EP) .................................................. 96108309

(51) Int. Cl.[7] ...................... C07D 463/16; C07D 463/18; A61K 31/437; A61D 31/04
(52) U.S. Cl. ...................................... 514/210.03; 540/205
(58) Field of Search ............................ 540/205; 514/210, 514/210.03

(56) References Cited

U.S. PATENT DOCUMENTS

| 5,494,666 | 2/1996 | Böhringer et al. | 514/210 |
| 5,510,343 | 4/1996 | Charnas et al. | 514/210 |

FOREIGN PATENT DOCUMENTS

| 508 234 | 10/1992 | (EP) . |
| 0548 186 B1 | 6/1993 | (EP) . |
| 671 401 | 9/1995 | (EP) . |
| WO 92/04353 | 3/1992 | (WO) . |

OTHER PUBLICATIONS

Hackh's Chemical Dictionary, 3rd edition, p. 853.*
Beilstein Registry 5626344 Printout.*

"Protective Groups in Organic Synthesis", Chapter 5, pp. 152–192 (1981).

* cited by examiner

*Primary Examiner*—Mark L Berch
(74) *Attorney, Agent, or Firm*—George W. Johnston; Patricia S. Rocha-Tramaloni; Eileen M. Ebel

(57) ABSTRACT

The present invention is concerned with compounds of formula

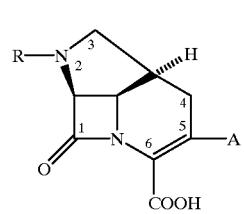

I where A is a group of formula (b1) or (b2)

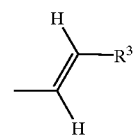

(b1)

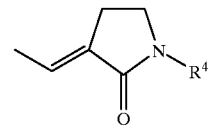

(b2)

where $R^3$ is unsubstituted aryl or aryl substituted by one or two substituents defined herein, and R is as defined herein, together with the pharmaceutically compatible, readily hydrolyzable esters and salts of these compounds. These compounds have valuable antibacterial properties.

124 Claims, No Drawings

TRICYCLIC CARBACEPHEMS

The present invention is concerned with compounds of formula I

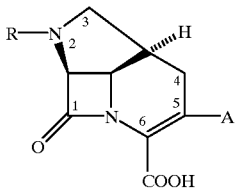

I wherein

R is hydrogen, unsubstituted lower (cyclo)alkyl or lower (cyclo)alkyl substituted by carboxy, lower alkoxycarbonyl, carbamoyl, lower alkylcarbamoyl, phenylcarbamoyl or hydroxyphenylcarbamoyl; lower alkenylmethyl; lower alkenylmethoxycarbonyl; formyl; unsubstituted lower (cyclo)alkanoyl or lower (cyclo)alkanoyl substituted by halogen, cyano, carbamoyl-lower alkoxy, carbamoyl-lower alkylthio, or carbamoyl-lower alkylamino; unsubstituted lower (cyclo)alkylsulphonyl; or lower (cyclo)alkylsulphonyl substituted by halogen, cyano, carbamoyl-lower alkoxy, carbamoyl-lower alkylthio or carbamoyl-lower alkylamino; unsubstituted carbamoyl or carbamoyl substituted by lower (cyclo)alkyl, lower alkoxycarbonyl-lower alkyl, benzyloxycarbonyl-lower alkyl, carboxy-lower alkyl, hydroxyphenyl or carbamoylphenyl; or a ring structure of the formula

 (a1)

or

 (a2)

Q is a 5- or 6-membered ring optionally containing nitrogen, sulphur and/or oxygen and which is optionally substituted by lower alkyl, lower alkoxy, lower alkylthio, hydroxy, carbamoyl, carbamoyl methyl, carbamolyamino, hydroxy phenyl-carbamoyl, sulphamoyl, lower alkanoyloxy, sulphonyloxy, halogen, amino, methylamino, dimethylamino, chloroacetylamino, and pyridin-1-yl-acetylamino;

X is a direct bond or a group —CH$_2$—, —CH$_2$CH$_2$—, —CH=CH—, —NH—, —NHCH$_2$—, —CH$_2$NH—, —CH(NH$_2$)—, —CH$_2$CH$_2$NH—, —C(=NOCH$_3$)—, —OCH$_2$— or —SCH$_2$—; and A is a group of formula (b1) or (b2)

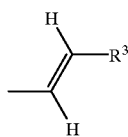 (b1)

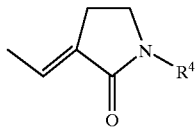 (b2)

wherein

R$^3$ is unsubstituted aryl or aryl substituted by one or two substituents selected from halogen, hydroxy, cyano, nitro, lower alkyl, lower alkoxy, aralkyl, —CONR$^5$R$^6$, —CH$_2$—CONR$^5$R$^6$, —N(R$^6$)COOR$^7$, R$^6$CO—, R$^6$OCO— or R$^6$COO— in which R$^5$ is hydrogen, lower alkyl or lower cycloalkyl; R$^6$ is hydrogen or lower alkyl; and R$^7$ is hydrogen, lower alkyl, lower alkenyl or a carboxylic acid protecting group; an unsubstituted heterocyclyl; a heterocyclyl substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, lower alkenyl substituted phenyl, —CONR$^5$R$^6$, —CH$_2$—CONR$^5$R$^6$, —N(R$^6$)COOR$^7$, R$^6$CO—, R$^6$OCO— or R$^6$COO— in which R$^5$ is hydrogen, lower alkyl or lower cycloalkyl; R$^6$is hydrogen or lower alkyl; and R$^7$ is hydrogen, lower alkyl, lower alkenyl or a carboxylic acid protecting group; a heterocyclyl having a phenyl ring fused thereto, the heterocyclyl thereof being unsubstituted or substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, or lower alkenyl substituted phenyl; and R$^4$ is, hydrogen, hydroxy, lower (cyclo)alkyl, lower alkoxy, lower (cyclo)alkenyl, lower alkynyl, aralkyl, aryl, aryloxy, aralkoyloxy, heterocyclyl or heterocyclylalkyl, with each of lower (cyclo)alkyl, lower alkoxy, lower (cyclo)alkenyl, aralkyl, aryl, aryloxy, aralkoyloxy or heterocyclyl being unsubstituted or substituted by carboxy, amino, nitro, cyano, lower alkyl, benzyl, lower alkoxy, hydroxy, halogen, —CONR$^5$R$^6$, —CH$_2$—CONR$^5$R$^6$, —N(R$^6$)COOR$^7$, R$^6$CO—, R$^6$OCO— or R$^6$COO— in which R$^5$ is hydrogen, lower alkyl or lower cycloalkyl; R$^6$ is hydrogen or lower alkyl; and R$^7$ is hydrogen, lower alkyl, lower alkenyl or a carboxylic acid protecting group;

and pharmaceutically compatible, readily hydrolyzable esters and salts of these compounds.

European Patent Application EP-A-0 671 401 describes β-lactams which have β-lactamase inhibiting and, in part, also antibacterial properties. The compounds in accordance with the invention differ from these known compounds by the substituent A.

It has surprisingly been found that compounds in accordance with the invention have, in addition to their β-lactamase inhibiting properties, an improved spectrum of activity against gram-positive and gram-negative microorganisms and also against β-lactamase producing strains.

These compounds are useful in the control of β-lactamase forming pathogens in combination with β-lactam antibiotics such as the penicillins, cephalosporins, penems and carbapenems. They also have an antibacterial activity themselves and can accordingly also be used alone against bacterial pathogens.

Objects of the present invention are β-lactams of formula I above and pharmaceutically compatible salts thereof, the manufacture of these compounds, medicaments containing a compound of formula I or pharmaceutically compatible salt thereof as well as the use of compounds of formula I and of pharmaceutically compatible salts thereof for the production of medicaments for the control or prevention of infectious diseases, especially those which are caused by β-lactamase forming microorganisms.

The terms in brackets set forth in the definition of formula I, e.g. "lower (cyclo)alkyl", "lower (cyclo)alkanoyl", "lower (cyclo)alkyl-sulphonyl" are to be understood as being optional, and accordingly "lower alkyl", "lower alkanoyl" and "lower alkylsulphonyl" as well as "lower cycloalkyl", "lower cycloalkanoyl" and "lower cycloalkylsulphonyl" are intended.

The term "lower alkyl", taken alone or in combinations, such as "lower alkoxy", "lower alkylamino", "lower alkylcarbamoyl", "lower alkoxy carbonyl", "lower alkanoyl" (="lower alkylcarbonyl"), "lower alkylsulphonyl", "lower alkylthio" and the like, is straight-chain or branched saturated hydrocarbon residues with 7, preferably 4, carbon atoms, such as methyl, ethyl, n-propyl, isopropyl, n-butyl, isobutyl, sec-butyl, t-butyl and the like.

"Lower cycloalkyl", taken alone or in corresponding combinations, is cyclic hydrocarbon residues with 3–6 hydrocarbon atoms, i.e. cyclopropyl, cyclobutyl, cyclopentyl or cyclohexyl.

The term "lower alkenyl", taken alone or in combinations, such as "lower alkenylmethyl" and "lower alkenylmethoxycarbonyl" embraces unsaturated hydrocarbon residues with up to 7, preferably up to 4, carbon atoms, containing a double bond, such as vinyl, allyl and the like.

The term "lower alkynyl" embraces unsaturated hydrocarbon residues with up to 7, preferably up to 4, carbon atoms containing a triple bond, such as ethynyl, propargyl and the like.

"Halogen" is fluorine, chlorine, bromine or iodine, especially fluorine.

The "5- or 6-membered ring optionally containing nitrogen, sulphur and/or oxygen" set forth under R (residue Q) are e.g. phenyl, saturated heterocycles such as pyrrolidinyl, piperidinyl, piperazinyl, morpholinyl, thiomorpholinyl, tetrahydrothienyl and tetrahydrofuryl, and aromatic heterocycles such as 2-furyl, 3-furyl, thiazolyl, thiadiazolyl, oxadiazolyl, 2-thienyl, 3-thienyl, 2-pyrrolyl, 3-pyrrolyl, 1-pyridinio, 2-pyridyl, 3-pyridyl, 4-pyridyl, oxazolyl, isoxazolyl, imidazolyl, pyrazolyl, triazolyl, tetrazolyl, pyrazinyl, pyridazinyl and pyrimidinyl. The 5- or 6-membered ring optionally containing nitrogen sulfur and/or oxygen can also be substituted, e.g. by lower alkyl, lower alkoxy, lower alkylthio, hydroxy, carbamoyl, carbamoylmethyl, carbamoylamino, hydroxy phenyl carbamoyl, sulphamoyl, lower alkanoyloxy, sulphonyloxy, halogen, amino, methylamino, dimethylamino, chloroacetylamino and pyridin-1-yl-acetylamino as well as those additional substituents found on the heterocyclic ring as discussed below. Additional substituents include unsubstituted aryl or aryl substituted by one or two substituents selected from halogen, hydroxy, cyano, nitro, lower alkyl, lower alkoxy, aralkyl, —CONR$^5$R$^6$, —CH$_2$—CONR$^5$R$^6$, —N(R$^6$)COOR$^7$, R$^6$CO—, R$^6$OCO— or R$^6$COO— in which R5 signifies hydrogen, lower alkyl or lower cycloalkyl; R$^6$ signifies hydrogen or lower alkyl; and R$^7$ signifies hydrogen, lower alkyl, lower alkenyl or a carboxylic acid protecting group. N-Heterocycles can also be substituted by oxo. Examples of such substituted rings are 4-tolyl, 4-sulphamoyl-phenyl, 4-hydroxyphenyl, 4-carbamoylphenyl, 3,4-dihydroxyphenyl, 3-methyl-(2-furyl), 1-methyl-1H-tetrazol-5-yl, 4-anisyl, 3,4,5-trimethoxyphenyl, 4-chlorophenyl, 4-fluoro-(2-pyridyl), 2-amino-4-thiazolyl, 5-methyl-1,3,4-thiadiazol-2-yl, p-amino-phenyl, p-(chloroacetylamino)-phenyl, 3,4-disulphonyloxy-phenyl, 3,4-diacetoxyphenyl, 2-oxo-pyrrolidinyl-3-yl, 2-oxo-tetrahydrothien-3-yl, 3-methoxy-isoxazol-5-yl, 1,1-dioxo-tetrahydrothien-3-yl, 3-hydroxy-isoxazol-5-yl, 5-amino-1,3,4-thiadiazol-2-yl, 5-(pyridin-1-yl-acetylamino)-1,3,4-thiadiazol-2-yl and 1-methyl-pyridin-4-yl. The 5- or 6-membered ring optionally containing nitrogen, sulfur and/or oxygen can also be optionally fused to another ring, for example, especially a phenyl ring, such as e.g. indolyl, 1H-benzotriazol-2-yl, 2-oxo-2H-1-benzopyran-7-yl or 2-oxo-4-(trifluoromethyl)-2H-1-benzopyran-7-yl, a saturated 5- or 6-membered carbocyclic ring, such as e.g. in 2,3-cyclopenteno-4-pyridyl and 2,3-cyclohexeno-4-pyridyl, or a 5- or 6-membered heterocycle, such as e.g. benzimidazol-5-yl, 1H-benzotriazol-4-yl or 2-carbamoyl-5-methyl-[1,2,4]triazolo[1,5-a]pyrimidin-7-yl.

The term "aryl" set forth under R$^3$ and R$^4$ embraces phenyl or polynuclear aromatic such as naphthyl, anthryl or phenanthryl residues which are unsubstituted or are mono- or disubstituted by halogen, hydroxy, cyano, nitro, lower alkyl or lower alkoxy.

The term "aralkyl" set forth under R$^4$ embraces a lower alkyl group which is substituted by an aryl group, as defined above, such as e.g. benzyl.

The term "aryloxy" set forth under R$^4$ embraces aryl-O—.

The term "aralkyloxy" as used herein refers to an oxygen radical having an aralkyl substituent.

The term "heterocyclyl" set forth under R$^3$ and R$^4$ embraces a 5- or 6-membered ring optionally containing nitrogen, sulphur and/or oxygen, moieties such as e.g. pyridyl, pyridiniumyl, pyrazinyl, piperidyl, piperidino, N-oxido-pyridyl, pyrimidyl, piperazinyl, pyrrolidinyl, pyridazinyl, N-oxido-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, thienyl, furyl, hexamethylene-iminyl, 1H-azepinyl, thiophenyl, tetrahydrothiophenyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, 1,6,3,4-dioxadithiophenyl, oxazolidinyl, tetrahydrothienyl, quinolinyl, quinoliniumyl and the like. Substituents on the heterocyclic ring comprise: lower alkyl groups such as methyl, ethyl, propyl, etc., lower alkoxy groups such as methoxy, ethoxy etc., halogens such as fluorine, chlorine, bromine etc., halo-substituted alkyl groups such as trifluoromethyl, trichloroethyl etc., amino, mercapto, hydroxyl, carbamoyl or carboxyl groups as well as those additional substituents found on the 5- or 6-membered ring optionally containing nitrogen, sulfur and/or oxygen as discussed above. A further substituent is the oxo group such as in 2-oxo-oxazolidin-3-yl, 1,1-dioxotetrahydrothien-3-yl. Further examples for substituted heterocycles are 6-methoxy-pyridin-3-yl, 5-methyl-isoxazol-3-yl, 1-methyl-4-pyridinio. Additional substituents include, unsubstituted aryl or aryl substituted by one or two substituents selected from halogen, hydroxy, cyano, nitro, lower alkyl, lower alkoxy, aralkyl, —$CONR^5R^6$, —$CH_2$—$CONR^5R^6$, —$N(R^6)COOR^7$, $R^6CO$—, $R^6OCO$— or $R^6COO$— in which $R^5$ signifies hydrogen, lower alkyl or lower cycloalkyl; $R^6$ signifies hydrogen or lower alkyl; and $R^7$ signifies hydrogen, lower alkyl, lower alkenyl or a carboxylic acid protecting group, aralkyl, and —$CONR^5R^6$, —$CH_2$—$CONR^5R^6$, —$N(R^6)COOR^7$, $R^6CO$—, $R^6OCO$— or $R^6COO$— in which $R^5$ signifies hydrogen, lower alkyl or lower cycloalkyl; $R^6$ signifies hydrogen or lower alkyl; and $R^7$ signifies hydrogen, lower alkyl, lower alkenyl or a carboxylic acid protecting group The term "heterocyclylalkyl" set forth under $R^4$ embraces a lower alkyl group which is substituted by a heterocyclyl group, such as e.g. thiophen-2 yl-methyl.

The term "amino protecting groups" refers to protecting groups conventionally used to replace an acidic proton of an amino group. Examples of such groups are described in Green, T., Protective Groups in Organic Synthesis, Chapter 7, John Wiley and Sons, Inc. (1981), pp. 218–287, herein incorporated by reference. These examples include the carbamates of methyl, cyclopropylmethyl, 1-methyl-1-cyclopropylmethyl, diisopropylmethyl, 9-fluorenylmethyl, 9-(2-sulfo)fluorenylmethyl, 2-furanylmethyl, 2,2,2-trichloroethyl, 2-haloethyl, 2-iodoethyl, 2-trimethylsilylethyl, 2-methylthioethyl, 2-methylsulfonylethyl, 2-(p-toluenesulfonyl)ethyl, 2-phosphonioethyl, 1,1-dimethyl-3-(N,N-dimethylcarboxamido)propyl, 1,1-diphenyl-3-(N,N-diethylamino)propyl, 1-methyl-1-(1-adamantyl)ethyl, 1-methyl-1-phenylethyl, 1-methyl-1-(3,5-dimethoxyphenyl)ethyl, 1-methyl-1-(4-biphenylyl)ethyl, 1-methyl-1-(p-phenylazophenyl)ethyl, 1,1-dimethyl-2-haloethyl, 1,1-dimethyl-2,2,2-trichloroethyl, 1,1-diemthyl-2-cyanoethyl, isobutyl, t-butyl, t-amyl, cyclobutyl, 1-methylcyclobutyl, cyclopentyl, cyclohexyl, 1-methylcyclohexyl, 1-adamantyl, isobornyl, vinyl, allyl, cinnamyl, phenyl, 2,4,6-tri-t-butylphenyl, m-nitrophenyl, S-phenyl, 8-quinolyl, N-hydroxypiperidinyl, 4-(1,4-dimethylpiperdinyl), 4,5-diphenyl-3-oxazolin-2-one, benzyl, 2,4,6-trimethylbenzyl, p-methoxybenzyl, 3,5-dimethoxybenzyl, p-decyloxybenzyl, p-nitrobenzyl, o-nitrobenzyl, 3,4-dimethoxy-6-nitrobenzyl, p-bromobenzyl, chlorobenzyl, 2,4-dichlorobenzyl, p-cyanobenzyl, o-(N,N-dimethylcarboxamide)benzyl, m-chloro-p-acyloxybenzyl, p-(dihydroxyboryl)-benzyl, p-(phenylazo)benzyl, p-(p'-methoxyphenylazo)benzyl, 5-benzisoxazolylmethyl, 9-anthrylmethyl, diphenylmethyl, phenyl(o-nitrophenyl)methyl, di(2-pyridyl)methyl, 1-methyl-1-(4-pyridyl)-ethyl, isonicotinyl, S-benzyl, N'-piperidinylcarbonyl, N'-p-touluenesulfonylaminocarbonyl, N'-phenylaminothiocarbonyl; the amides of N-formyl, N-acetyl, N-chloroacetyl, N-dichloroacetyl, N-trichloroacetyl, N-trifluoroacetyl, N-o-nitrophenylacetyl, N-o-nitrophenoxyacetyl, N-acetoacetyl, N-acetylpyridinium, N-(N'-dithiobenzyloxycarbonylamino)acetyl, N-3-phenylpropionyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)-propionyl, N-4-chlorobutyryl, N-isobutyryl, N-o-nitrocinnamoyl, N-picolinoyl, N-(N'acetylmethionyl), N-(N'benzoyl-phenylalkanyl), N-benzoyl, N-p-phenylbenzoyl, N-p-methoxybenzoyl, N-o-nitrobenzoyl, N-o-(benzoyloxymethyl)benzoyl, N-p-P-benzoyl; the cyclic imides of N-phthaloyl, N-2,3-diphenylmaleoyl, N-dithiasuccinoyl; N-allyl, N-allyloxycarbonyl, N-phenacyl, N-3-acetoxypropyl, N-(4-nitro-1-cyclohexyl-2-oxo-3-pyrrolin-3-yl), quaternary ammonium salts, N-methoxymethyl, N-2-chloroethoxymethyl, N-benzyloxymethyl, N-pivaloyloxymethyl, N-[1-(alkoxycarbonylamino)-2,2,2-trifluoro]ethyl, N-[1-trifluoromethyl-1-(p-chlorophenoxymethoxy)-2,2,2-trifluoro]ethyl, N-2-tetrahydro-pyranyl, N-2,4-dinitrophenyl, N-benzyl, N-3,4-dimethoxybenzyl, N-o-nitrobenzyl, N-di(p-methoxyphenyl)methyl, N-triphenylmethyl, N-(p-methoxyphenyl)diphenylmethyl, N-diphenyl-4-pyridylmethyl, M-2-picolyl N'-oxide, N-5-dibenzosuberyl, N-(N',N'-dimethylaminomethylene), N,N'-isopropylidene, N-benzylidene, N-p-methoxybenzyidene, N-p-nitrobenzylidene, N-salicylidene, N-5-chlorosalicylidene, N-diphenylmethylene, N-(5-chloro-2-hydroxyphenyl)phenyl-methylene, N-(acylvinyl), N-(5,5-dimethyl-3-oxo-1-cyclohexenyl), N-borane, N-[phenyl(pentacarbonylchromium or -tungsten)]carbonyl, N-copper or N-zinc chelate, N-nitro, N-nitroso, N-oxide, N-diphenylphosphinyl, N-dimethylthiophosphinyl, N-diphenylthiophosphinyl, N-diethyl phosphoryl, N-dibenzyl phosphoryl, N-diphenyl phosphoryl, N-trimethylsilyl, N-benzenesulfenyl, N-o-nitrobenzenesulfenyl, N-2,4-dinitrobenzenesulfenyl, N-2-nitro-4-methoxybenzenesulfenyl, N-triphenylmethylsulfenyl, N-benzenesulfonyl, N-p-methoxybenzenesulfonyl, N-2,4,6-trimethylbenzensulfonyl, N-toluenesulfonyl, N-benzylsulfonyl, N-p-methylbenzylsulfonyl, N-trifluoromethylsulfonyl, N-phenacylsulfonyl. Other amino protecting groups include t-butoxycarbonyl (abbreviated BOC), benzyloxycarbonyl and allyloxycarbonyl.

The term "carboxylic acid protecting group" refers to protecting groups conventionally used to replace the acidic proton of a carboxylic acid. Examples of such groups are described in Greene, T., Protective Groups in Organic Synthesis, Chapter 5, pp. 152–192 (John Wiley and Sons, Inc. 1981), incorporated herein by reference. These examples include methoxymethyl, methylthiomethyl, tetrahydropyranyl, tetrahydrofuranyl, methoxyethoxymethyl, benzyloxymethyl, phenacyl, p-bromophenacyl, α-methylphenacyl, p-methoxyphenacyl, diacylmethyl, N-phthalimidomethyl, ethyl, 2,2,2-trichloroethyl, 2-haloethyl, ω-chloroalkyl, 2-(trimethylsilyl)

ethyl, 2-methylthioethyl, 2-(p-nitrophenylsulfenyl)ethyl, 2-(p-toluenesulfonyl)ethyl, 1-methyl-1-phenylethyl, t-butyl, cyclopentyl, cyclohexyl, allyl, cinnamyl, phenyl, p-methylthiophenyl, benzyl, triphenylmethyl, diphenylmethyl, bis(o-nitrophenyl)methyl, 9-anthrylmethyl, 2-(9,10-dioxo)anthrylmethyl, 5-dibenzosuberyl, 2,4,6-trimethylbenzyl, p-bromobenzyl, o-nitrobenzyl, p-nitrobenzyl, p-methoxybenzyl, piperonyl, 4-picolyl, trimethylsilyl, triethylsilyl, t-butyldimethylsilyl, i-propyl-dimethylsilyl, phenyldimethylsilyl, S-t-butyl, S-phenyl, S-2-pyridyl, N-hydroxypiperidinyl, N-hydroxysuccinimidoyl, N-hydroxyphthalimidoyl, N-hydroxybenzotriazolyl, O-acyl oximes, 2,4-dinitrophenylsulfenyl, 2-alkyl-1,3-oxazolines, 4-alkyl-5-oxo-1,3-oxazolidines, 5-alkyl-4-oxo-1,3-dioxolanes, triethylstannyl, tri-n-butylstannyl; the amides or hydrazides of N,N-dimethylamino, pyrrolidinyl, piperidinyl, o-nitrophenyl, 7-nitroindolyl, 8-nitrotetra-hydroquinolyl, p-benzenesulfonamide, hydrazides, N-phenylhydrazide, N,N'-diisopropylhydrazide. Preferred are benzyhydryl, t-butyl, p-nitrobenzyl, p-methoxybenzyl and allyl.

One preferred sub-group of R has formula (a)

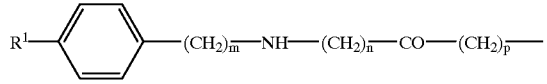
(a)

wherein $R^1$ represents hydrogen, hydroxy, carbamoyl or sulphamoyl and m, n and p each represent 0 or 1.

Sub-groups of (a) are:

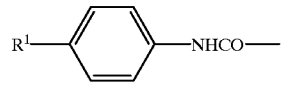
(a1)

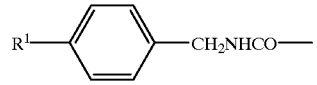
(a2)

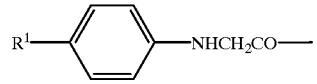
(a3)

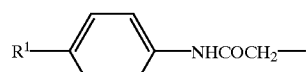
(a4)

Preferred groups R are 4-hydroxyphenylcarbamoyl, 4-carbamoylphenylcarbamoyl, formyl, acetyl, trifluoroacetyl, methanesulphonyl or a residue of formula (a5)

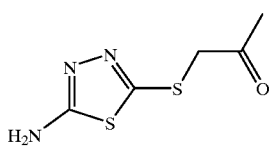
(a5)

Preferred residues $R^3$ in a group of the formula

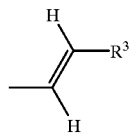
(b1)

set forth under A are: phenyl, substituted phenyl such as e.g. p-hydroxyphenyl, pyridin-2-, -3- or -4-yl, quinolin-2-, -3- or -4-yl, and pyridin-1-ium-2- or -3-yl residues such as e.g. residues of the following formulae

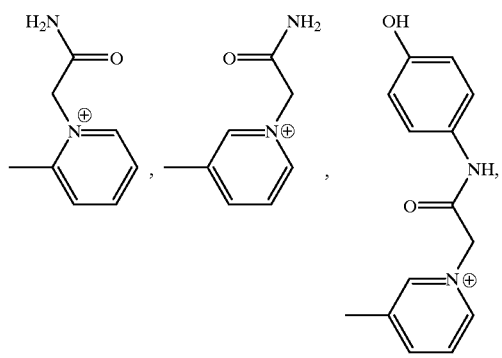

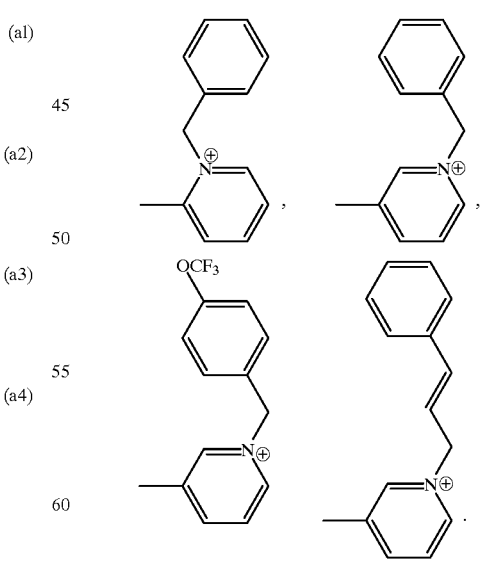

as well as 1-carbamoylmethyl-quinolin-1-ium-3-yl residues of the following formula Preferred significances for R⁴ in a group of the formula (b2)

set forth under A are:
2,2,2-trifluoroethyl
isobutyl,
cyclopropyl,
phenyl,
p-hydroxyphenyl,
m-nitrophenyl,
p-nitrobenzyl,
pyridin-2-, -3- or -4-yl,
pyridin-1-ium-2-, -3- or -4- yl such as e.g. 1-benzyl-pyridin-1-ium-2-yl, 1-benzyl-pyridin-1-ium-3-yl, 1-benzyl-pyridin-1-ium-4-yl, 4-trifluoromethoxy-benzyl-pyridin-1-ium-3-yl, 1-carbamoylmethyl-pyridin-1-ium-2-yl, 1-carbamoylmethyl-pyridin-1-ium-3-yl, 1-carbamoylmethyl-pyridin-1-ium-4-yl and 4-hydroxyphenylcarbamoyl-methyl-pyridin-1-ium-3-yl,
quinolyl-3-yl, quinolyl-2-yl, 1-carbamoylmethyl-quinolin-1-ium-3-yl,
thiophen-2-yl-methyl
ethoxycarbonyl-piperidin-4-yl,
pyrazinyl,
pyridazinyl,
pyrimidin-2-yl,
thiadiazolyl,
2-oxotetrahydrofuranyl,
tetrazol-5-yl-methyl,
tetrahydrofuranyl and
benzimidazolyl.

Especially preferred compounds of formula I and, respectively, their salts are:

(E)-(1aS,3aR,6bR)-2-Acetyl-1-oxo-5-[2-oxo-1-(4-hydroxyphenyl)-pyrrolidin-3-ylidenemethyl]-1a,2,3,3a,4,6b-hexahydro-1H-2,6a-diaza-cyclobut[cd]indene-6-carboxylic acid sodium salt (1:1) (Example 24)

(E)-(1aS,3aR,6bR)-2-Acetyl-1-oxo-5-[2-oxo-1-(2,2,2-trifluoro-ethyl)-pyrrolidin-3-ylidenemethyl]-1a,2,3,3a,4,6b-hexahydro-1H-2,6a-diaza-cyclobut[cd]indene-6-carboxylic acid sodium salt (1:1) (Example 25)

(E)-(1aS,3aR,6bR)-2-Acetyl-1-oxo-5-[2-oxo-1-(thiophen-2-ylmethyl)-pyrrolidin-3-ylidenemethyl]-1a,2,3,3a,4,6b-hexahydro-1h-2,6a-diaza-cyclobut[cd]indene-6-carboxylic acid sodium salt (1:1) (Example 27)

(E)-(1aS,3aR,6bR)-2-Acetyl-1-oxo-5-[2-oxo-1-isobutyl-pyrrolidin-3-ylidenemethyl]-1a,2,3,3a,4,6b-hexahydro-1H-2,6a-diaza-cyclobut[cd]indene-6-carboxylic acid sodium salt (1:1) (Example 28)

(E)-(1aS,3aR,6bR)-2-Acetyl-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-6-carboxylic acid sodium salt (1:1) (Example 29)

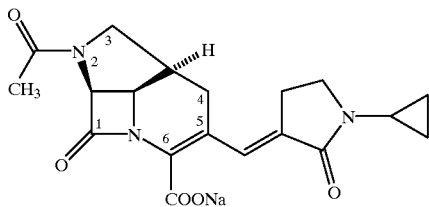

(E)-(1aS,3aR,6bR)-2-Acetyl-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-6-carboxylic acid sodium salt (1:1) (Example 33)

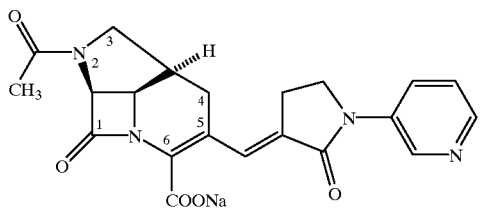

(E)-(1aS,3aR,6bR)-2-Acetyl-5-[2-(1-benzyl-pyridin-1-ium-3-yl)-vinyl]-1-oxo-1a,2,3,3a,4,6b-hexahydro-1H-2,6a-diaza-cyclobut[cd]indene-6-carboxylic acid sodium salt (1:1) (Example 66)

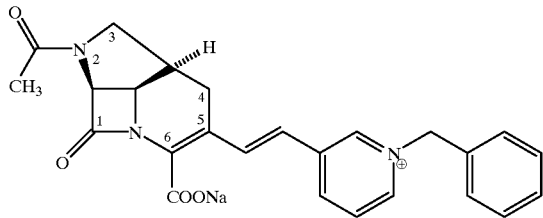

(E)-(1aS,3aR,6bR)-2-Acetyl-5-[2-(1-carbamoylmethyl-pyridin-1-ium-3-yl)-vinyl]-1-oxo-1a,2,3,3a,4,6b-hexahydro-1H-2,6a-diaza-cyclobut[cd]indene-6-carboxylic acid sodium salt (1:1) (Example 67)

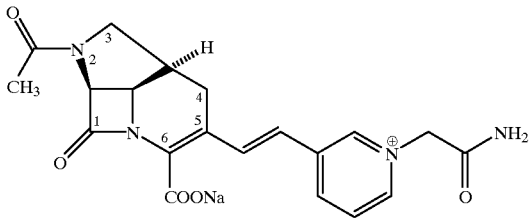

(E)-(1aS,3aR,6bR)-2-Acetyl-5-[2-[1-[(4-hydroxyphenyl-carbamoyl)-methyl]-pyridin-1-ium-3-yl]-vinyl]-1-oxo-1a,2,3,3a,4,6b-hexahydro-1H-2,6a-diaza-cyclobut[cd]indene-6-carboxylic acid sodium salt (1:1) (Example 70)

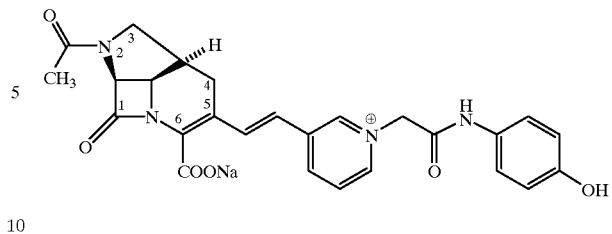

(1aS,3aR,6bR)-2-Acetyl-1-oxo-5-[(E)-2-[1-[(E)-3-phenyl-allyl]-pyridin-1-ium-3-yl)-vinyl]-1a,2,3,3a,4,6b-hexahydro-1H-2,6a-diaza-cyclobut[cd]indene-6-carboxylic acid sodium salt (1:1) (Example 69)

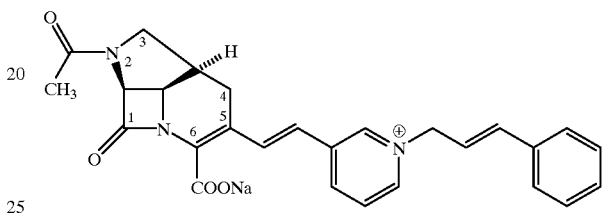

As readily hydrolyzable esters of the compounds of formula I there are to be understood compounds of formula I in which the carboxy group or carboxy groups (e.g. the 6-carboxy group) is/are present in the form of a readily hydrolyzable ester group. Examples of such esters, which can be of the conventional type, are the lower alkanoyloxyalkyl esters, e.g. the acetoxymethyl, pivaloyloxymethyl, 1-acetoxyethyl and the 1-pivaloyloxyethyl esters; the lower alkoxycarbonyloxyalkyl esters, e.g. the methoxycarbonyloxymethyl, 1-ethoxycarbonyloxyethyl and the 1-isopropoxycarbonyloxyethyl esters; the 1-cyclohexyloxycarbonyloxyethyl ester; the (5-methyl-2-oxo-1,3-dioxol-4-yl)-methyl ester; the lactonyl esters, e.g. the phthalidyl and the thiophthalidyl esters; the lower alkoxymethyl esters, e.g. the methoxymethyl ester, and the lower alkanoylaminomethyl esters, e.g. the acetamidomethyl ester. Other esters, e.g. the benzyl and cyanomethyl esters, can also be used. Further readily hydrolyzable esters are the (2,2-dimethyl-1-oxopropoxy)methyl ester, the 2-[(2-methylpropoxy)carbonyl]-2-pentenyl ester, the 1-[[(1-methylethoxy)carbonyl]oxy]ethyl ester and the 3,3-dimethyl-2-oxobutyl ester.

Examples of salts of the compounds of formula I are alkali metal salts, such as the sodium salt and the potassium salt; ammonium salts; alkaline earth metal salts, such as the calcium salt; salts with organic bases, such as salts with amines, e.g. salts with N-ethylpiperidine, procaine, dibenzylamine, N,N'-dibenzylethylenediamine, alkylamines or dialkylamines, as well as salts with amino acids, such as e.g. salts with arginine or lysine.

The compounds of formula I in accordance with the invention as well as their pharmaceutically compatible salts can be made in accordance with the invention by a) cleaving off the carboxy protecting group and an amino protecting group which may be present in a compound of formula II

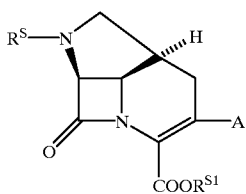

II in which A has the significance given above, $R^S$ has the significance given for R or is an amino protecting group and $R^{S1}$ represents a carboxy protecting group, and, if desired, treating a compound of formula III

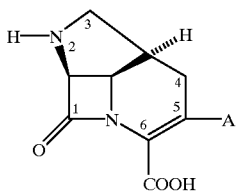

III in which A has the significance given above, which may be obtained with an agent yielding the residue R and, if necessary, cleaving off any protecting groups still present, or b) for making a readily hydrolyzable ester of a compound of formula I, subjecting a carboxylic acid of formula I to a corresponding esterification, or c) for making pharmaceutically compatible salts of a compound of formula I, converting a compound of formula I into such a salt.

The cleavage of protecting groups in compounds of formula II with $R^{S1}$=t-butyl or $R^S$=t-butoxycarbonyl is effected by treatment with an acidic agent, preferably with trifluoroacetic acid, in an organic solvent such as methylene chloride, optionally in the presence of anisole, phenol, cresol or triethylsilane, or also with hydrogen chloride in an organic solvent such as dioxan, tetrahydrofuran or methylene chloride. The temperature preferably lies between −20° C. and room temperature.

Analogous intermediates with other protecting groups (e.g. benzyloxycarbonyl or chloroacetyl in position 2; p-nitrobenzyl, benzyl or benzylhydryl in position 6) are also suitable for the above protecting group cleavage. The starting materials are prepared analogously and the protecting group cleavage is carried out in a manner known per se, e.g.:

Position 2

Benzyloxycarbonyl: hydrogenation with palladium/carbon or treatment with palladium/carbon and 1,4-cyclohexadiene in an organic solvent such as ethanol, tetrahydrofuran, dioxan, ethyl acetate or dimethylformamide (optionally aqueous) at about 0–80° C.;

chloroacetyl: using thiourea in a polar solvent, preferably in water at neutral pH, and about 0–30° C.; or also with an alkali metal bicarbonate, e.g. sodium bicarbonate, in methanol and/or tetrahydrofuran (optionally aqueous) at about 0–30° C.

Position 6

Benzyl and p-nitrobenzyl: hydrogenation with palladium/carbon or palladium oxide at about 0° C. to 80° C. in an organic solvent such as ethyl acetate, methanol or tetrahydrofuran, or in water, optionally in the presence of an acid such as acetic acid or hydrochloric acid; or hydrolysis in the presence of sodium sulphide at about 0° C. to room temperature in a solvent such as e.g. dimethylformamide (preferably aqueous).

Benzhydryl: using m-cresol at about 50° C.

In order to introduce a residue R in position 2, the compound of formula III is e.g. acylated with an acid of the formula ROH or with one of its reactive derivatives.

For making the readily hydrolyzable esters of the carboxylic acids of formula I in accordance with variant b) of the process in accordance with the invention, the carboxylic acid is preferably reacted with the corresponding halide, preferably with the iodide, which contains the ester group. The reaction can be accelerated with the aid of a base, e.g. an alkali metal hydroxide or carbonate or an organic amine such as triethylamine. The esterification is preferably carried out in an inert organic solvent such as dimethylacetamide, hexamethylphosphoric acid triamide, dimethyl sulphoxide or, preferably, dimethylformamide. The temperature preferably lies in the range of about 0–40° C.

The making of the salts of the compounds of formula I in accordance with variant c) of the process in accordance with the invention can be effected in a manner known per se, e.g. by reacting the carboxylic acid of formula I with an equimolar amount of the desired base, conveniently in a solvent such as water or in an organic solvent such as ethanol, methanol, acetone and the like. Correspondingly, salt formation is brought about by addition of an organic or inorganic acid. The temperature at which the salt formation is carried out is not critical, it generally lies at room temperature, but can also lie slightly thereover or thereunder, for example in the range of 0° C. to +50° C.

The following Reaction Schemes I and II illustrate the process for making the products in accordance with the invention and, respectively, of the intermediates which occur in the process. Scheme I shows the making of compounds in which residue A is a N-substituted 2-oxo-pyrrolidin-3-ylidene-methyl group. Scheme II shows the making of compounds in which residue A is a substituted ethene-1,2-diyl group.

Scheme 1

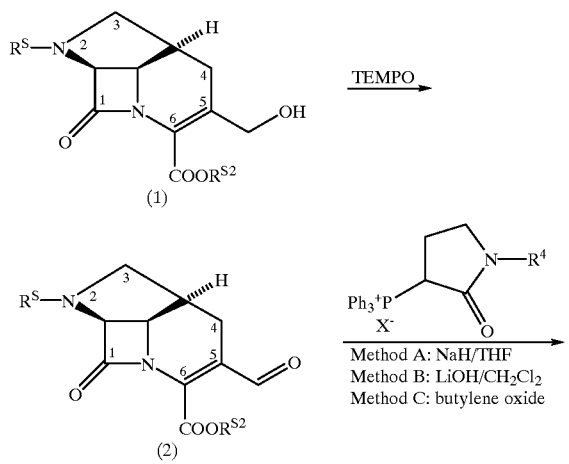

15
-continued

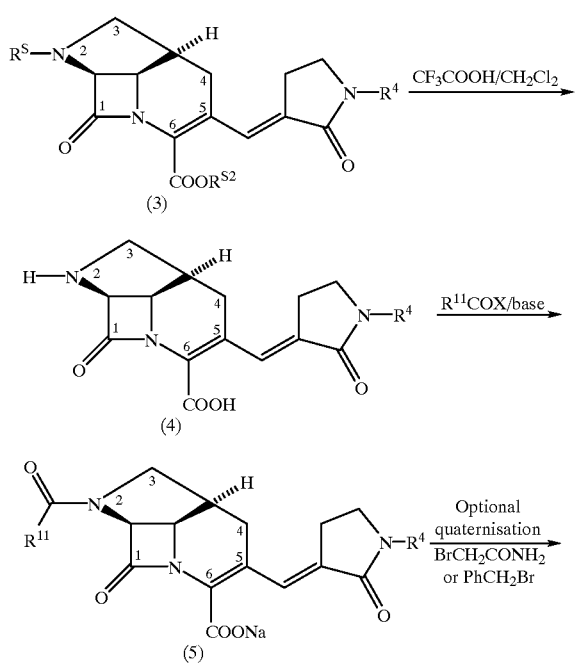

16
-continued

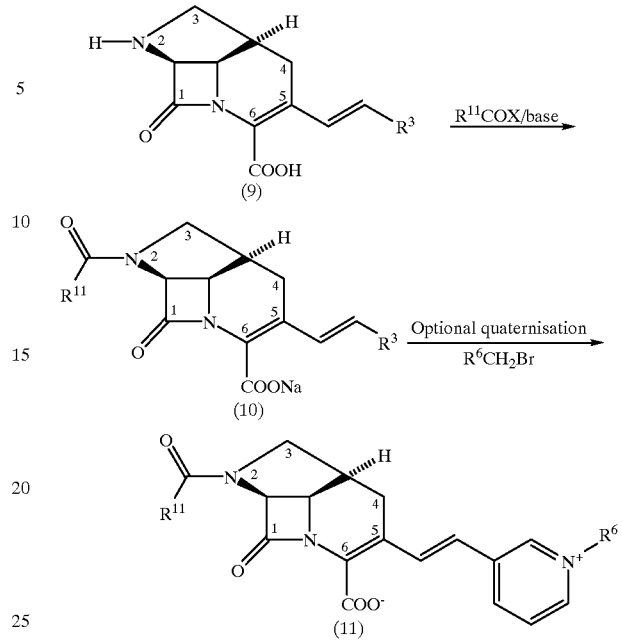

The symbols have the following significances in Reaction Schemes I and II:

$R^{S2}$=a carboxy protecting group, preferably t-butyl;
$R^S$=an amino protecting group, preferably t-butoxycarbonyl;
$R^3$=significance given under formula (b1);
$R^4$=significance given under formula (b2);
$R^5$=benzyl, methylcarbamoyl;
$R^6$=benzyl, 4-trifluoromethoxy-benzyl, methylcarbamoyl, 4-hydroxy-phenylcarbamoyl-methyl;
$R^{11}$=hydrogen, lower alkyl, halo-substituted lower alkyl such as e.g. trifluoromethyl, 4-carbamoyl-phenylamino;
X=halogen.

Scheme 1

(1)→(2)

The oxidation of the 5-hydroxy compound (1) to the corresponding aldehyde (2) takes place in the presence of the 2,2,6,6-tetramethyl-1-piperidinyloxyl radical (TEMPO).

The TEMPO-catalyzed oxidation is effected in the presence of a suitable solvent such as methylene chloride and the like.

The oxidation system contains a base, e.g. sodium acetate, sodium bicarbonate and the like, for the neutralization of the resulting hydrochloric acid.

The oxidation can be conveniently effected in a temperature range of −15° C.–50° C., preferably at 0° C.–5° C. Conveniently, the oxidation is carried out under atmospheric pressure.

(2)→(3)

The aldehyde (2) is reacted with a Wittig reagent to give the addition product (3). The reaction is carried out in the presence of a base, preferably in the presence of sodium hydride or lithium hydride. Tertiary amines or organolithium compounds are also suitable. Water-miscible solvents such as acetone, tetrahydrofuran, methylene chloride, chloroform, dichloroethane and alcohols are suitable solvents. The reaction is effected in a temperature range of (−20)° C. to 25° C.

Scheme 2

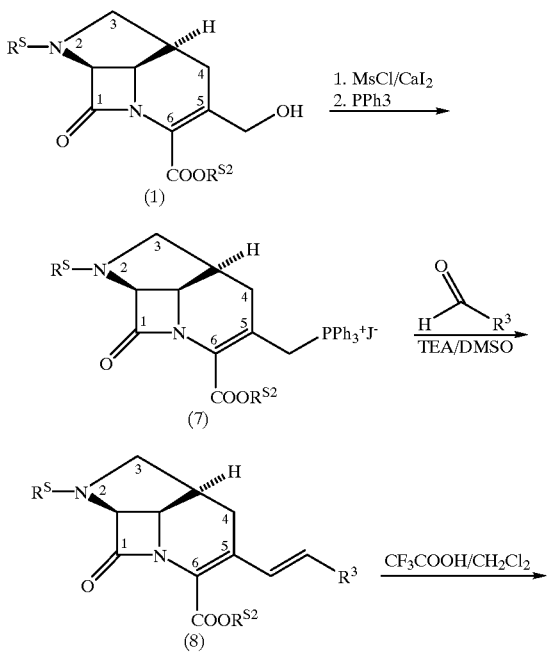

The reaction of the aldehyde (2) with the Wittig reagent can also be effected by heating under reflux in epoxybutane.

(3)→(4)

The protecting groups are removed by reaction with e.g. trifluoroacetic acid in a temperature range of (−20)° C. to room temperature.

(4)→(5) The acylation of compound (4) is effected with acylating agents such as corresponding acids of the formula ROH in the presence of 2-halopyridinium salts, e.g. of 2-chloro- or 2-fluoro-1-methylpyridinium chloride or tosylate, or also in the presence of carbonyldiimidazole or N,N'-dicyclohexylcarbodiimide, the latter preferably together with N-hydroxybenztriazole, N-hydroxysuccinimide or N-hydroxyphthalimide. Corresponding reactive derivatives of the carboxylic acid, such as e.g. the acid halide (preferably the chloride), acid anhydride or acid azide, can also be used. The corresponding thiol esters, such as e.g. 2-benzthiazolyl thioester, as well as hydroxybenztriazole ester, N-hydroxysuccinimide ester or N-hydroxyphthalimide ester are likewise useable. The reaction is preferably carried out in an organic solvent or solvent mixture, e.g. acetone, methylene chloride, tetrahydrofuran, dioxan, dimethylacetamide, dimethylformamide, dimethyl sulphoxide or acetonitrile. The temperature generally lies between (−30)° C. and room temperature.

(5)→(6)

When the residue $R^4$ includes a nitrogen-containing group such as pyridyl, piperidino or quinolinyl, then a quaternisation of the nitrogen atom can be effected by reaction with benzyl bromide or bromoacetamide.

Scheme 2

(1)→(7)→(8)

The reaction of the 5-hydroxy compound (1) with methanesulphonyl chloride/$CaI_2$ and triphenylphosphine gives the Wittig reagent (7) which can then be converted into the addition product (8) by reaction with an aromatic aldehyde.

(8)→(9)→(10)

The removal of the protecting groups, the acylation and, if desired, the quaternisation are effected under comparable conditions to those set forth under Scheme 1, (3)→(4)→(5)→(6)

As mentioned earlier, the compounds of formula I in accordance with the invention and pharmaceutically compatible salts exhibit, in addition to their β-lactamase-inhibiting activity, an improved spectrum of activity against gram-positive and gram-negative microorganisms as well as against β-lactamase producing strains.

These therapeutically valuable properties can be determined in vitro as illustrated hereinafter.

A. Isolation of the β-lactamases

Various β-lactamases can be isolated from penicillin-resistant or cephalosporin-resistant bacterial strains such as *Klebsiella pneumoniae* NCTC 418, *Proteus vulgaris* 1028, *Bacillus licheniformis* 749/C, *Escherichia coli* SN01 and *Citrobacter freundii* 1203. For this purpose, the corresponding strains are cultivated in Tryptic Soy Broth (Difco) and harvested by centrifugation in the last logarithmic growth phase (when necessary 50–100 mg/l of ampicillin are added to the medium towards the end of the log-phase in order to induce the β-lactamase). The thus-obtained bacterial mass is treated with 20 mM Tris-HCI buffer (pH 7.0); the cells are broken open with a French press while cooling. The mixture is centrifuged (20,000 r/min.) for 20–30 minutes and a clear crude extract is obtained. The purification of the proteins is effected according to the methods of Cartwright, S. J. & Waley, S. G. [Biochem. J. 221, 505–512 (1980)] and, for *B. licheniformis*, Ellerby, L. M. et al. [Biochemistry 29, 5797–5806 (1990)].

B. Determination of the β-lactamase Activity

The determination of the activity of the isolated β-lactamases can be carried out according to the method of O'Callaghan, C. H. et al. [Antimicr. Ag. Chemother. 1, 283–288 (1972)] using the chromogenic cephalosporin nitrocefin (87/312 from Glaxo). The requisite test batch contains per ml of water: 50 mM phosphate buffer (pH 7.0), 0.1 mM nitrocefin and sufficient enzyme (β-lactamase) to achieve a ΔA/min. of about 0.1. The cleavage of the substrate, which is accompanied by a change in color, is effected at 37° C. and is followed quantitatively at 482 nm using a spectral photometer.

C. Determination of the β-lactamase-inhibiting Activity of the Compounds of Formula I The above-described cleavage of the chromogenic substrate by β-lactamases (test B.) can be inhibited by the addition of compounds of formula I (inhibitors). Since it has been found that the inhibitors irreversibly inactivate the β-lactamase in a time-dependent reaction, the reaction (cleavage of the substrate) is in each case started by addition of the substrate after a pre-incubation period of β-lactamase with inhibitor of 15 minutes. As a measurement for the affinity of the particular tested inhibitor to the β-lactamase, which is a measurement of the strength of the inhibitor, there serves that concentration which inhibits by 50% (IC 50 in μM) the cleavage of the substrate (nitrocefin) effected under the above test conditions (test B) in the absence of an inhibitor. 4 to 6 tests with different concentrations of inhibitor were carried out in order to determine the IC 50. The determination of the IC 50 was effected by means of a graph.

The results obtained in the above test (test C) are presented in Table 1 hereinafter.

TABLE 1

(Test organism: *Citrobacter freundii* 1982)
The IC 50 value in μM is given for the products of the following Examples. This is a measurement for the β-lactamase inhibition.

| Example No. | IC 50 μM |
| --- | --- |
| 14 | 4.6 |
| 15 | 0.019 |
| 16 | 5.0 |
| 23 | 0.016 |
| 24 | 0.264 |
| 25 | 9.81 |
| 26 | 2.1 |
| 27 | 0.716 |
| 28 | 6.5 |
| 29 | 3.3 |
| 30 | 0.362 |
| 31 | 1.00 |
| 32 | 1.94 |
| 33 | 0.276 |
| 34 | 0.211 |
| 35 | 0.011 |
| 36 | 0.105 |
| 37 | 0.077 |
| 38 | 0.036 |
| 39 | 5.58 |
| 40 | 7.2 |
| 49 | 4.5 |
| 50 | 8.6 |
| 51 | 5.0 |
| 52 | 0.553 |

TABLE 1-continued (Test organism: *Citrobacter freundii* 1982)
The IC 50 value in μM is given for the products of the following
Examples. This is a measurement for the β-lactamase inhibition.

| Example No. | IC 50 μM |
|---|---|
| 53 | 3.3 |
| 54 | 5.1 |
| 55 | 5.3 |
| 56 | 0.247 |
| 57 | 0.020 |
| 58 | 0.033 |
| 59 | 0.022 |
| 60 | 0.027 |
| 61 | 0.024 |
| 62 | 0.010 |
| 63 | 0.067 |
| 64 | 0.011 |
| 66 | 0.550 |
| 67 | 0.141 |
| 68 | 2.62 |
| 69 | 0.310 |
| 70 | 0.081 |
| 71 | 0.865 |
| 72 | 13 |

D. Antibacterial Activity

The minimum inhibitory concentration in vitro (MIC in μg/ml) of a compound of formula I against *Citrobacter freundii* 1982 and *Staphylococcus aureus* 887 is measured and compiled in Table 2.

TABLE 2

| Example No. | MIC *C. freundii* 1982 μg/ml | MIC *S. aureus* 887 μg/ml |
|---|---|---|
| 14 | 8 | 16 |
| 15 | 32 | 8 |
| 16 | 16 | 8 |
| 23 | 16 | 16 |
| 24 | 1 | 1 |
| 25 | 1 | 4 |
| 26 | 8 | 2 |
| 27 | 4 | 2 |
| 28 | 2 | 8 |
| 29 | 1 | 16 |
| 30 | 4 | 1 |
| 31 | 8 | 2 |
| 32 | 62 | 8 |
| 33 | 1 | 2 |
| 34 | 8 | 4 |
| 35 | 32 | 4 |
| 36 | 8 | 4 |
| 37 | 64 | 4 |
| 38 | 16 | 4 |
| 39 | 4 | 2 |
| 40 | 4 | 2 |
| 49 | 64 | 8 |
| 50 | 64 | 64 |
| 51 | 64 | 4 |
| 52 | 64 | 4 |
| 53 | 64 | 2 |
| 54 | 64 | 64 |
| 55 | 64 | 4 |
| 56 | 4 | 1 |
| 57 | 64 | 4 |
| 58 | 4 | 2 |
| 59 | 32 | 1 |
| 60 | 32 | 2 |
| 61 | 64 | 64 |
| 62 | 8 | 2 |
| 63 | 64 | 0.5 |
| 64 | 32 | 2 |
| 66 | 8 | 0.25 |
| 67 | 16 | 0.25 |
| 68 | 16 | 0.5 |
| 69 | 32 | 0.25 |
| 70 | 8 | 0.25 |
| 71 | 64 | 0.5 |
| 72 | 64 | 64 |

The products in accordance with the invention can be used as medicaments, e.g. in the form of pharmaceutical preparations, preferably for parenteral administration.

For this purpose, the products of the present invention are preferably made into preparations as lyophilisates or dry powders for dilution with customary agents, such as, for example, water or isotonic common salt solution.

The products in accordance with the invention can be used as medicaments, for example, in the form of pharmaceutical preparations for enteral (oral) administration. The products in accordance with the invention can be administered, for example, perorally, such as in the form of tablets, coated tablets, dragees, hard and soft gelatine capsules, solutions, emulsions or suspensions, or rectally, such as in the form of suppositories.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipitated aluminum hydroxide-calcium carbonate, dicalcium phosphate or lactose; disintegrating agents, such as maize starch; and lubricating agents, such as talc, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, coated tablets, dragees and hard gelatine capsules there can be used, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance; no carriers are, however, required in the case of soft gelatine capsules). Suitable carrier materials for the preparation of solutions and syrups are, for example, water, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavorants, salts for varying the osmotic pressure, buffers, coating agents and antioxidants.

As mentioned earlier, the compounds in accordance with the invention can be used in the control or prevention of infectious diseases, especially in the control of β-lactamase forming pathogens alone or in combination with β-lactam antibiotics, i.e. antibiotics which contain a β-lactam ring, for example penicillins such as benzylpenicillin, piperacillin, phenoxymethylpenicillin, carbenicillin, apalcillin, methicillin, propicillin, tricarcillin, ampicillin, amoxicillin or mecillinam, or cephalosporins such as ceftriaxone, ceftazidime, cefetamet, cefetamet pivoxil, cefotaxime, cefmenoxime, ceftizoxime, cefuroxime, cephaloridine, cephalotin, cefazolin, cephalexin, cefoxitin, cephacetrile, cefamandole, cephapirin, cephradine, cephaloglycine, (6R, 7R)-7-[(Z)-2-(2-amino-4-thiazolyl)-2-(methoxyimino) acetamido]-3-(azidomethyl)-8-oxo-5-thia-1-azabicyclo [4.2.0]oct-2-ene-2-carboxylic acid or (E)-2-(isobutoxycarbonyl)-2-pentenyl (6R,7R)-7-[(Z)-2-(2-amino-4-thiazolyl)-2-(methoxyimino)acetamido]-3-(azidomethyl)-8-oxo-5-thia-1-azabicyclo[4.2.0]oct-2-ene-2-carboxylate or also penems or carbapenems such as imipenem and meropenem. Thereby, the compounds of formula I or pharmaceutically compatible salts thereof with bases can be administered before, simultaneously with or after the administration or intake of β-lactam antibiotics. When the products in accordance with the invention are administered simultaneously with a β-lactam antibiotic, then this can be effected by administration as an ad-hoc combination or in the form of a pharmaceutical combination which contains a compound of formula I or a pharmaceutically compatible salt thereof with a base and a β-lactam antibiotic; such pharmaceutical combinations are also an object of the present invention.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, and more especially about 100 mg to about 200 mg is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated. The ratio of β-lactamase inhibitor (compound of formula I or pharmaceutically compatible salt thereof with a base) to β-lactam antibiotic can also vary within wide limits and will be fitted to the individual requirements in each particular case. In general, the ratio is about 1:20–1:1.

The following Examples illustrate the invention in more detail. In the following Examples DMF is dimethylformamide and THF is tetrahydrofuran.

1. Preparation of the 5-hydroxymethyl Compound Schemes 1 and 2, Compound 1

EXAMPLE 1

Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate

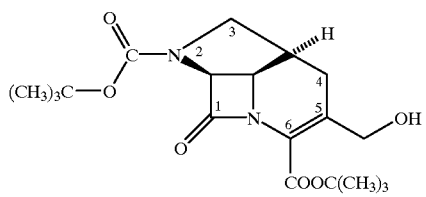

This compound can be obtained by the following reaction sequence a)–f):

a) Mixture of benzyl (E)- and (Z)-(1S,5R)-6-(3,4-dimethoxybenzyl)-7-oxo-4-[2-oxo-3-(2-trimethylsilanyl-ethoxy)-propylidene]-2,6-diazabicyclo[3.2.0]heptane-2-carboxylate 49 g (119.4 mmol) of benzyl (1S,5S)-6-(3,4-dimethoxybenzyl)-4,7-dioxo-2,6-diazabicyclo[3.2.0] heptane-2-carboxylate were placed in abs. methylene chloride (250 ml) and treated dropwise (40 minutes) with 1-[2-(trimethyl-silanyl)-ethoxy]-3-triphenylphosphoranylidene-propan-2-one (51.9 g; 119.4 mmol) in abs. methylene chloride (125 ml). After 2.5 hours at room temperature the reaction mixture was poured into 1N aqueous hydrochloric acid (650 ml) and extracted with methylene chloride (2×300 ml). The combined organic phases were washed with water (3×500 ml) and saturated aqueous sodium chloride solution (500 ml), dried over magnesium sulphate and concentrated. The residue was chromatographed over silica gel (1.7 kg, 0.040–0.063 mm particle size) with ethyl acetate/n-hexane 7:3. Yield: 51.4 g (76%) as a colorless oil.

IR (film): 2840, 1763, 1711 cm$^{-1}$; MS (ISP): (M+H)$^+$ 567.5.

b) t-Butyl (1S,4R,5R)-6-(3,4-dimethoxybenzyl)-7-oxo-4-[2-oxo-3-(2-trimethylsilanyl-ethoxy)-propyl]-2,6-diazabicyclo-[3.2.0]heptane-2-carboxylate The mixture of benzyl (E)- and (Z)-(1S,5R)-6-(3,4-dimethoxybenzyl)-7-oxo-4-[2-oxo-3-(2-trimethylsilanyl-ethoxy)-propylidene]-2,6-diazabicyclo[3.2.0]heptane-2-carboxylate (51.4 g; 90.7 mmol) as prepared above was placed in methanol (2 l), treated with di-t-butyl dicarbonate (29.7 ml; 136 mmol) and hydrogenated over Pd/C (15 g). After 15 hours the reaction mixture was suction filtered, concentrated and chromatographed over silica gel (1 kg, 0.040–0.063 mm particle size) with ethyl acetate/n-hexane 1:1. Yield: 25.7 g (53%) as a colorless foam.

IR (film): 1760, 1699, 1591, 1517, 1160, 887, 765 cm$^{-1}$; MS (ISP): (M+H)$^+$ 535.4; Microanalysis: $C_{27}H_{42}N_2O_7Si$; Calc. C 60.65 H 7.92 N 5.24; Found. C 60.48 H 8.27 N 4.91.

c) t-Butyl (1S,4R,5R)-7-oxo-4-[2-oxo-3-(2-trimethylsilanylethoxy)-propyl]-2,6-diazabicyclo[3.2.0] heptane-2-carboxylate 25.7 g (48 mmol) of t-butyl (1S,4R,5R)-6-(3,4-dimethoxybenzyl)-7-oxo-4-[2-oxo-3-(2-trimethylsilanyl-ethoxy)-propyl]-2,6-diazabicyclo[3.2.0]heptane-2-carboxylate were placed in acetonitrile (500 ml) and water (240 ml). The solution was warmed to 60° C. and treated with potassium persulphate (84 g; 310 mmol) in 4 portions at intervals of 1 hour. Simultaneously, the pH value was held at 5 with a 15% aqueous sodium carbonate solution. After 3 hours at 60° C. the suspension obtained was cooled, the pH was adjusted to 7, the mixture was then diluted with water (200 ml) and extracted with ethyl acetate (2×1000 ml). The combined organic phases were washed with saturated aqueous sodium chloride solution (500 ml), dried over magnesium sulphate and concentrated. The residue was chromatographed over silica gel (1000 g; 0.040×0.063 mm particle size) with ethyl acetate/n-hexane 1:1. Yield: 12.7 g (69%) as a colorless solid. M.p. 89–91° C. (ethyl acetate).

IR (KBr): 3294, 1784, 1729, 1696, 1514, 1250 cm$^{-1}$; Microanalysis: $C_{18}H_{32}N_2O_5Si$; Calc. C 56.22 H 8.39 N 7.28; Found C 55.93 H 8.22 N 7.00.

d) Di-t-butyl (1aS,3aR,6bR)-5-(2-trimethylsilanyl-ethoxymethyl)-1-oxo-1a,2,3,3a,4,6b-hexahydro-1H-2,6a-diazacyclobut[cd]indene-2,6-dicarboxylate t-Butyl (1S,4R,5R)-7-oxo-4-[2-oxo-3-(2-trimethylsilanyl-ethoxy)-propyl]-2,6-diazabicyclo[3.2.0] heptane-2-carboxylate (12.7 g; 33 mmol) and methyldiisopropylamine (7.0 ml; 39.6 mmol) were pre-cooled in abs. methylene chloride (90 ml) to −5° C. and added to a suspension of calcium carbonate (13.1 g; 131 mmol) and t-butyloxalyl chloride (6 ml; 39.6 mmol) in abs. methylene chloride (30 ml) while cooling with an ice bath. After 2 hours at 0° C. the suspension was diluted with ethanol-free chloroform (120 ml) and filtered over silica gel (70 g; 0.040–0.063 mm particle size). Subsequently, the column was rinsed with chloroform (120 ml). The combined organic phases were diluted with abs. toluene (900 ml), treated with triethyl phosphite (11.5 ml; 66 mmol) at room temperature and heated under reflux conditions for 15 hours. The solution obtained was concentrated. The residue was dissolved in ethyl acetate (1200 ml), washed in succession with water (600 ml) and saturated aqueous sodium chloride solution (600 ml) and dried over magnesium sulphate. After concentration the residue was chromatographed over silica gel (600 g; 0.040–0.063 mm particle size) with n-hexane/acetone 9:1. Yield: 8.7 g (55%) as a colorless solid.

IR (KBr): 1764, 1706, 1248, 836, 776 cm$^{-1}$; MS (ISP): (M+H)$^+$ 481.6.

e) t-Butyl (1aS,3aR,6bR)-5-hydroxymethyl-1-oxo-1a,2,3,3a,4,6b-hexahydro-1H-2,6a-diazacyclobut[cd]indene-6-carboxylate.

Di-t-butyl (1aS,3aR,6bR)-5-(2-trimethylsilanyl-ethoxymethyl)-1-oxo-1a,2,3,3a,4,6b-hexahydro-1H-2,6a-diazacyclobut[cd]indene-2,6-dicarboxylate (8.7 g; 18.1 mmol) was dissolved in methylene chloride (30 ml) and added dropwise while stirring vigorously to trifluoroacetic acid (80 ml) pre-cooled to −20° C. (the temperature is held between −18 and −20° C.). After 3 hours at −20° C. the reaction mixture was concentrated at the same temperature, treated with abs. ether (670 ml) and suction filtered. Yield: 5.3 g (74%) as a beige solid.

IR (KBr): 3426, 1773, 1710, 1670, 1180, 1077 cm$^{-1}$; MS (ISP): (M+H)$^+$ 281.2.

f) Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate t-Butyl (1aS,3aR,6bR)-5-hydroxymethyl-1-oxo-1a,2,3,3a,4,6b-hexahydro-1H-2,6a-diazacyclobut[cd]indene-6-carboxylate (5.3 g; 13.4 mmol) was placed in dioxan/water 1:1 (150 ml) and treated with sodium bicarbonate (2.2 g; 26.7 mmol) and di-t-butyl dicarbonate (3.7 ml; 16 mmol) at room temperature. After 1 hour the reaction mixture was poured into saturated aqueous sodium chloride solution (150 ml), extracted with ethyl acetate (3×150 ml), dried over magnesium sulphate and concentrated. The residue was chromatographed over silica gel (150 g, 0.040–0.063 mm particle size) with ethyl acetate. Yield: 3.2 g (63%) as a colorless solid. M.p. 175° C.

IR (KBr): 1761, 1705, 1631, 1253, 1161, 1117, 1087 cm$^{-1}$; MS (ISP): (M+H)$^+$ 381.4.

The 5-hydroxymethyl "compound" can also be obtained according to the following improved method (reaction sequence a1)–g1)):

a1) n-Butyl (t-butyl-dimethyl-silanyloxy)-acetate n-Butyl glycolate (231 g; 1.75 mol) and imidazole (345.1 g; 5.07 mol) were combined at 0° C. The suspension obtained was treated portionwise with t-butyldimethylchlorosilane (303 g; 2.01 mol) over 1.5 hours. After 20 hours at room temperature the reaction mixture was diluted with ether/n-hexane 1:1 (1 l) and suction filtered. The crystals were rinsed thoroughly with ether/n-hexane 1:1 (200 ml). The filtrate was washed in succession with water (2×700 ml) and saturated aqueous sodium chloride solution (500 ml), dried over magnesium sulphate and concentrated. The oil obtained was distilled over a Vigreux column (7.5 cm). Yield: 405 g (94%) as a colorless oil (b.p. 78° C./0.98 mm Hg).

IR (film): 1760, 1225, 1206, 1148, 838, 780 cm$^{-1}$; MS (EI): (M+H)$^+$ 247.

b1) Dimethyl [3-(t-butyl-dimethyl-silanyloxy)-propyl]-phosphonate

Dimethyl methanephosphonate (70 ml; 634.8 mmol) was placed in tetrahydrofuran (1.6 l) at −75° C. and treated at this temperature with 1.6M n-butyllithium in tetrahydrofuran (437 ml; 700 mmol). After 1.5 hours at −75° C. n-butyl (t-butyl-dimethyl-silanyloxy)-acetate (52.1 g; 211.6 mmol) in tetrahydrofuran (110 ml) was added and the batch was stirred for 2 hours at −30° C. The reaction mixture was subsequently poured into 1N ice-cold aqueous hydrochloric acid (800 ml) and extracted rapidly with ethyl acetate (2×1 l). The combined organic phases were washed in succession with water (2×1 l) and saturated aqueous sodium chloride solution (500 ml), dried over magnesium sulphate and concentrated. The residue was azeotroped with toluene (2×300 ml) and distilled (b.p.: 89–95° C.; 0.42 mm Hg). Yield: 57.2 g (92%) as a colorless oil.

IR (film): 1734, 1257, 1033, 840, 780 cm$^{-1}$; MS (EI): (M+H)$^+$ 297.

c1) Benzyl (Z) and (E)-(1S,5R)-4-[3-(t-butyl-dimethyl-silanyl-oxy)-2-oxo-propylidene]-6-(2,4-dimethoxy-benzyl)-7-oxo-2,6-diaza-bicyclo[3.2.0] heptane-2-carboxylate Dimethyl [3-(t-butyl-dimethyl-silanyloxy)-propyl]-phosphonate (39.4 g; 133.2 mmol) was dissolved in THF (177 ml) and cooled to 0° C. Sodium hydride (4.25 g of a 55 to 60% suspension in oil) was added portionwise in such a manner that the temperature does not rise above +5° C. After 40 minutes at 0° C. a solution, pre-cooled to −20° C., of benzyl (1S,5S)-6-(2,4-dimethoxybenzyl)-4,7-dioxo-2,6-diazabicyclo[3.2.0]-heptane-2-carboxylate (European Patent Application No. 508 234 discloses the corresponding 3,4-dimethoxybenzyl compound) in ethylene chloride (750 ml) was added in one portion. The reaction mixture was stirred for 1 hour at between −6 and −7° C., poured into 1N ice-cold aqueous hydrochloric acid (140 ml) and extracted with ethyl acetate (2×1 l). The combined organic phases were washed with saturated aqueous sodium chloride solution (1 l), dried over magnesium sulphate and concentrated. Yield: 76 g as a yellow oil, which was used in the next step without further purification.

IR (KBr): 1763, 1711, 1293, 1133, 1034, 838, 781 cm$^{-1}$; MS (ISP): (M+H)$^+$ 581.4.

d1) t-Butyl (1S,4R,5R)-4-[3-(t-butyl-dimethyl-silanyloxy)-2-oxo-propyl]-6-(2,4-dimethoxy-benzyl)-7-oxo-2,6-diaza-bicyclo[3.2.0]heptane-2-carboxylate The mixture of (Z)- and (E)-(1S,5R)-4-[3-(t-butyl-dimethyl-silanyloxy)-2-oxo-propylidene]-6-(2,4-dimethoxybenzyl)-7-oxo-2,6-diaza-bicyclo[3.2.0]heptane-2-carboxylate (76 g; maximal 73.8 mmol) prepared above was dissolved in methanol (900 ml), treated with di-t-butyl dicarbonate (24.4 ml; 112 mmol) and hydrogenated over 10% Pd/C (9 g). After 1.5 hours the reaction mixture was suction filtered, concentrated and chromatographed over silica gel (400 g; 0.063–0.2 mm particle size) with ethyl acetate/n-hexane 1:4. The solid residue obtained was triturated with n-hexane (200 ml) and suction filtered. Yield: 17 g (42%) as a colorless powder.

IR (KBr): 1760, 1740, 1688, 1613, 1365, 1261, 1161, 1035, 840, 780 cm$^{-1}$; MS (ISP): (M+H)$^+$ 549.5.

e1) t-Butyl (1S,4R,5R)-4-[3-(t-butyl-dimethyl-silanyloxy)-2-oxo-propyl]-7-oxo-2,6-diaza-bicyclo[3.2.0]heptane-2-carboxylate This compound was prepared in analogy to Example 1c) starting from t-butyl (1S,4R,5R)-4-[3-(t-butyl-dimethyl-silanyloxy)-2-oxo-propyl]-6-(2,4-dimethoxy-benzyl)-7-oxo-2,6-diaza-bicyclo[3.2.0]heptane-2-carboxylate (17 g; 31.0 mmol). The residue obtained was chromatographed over silica gel (400 g; 0.063–0.2 mm particle size) with ethyl acetate/n-hexane 7:3 and subsequently crystallized from n-hexane. Yield: 7.17 g (58%) as a colorless powder.

IR (KBr): 1772, 1740, 1700, 1257, 1164, 1107, 839, 780 cm$^{-1}$; MS (ISP): (M+H)$^+$ 399.5; (M+NH$_4$)$^+$ 416.5.

f1) Di-t-butyl (1aS,3aR,6bR)-5-(t-butyl-dimethyl-silanyloxy-methyl)-1-oxo-1a,2,3,3a,4,6b-hexahydro-1H-2,6a-diazacyclobut[cd]indene-2,6-dicarboxylate t-Butyl (1S,4R,5R)-4-[3-(t-butyl-dimethyl-silanyloxy)-2-oxo-propyl]-7-oxo-2,6-diaza-bicyclo[3.2.0]heptane-2-carboxylate (7.17 g; 18.0 mmol) and ethyl-diisopropylamine (3.7 ml; 21.6 mmol) were pre-cooled in abs. methylene chloride (70 ml) to 0° C. and added to a suspension of calcium carbonate (7.1 g; 71 mmol) and t-butyl-oxalyl chloride (3.55 g; 21.6 mmol) in abs. methylene chloride (50 ml) while cooling with an ice bath. After 1.5 hours at 0° C. the reaction mixture was diluted with methylene chloride (200 ml) and washed in succession with 1N ice-cold aqueous hydrochloric acid (100 ml), ice-cold water (2×100 ml) and ice-cold saturated aqueous sodium chloride solution (100 ml), dried over magnesium sulphate and concentrated. The residue was dissolved in abs. toluene (250 ml), treated at room temperature with triethyl phosphite (6.26 ml; 36 mmol) in abs. toluene (50 ml) and heated under reflux conditions for 15 hours. The reaction mixture was taken up in ethyl acetate (100 ml) and washed in succession with water (20 ml) and saturated aqueous sodium chloride solution (2×20 ml), dried over magnesium sulphate and concentrated. The solid residue was triturated with n-hexane (200 ml) and suction filtered. Yield: 5.61 g (63%) as a colorless powder.

IR (KBr): 1783, 1703, 1695, 1624, 1258, 1163, 1098, 838, 778 cm$^{-1}$; MS (EI): (M-$^t$BuO.) 421; Microanalysis: C$_{25}$H$_{42}$N$_2$O$_6$Si; Calc. C 60.70 H 8.56 N 5.66; Found C 60.59 H 8.76 N 5.49.

g1) Di-t-butyl (1aS,3aR,6bR)-5-hydroxymethyl-1-oxo-1a,2,3,3a,4,6b-hexahydro-1H-2,6a-diazacyclobut[cd]indene-2,6-dicarboxylate Di-t-butyl (1aS,3aR,6bR)-5-(t-butyl-dimethyl-silanyloxy-methyl)-1-oxo-1a,2,3,3a,4,6b-hexahydro-1H-2,6a-diazacyclo-but[cd]indene- 2,6-dicarboxylate (5.61 g; 11.34 mmol) was dissolved in tetrahydrofuran (80 ml) and treated at room temperature with 1N aqueous hydrochloric acid (23 ml). After 1 hour the reaction mixture was diluted with ethyl acetate (200 ml) and washed in succession with aqueous sodium bicarbonate solution (50 ml) and saturated aqueous sodium chloride solution (50 ml), dried over magnesium sulphate and concentrated. The residue was crystallized from n-hexane. Yield: 3.93 g (91%) as a colorless powder. M.p. 184° C.

IR (KBr): 1761, 1705, 1631, 1253, 1161, 1117, 1087cm$^{-1}$; MS (ISP): (M+H)$^+$ 381.4.

EXAMPLE 2

Scheme 1, (1)→(2),

Di-tert-butyl (1aS,3aR,6bR)-5-Formyl-1-oxo-1a,2,3,3a,4,6b-hexahydro-1H-2,6a-diaza-cyclobut[cd]indene-2,6-dicarboxylate

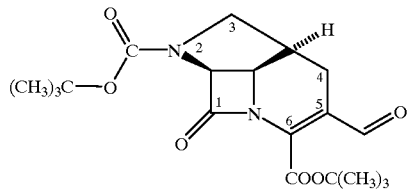

Di-tert-butyl (1aS,3aR,6bR)-5-hydroxymethyl-1-oxo-1a,2,3,3a,4,6b-hexahydro-1H-2,6a-diaza-cyclobut[cd]indene-2,6-dicarboxylate (Example 1) (1.14 g; 3 mmol) was dissolved in methylene chloride (30 ml) and cooled to 0° C. A solution of KBr (56 mg; 0.47 mmol) and sodium bicarbonate (126 mg; 1.5 mmol) in dist. water (12 ml) was added in one portion. Then, a solution of TEMPO (2,2,6,6-tetramethyl-piperidin-1-oxyl radical) (70 mg; 0.45 mmol) in methylene chloride (3 ml) was added dropwise in about 5 minutes while stirring well. Thereafter, 12 percent Javelle water (2.8 ml; 4.5 mmol) was added dropwise and the mixture was subsequently stirred for a further 2 hours at 0° C. The reaction mixture was poured into a separating funnel and diluted with methylene chloride (100 ml) and 100 ml of a saturated NaCl solution. The organic phase was separated and washed with 100 ml of a saturated NaCl solution. Both NaCl phases were back-extracted with methylene chloride (100 ml), the combined organic phases were dried over magnesium sulphate, suction filtered and concentrated. The product obtained was dried to constant weight in a vacuum.

Yield: 1.13 g (100%) as an orange-red powder. IR (KBr): 2760, 1789, 1711, 1672, 1602, 1248, 1162 cm$^{-1}$; MS (EI): 305 (M-tBuO.).

EXAMPLE 3

Scheme 1, Wittig Reaction (2)→(3): Method A in the Presence of NaH

Di-tert-butyl (E)-(1aS,3aR,6bR)-1-oxo-5-[2-oxo-1-(4-nitro-benzyl)-pyrrolidin-3-ylidenemethyl]-1a,2,3,3a,4,6b-hexahydro-1H-2,6a-diaza-cyclobut[cd]indene-2,6-dicarboxylate

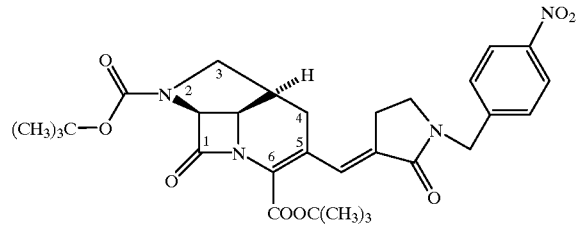

(RS)-[2-Oxo-1-(4-nitro-benzyl)-pyrrolidin-3-yl]-triphenyl-phosphonium bromide (202 mg; 0.36 mmol) was suspended in THF (3 ml), cooled to 0° C and treated with sodium hydride (13 mg; 0.33 mmol). Subsequently, the ice bath was removed and the mixture was stirred at room temperature for a further 30 minutes. The reaction mixture was again cooled to 0° C. and treated with 114 mg (0.3 mmol) of di-tert-butyl (1aS,3aR,6bR)-5-formyl-1-oxo-1a,2,3,3a,4,6b-hexahydro-1H-2,6a-diaza-cyclobut[cd]indene-2,6-dicarboxylate (Example 2) in ethylene chloride (9 ml).

After 30 minutes at 0° C. the mixture was stirred for 24 hours at room temperature. Thereafter, the reaction mixture was diluted with methylene chloride (20 ml), the organic phase was separated and washed with HCl 1N (10 ml) and twice with 10 ml of a saturated sodium chloride solution, dried over magnesium sulphate, suction filtered and concentrated. The residue obtained was chromatographed over silica gel (14 g, particle size 0.063–0.2 mm) with ethyl acetate.

Yield: 67 mg (39%) of a yellow, solid foam IR (KBr): 1775, 1701, 1 63S, 1522, 1346, 1246, 1661, 1030 cm$^{-1}$; MS (ISP): 581.4 (M+H)$^+$; 598.4 (M+NH$_4$)$^+$; 613.2 (M+H+CH$_3$OH)$^+$.

In analogy thereto there were prepared:

EXAMPLE 4

Di-tert-butyl (E)-(1aS,3aR,6bR)-1-oxo-5-[2-oxo-1-(thiophen-2-ylmethyl)-pyrrolidin-3-ylidenemethyl]-1a,2,3,3a,4,6b-hexahydro-1H-2,6a-diaza-cyclobut[cd]indene-2,6-dicarboxylate

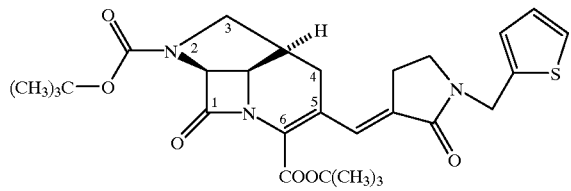

starting from 0.57 g (1.5 mmol) of di-tert-butyl (1aS,3aR,6bR)-5-formyl-1-oxo-1a,2,3,3a,4,6b-hexahydro-1H-2,6a-diaza-cyclobut-[cd]indene-2,6-dicarboxylate (Example 2) and (RS)-triphenyl-(1-thiophen-2-ylmethyl-2-oxo-pyrrolidin-3-yl)-phosphonium bromide (0.94 g; 1.8 mmol).

Yield: 277 mg (35%) as a colorless powder. IR (KBr): 1773, 1698, 1633, 1244, 1160 cm$^{-1}$; MS (ISP): 542.2 (M+H)$^+$.

EXAMPLE 5

Di-tert-butyl (E)-(1aS,3aR,6bR)-1-oxo-5-[1-isobutyl-2-oxo-pyrrolidin-3-ylidenemethyl]-1a,2,3,3a,4,6b-hexahydro-1H-2,6a-diaza-cyclobut[cd]indene-2,6-dicarboxylate

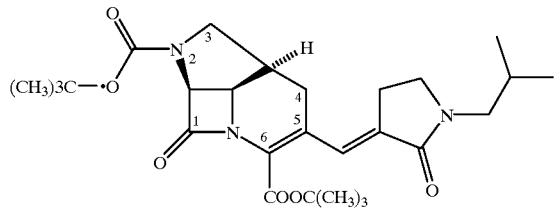

starting from 95 mg (0.25 mmol) of di-tert-butyl (1aS,3aR,6bR)-5-formyl-1-oxo-1a,2,3,3a,4,6b-hexahydro-1H-2,6a-diaza-cyclobut[cd]indene-2,6-dicarboxylate (Example 2) and (RS)-(1-isobutyl-2-oxo-pyrrolidin-3-yl)-triphenyl-phosphonium bromide (145 mg; 0.3 mmol).

Yield: 52 mg (42%) as a yellow resin IR (KBr): 1774, 1703, 1634, 1245, 1162 cm$^{-1}$; MS (ISP): 502.3 (M+H)$^+$; 519.3 (M+NH$_4$)$^+$.

EXAMPLE 6

Di-tert-butyl (E)-(1aS,3aR,6bR)-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-2,6-dicarboxylate

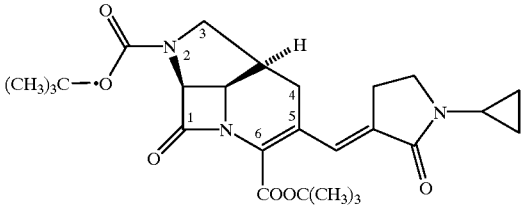

starting from 570 mg (1.5 mmol) of di-tert-butyl (1aS,3aR,6bR)-5-formyl-1-oxo-1a,2,3,3a,4,6b-hexahydro-1H-2,6a-diaza-cyclobut[cd]indene-2,6-dicarboxylate (Example 2) and (RS)-(1-cyclopropyl-2-oxo-pyrrolidin-3-yl)-triphenyl-phosphonium bromide 840 mg; 1.8 mmol).

Yield: 690 mg (95%) as a yellow powder. IR (KBr): 1773, 1700, 1634, 1438, 1367, 1190 cm$^{-1}$; MS (ISP): 486.4 (M+H)$^+$; 503.3 (M+NH$_4$)$^+$.

EXAMPLE 7

Di-tert-butyl (E)-(1aS,3aR,6bR)-1-oxo-5-[1-phenyl-2-oxo-pyrrolidin-3-ylidenemethyl]-1a,2,3,3a,4,6b-hexahydro-1H-2,6a-diaza-cyclobut[cd]indene-2,6-dicarboxylate

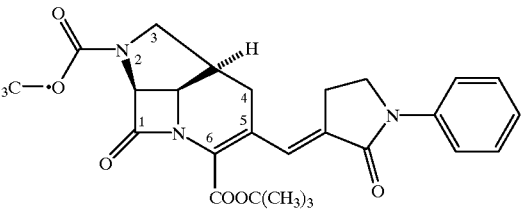

starting from 95 mg (0.25 mmol) of di-tert-butyl (1aS,3aR,6bR)-5-formyl-1-oxo-1a,2,3,3a,4,6b-hexahydro-1H-2,6a-diaza-cyclobut[cd]indene-2,6-dicarboxylate (Example 2) and (RS)-(1-phenyl-2-oxo-pyrrolidin-3-yl)-triphenyl-phosphonium bromide (138 mg; 0.3 mmol).

Yield: 38 mg (29%) as a yellow powder. IR (KBr): 1778, 1689, 1632, 1 597, 1495, 760, 692 cm$^{-1}$; MS (ISP): 522.2 (M+H)$^+$; 539.2 (M+NH$_4$)$^+$; 544.2 (M+Na)$^+$.

EXAMPLE 8

Di-tert-butyl (E)-(1aS,3aR,6bR)-1-oxo-5-[1-(1-ethoxycarbonyl-piperidin-4-yl)-2-oxo-pyrrolidin-3-ylidenemethyl]-1a,2,3,3a,4,6b-hexahydro-1H-2,6a-diaza-cyclobut[cd]indene-2,6-dicarboxylate

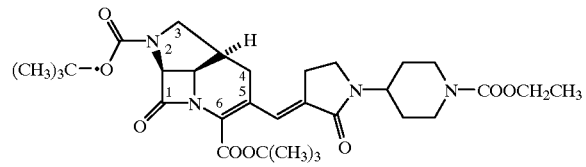

starting from 95 mg (0.25 mmol) of di-tert-butyl (1aS,3aR,6bR)-5-formyl-1-oxo-1a,2,3,3a,4,6b-hexahydro-1H-2,6a-diaza-cyclobut[cd]indene-2,6-dicarboxylate (Example 2) and (RS)-[1-(1-ethoxycarbonyl-piperidin-4-yl)-2-oxo-pyrrolidin-3-yl]-triphenyl-phosphonium bromide (174 mg; 0.3 mmol).

Yield: 64 mg (43%) as a yellow powder. IR (KBr): 1775, 1699, 1636, 1246, 1161 cm$^{-1}$; MS (ISP): 601.5 (M+H)$^+$; 618.5 (M+NH$_4$)$^+$; 623.5 (M+Na)$^+$.

EXAMPLE 9

Di-tert-butyl (E)-(1aS,3aR,6bR)-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-2,6-dicarboxylate

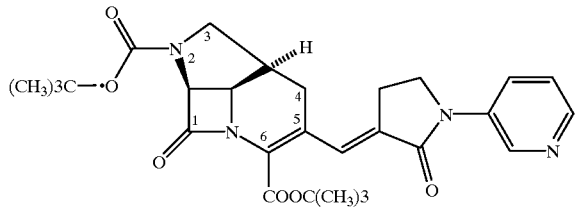

starting from 855 mg (2.25 mmol) of di-tert-butyl (1aS,3aR,6bR)-5-formyl-1-oxo-1a,2,3,3a,4,6b-hexahydro-1H-2,6a-diaza-cyclobut[cd]indene-2,6-dicarboxylate (Example 2) and (RS)-(2-oxo-1-pyridin-3-yl-pyrrolidin-3-yl)-triphenyl-phosphonium, bromide (1.36 g; 2.7 mmol).

Yield: 352 mg (30%) as a yellow powder. IR (KBr): 1769, 1705, 1628, 1250, 1160 cm$^{-1}$; MS (ISP): 523.2 (M+H)$^+$; 545.3 (M+Na)$^+$.

EXAMPLE 10

Scheme 1, Wittig reaction (2)→(3): method B in the presence of LiOH.

Di-tert-butyl (E)-(1aS,3aR,6bR)-1-oxo-5-[2-oxo-1-(4-tert-butoxycarbonyloxy-phenyl)-pyrrolidin-3-ylidenemethyl]-1a,2,3,3a,4,6b-hexahydro-1H-2,6a-diaza-cyclobut[cd]indene-2,6-dicarboxylate

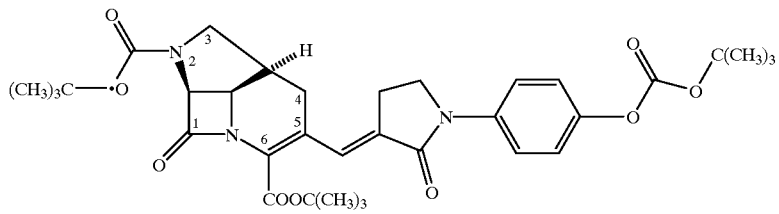

(RS)-[1-(4-tert-Butoxycarbonyloxy-phenyl)-2-oxo-pyrrolidin-3-yl]-triphenyl-phosphonium bromide (340 mg; 0.55 mmol) and 190 mg (0.5 mmol) of di-tert-butyl (1aS,3aR, 6bR)-5-formyl-1-oxo- 1a,2,3,3a,4,6b-hexahydro-1H-2,6a-diaza-cyclobut[cd]indene-2,6-dicarboxylate (Example 2) were suspended in methylene chloride (10 ml) and treated with molecular sieve 4 Å (1 g) and lithium hydroxide monohydrate (24 mg; 0.55 mmol). The mixture was stirred for 3 days at room temperature. Then, the suspended material was removed by filtration and the mother liquor was diluted with methylene chloride (about 100 ml), washed with a mixture of 1N HCl (10 ml) and a saturated sodium chloride solution (20 ml) and thereafter again washed with 2×30 ml of a saturated sodium chloride solution. The aqueous phases were back-extracted with methylene chloride (50 ml). The combined organic phases were dried over magnesium sulphate, suction filtered and concentrated. The brown residue was chromatographed over silica gel (60 g; particle size 0.063–0.2 mm) with ethyl acetate/hexane 2:1.

Yield: 44 mg (15%); IR (KBr): 1776, 1701, 1634, 1253, 1224, 1153 cm$^{-1}$; MS (ISP): 638.4 (M+H)$^+$; 655.4 (M+NH$_4$)$^+$.

In analogy thereto there was prepared:

EXAMPLE 11

Di-tert-butyl (E)-(1aS,3aR,6bR)-1-oxo-5-[1-(3-nitrophenyl)-2-oxo-pyrrolidin-3-ylidenemethyl]-1a,2,3,3a,4,6b-hexahydro-1H-2,6a-diaza-cyclobut[cd]indene-2,6-dicarboxylate

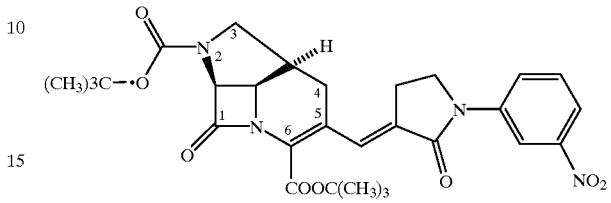

starting from di-tert-butyl (1aS,3aR,6bR)-5-formyl-1-oxo-1a,2,3,3a,4,6b-hexahydro-1H-2,6a-diaza-cyclobut[cd]indene-2,6-dicarboxylate (Example 2) (95 mg; 0.25 mmol) and (RS)-[1-(3-nitrophenyl)-2-oxo-pyrrolidin-3-yl]-triphenyl-phosphonium-bromide (151 mg; 0.275 mmol) at 80° C. in dichloroethane.

Yield: 47 mg (33%) as a yellow powder. IR (KBr): 1776, 1702, 1620, 1531, 1351 cm$^{-1}$; MS (ISP): 584.3 (M+NH$_4$)$^+$.

EXAMPLE 12

Scheme 1, Wittig reaction (2)→(3): method C in the presence of epoxybutane.

Di-tert-butyl (E)-(1aS,3aR,6bR)-1-oxo-5-[2-oxo-1-(2,2,2-trifluoro-ethyl)-pyrrolidin-3-ylidenemethyl]-1a,2,3,3a,4,6b-hexahydro-1H-2,6a-diaza-cyclobut[cd]indene-2,6-dicarboxylate

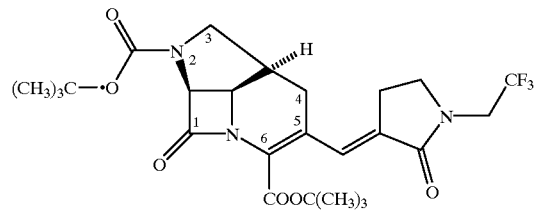

A suspension of di-tert-butyl (1aS,3aR,6bR)-5-formyl-1-oxo-1a,2,3,3a,4,6b-hexahydro-1H-2,6a-diaza-cyclobut[cd]indene-2,6-dicarboxylate (Example 2) (66 mg, 0.17 mmol) and rac-[2-oxo-1-(2,2,2-trifluoro-ethyl)-3-pyrrolidinyl]-triphenylphosphonium bromide (98 mg, 0.19 mmol, 1.1 eq.) in epoxybutane (8.5 ml) was heated under reflux under Ar for 3.5 hours. The resulting reaction solution was concentrated. The residue was taken up in methylene chloride (20 ml) and washed with saturated sodium chloride solution (2×10 ml). The aqueous phases were back-extracted with methylene chloride (20 ml). The combined organic phases, dried over MgSO$_4$, were concentrated and the oily residue was chromatographed twice on silica gel (eluent methylene chloride/acetone 19:1 and, respectively, tetrahydrofuran/hexane 2:3). After crystallization from tert-butyl methyl ether there were obtained 29 mg (31%) of di-tert-butyl (E)-(1aS,3aR,6bR)-1-oxo-5-[2-oxo-1-(2,2,2-trifluoroethyl)-pyrrolidin-3-ylidenemethyl]-1a,2,3,3a,4,6b-hexahydro-1H-2,6a-diaza-cyclobut[cd]indene-2,6-dicarboxylate as a white powder.

MS (ISP): 550.5 ((M+Na)$^+$, 10); 545.5 ((M+NH$_4$)$^+$, 100); 528.4 ((M+H)$^+$, 10). IR (KBr): 1773, 1705, 1634, 1265, 1159. Microanalysis: C$_{25}$H$_{32}$N$_3$O$_6$F$_3$; Calc. C 56.92, H 6.11, N 7.97, F 10.80; Found. C 56.97, H 6.43, N 7.59, F 10.32.

Removal of the protecting group, scheme 1, (3)→(4)

EXAMPLE 13

(E)-(1aS,3aR,6bR)-1-Oxo-5-[2-oxo-1-(4-hydroxyphenyl)-pyrrolidin-3-ylidenemethyl]-1a,2,3,3a,4,6b-hexahydro-1H-2,6a-diaza-cyclobut[cd]indene-6-carboxylic acid trifluoroacetate (1:0.8)

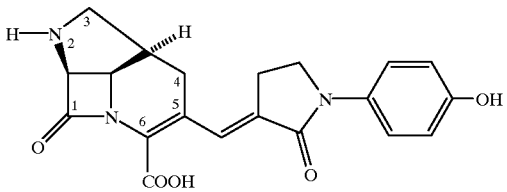

A solution of di-tert-butyl (E)-(1aS,3aR,6bR)-1-oxo-5-[2-oxo-1-(4-tert-butoxycarbonyloxy-phenyl)-pyrrolidin-3-ylidenemethyl]-1a,2,3,3a,4,6b-hexahydro-1H-2,6a-diaza-cyclobut[cd]indene-2,6-dicarboxylate (0.5 g; 0.784 mmol) (Example 10) in abs. methylene chloride (2 ml) was added dropwise to abs. trifluoroacetic acid (8 ml) at a temperature between (−20)° C. and (−18)° C. After 2 hours at this temperature the solution was diluted with methylene chloride (14 ml) and stirred for a further 2 hours at room temperature. The reaction mixture was concentrated. The residue was triturated with abs. ether (100 ml), filtered off under suction and washed with ether (2×20 ml). The crystals were dried for 10 hours in a high vacuum.

Yield: 0.35 g (94%) as a yellow powder. IR (KBr): 2640, 1775, 1677, 1628, 1402, 1280, 1205, 836 cm$^{-1}$; MS (ISP): 404.4 (M+Na)$^+$; 426.4 (M+2Na-H)$^+$.

In analogy thereto there were prepared:

EXAMPLE 14

(E)-(1aS,3aR,6bR)-1-Oxo-5-[2-oxo-1-(2,2,2-trifluoroethyl)-pyrrolidin-3-ylidenemethyl]-1a,2,3,3a,4,6b-hexahydro-1H-2,6a-diaza-cyclobut[cd]indene-6-carboxylic acid trifluoroacetate (1:1)

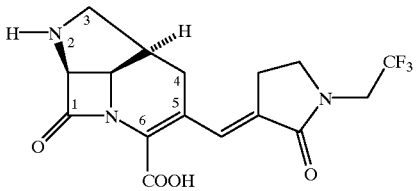

Starting from di-tert-butyl (E)-(1aS,3aR,6bR)-1-oxo-5-[2-oxo-1-(2,2,2-trifluoroethyl)-pyrrolidin-3-ylidenemethyl]-1a,2,3,3a,4,6b-hexahydro-1H-2,6a-diaza-cyclobut[cd]indene-2,6-dicarboxylate (Example 12) (160 mg, 0.30 mmol) there were obtained 121 mg (0.25 mmol, 82%) of (E)-(1aS,3aR,6bR)-1-oxo-5-[2-oxo-1-(2,2,2-trifluoroethyl)-pyrrolidin-3-ylidenemethyl]-1a,2,3,3a,4,6b-hexahydro-1H-2,6a-diaza-cyclobut[cd]indene-6-carboxylic acid trifluoroacetate (1:1) as a beige precipitate.

MS (ISN): 370.3 ((M−H)$^-$, 100). IR (KBr): 1779, 1686, 1635, 1396, 1151 cm$^{-1}$.

EXAMPLE 15

(E)-(1aS,3aR,6bR)-1-Oxo-5-[2-oxo-1-(4-nitrobenzyl)-pyrrolidin-3-ylidenemethyl]-1a,2,3,3a,4,6b-hexahydro-1H-2,6a-diaza-cyclobut[cd]indene-6-carboxylic acid trifluoroacetate (1:0.77)

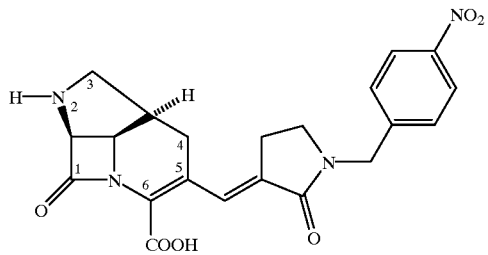

Starting from 212 mg (0.365 mmol) of di-tert-butyl (E)-(1aS,3aR,6bR)-1-oxo-5-[2-oxo-1-(4-nitro-benzyl)-pyrrolidin-3-ylidenemethyl]-1a,2,3,3a,4,6b-hexahydro-1H-2,6a-diaza-cyclobut[cd]indene-2,6-dicarboxylate (Example 3) there were obtained 158 mg (85%) of (E)-(1aS,3aR,6bR)-1-oxo-5-[2-oxo-1-(4-nitrobenzyl)-pyrrolidin-3-ylidenemethyl]-1a,2,3,3a,4,6b-hexahydro-1H-2,6a-diaza-cyclobut[cd]indene-6-carboxylic acid trifluoroacetate (1:0.77) as a brownish powder.

IR (KBr): 1775, 1678, 1610, 1521, 1415, 1347, 1202 cm$^{-1}$; MS (ISP): 425.2 (M+H)$^+$; 442.3 (M+NH$_4$)$^+$.

EXAMPLE 16

(E)-(1aS,3aR,6bR)-1-Oxo-5-[2-oxo-1-(thiophen-2-ylmethyl)-pyrrolidin-3-ylidenemethyl]-1a,2,3,3a,4,6b-hexahydro-1H-2,6a-diaza-cyclobut[cd]indene-6-carboxylic acid trifluoroacetate (1:0.75)

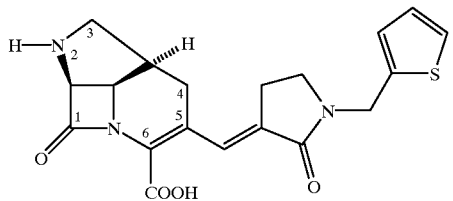

Starting from 250 mg (0.472 mmol) of di-tert-butyl (E)-(1aS,3aR,6bR)-1-oxo-5-[2-oxo-1-(thiophen-2-ylmethyl)-pyrrolidin-3-ylidenemethyl]-1a,2,3,3a,4,6b-hexahydro-1H-2,6a-diaza-cyclobut[cd]indene-2,6-dicarboxylate (Example 4) there were obtained 214 mg (96%) of (E)-(1aS,3aR,6bR)-1-oxo-5-[2-oxo-1-(thiophen-2-ylmethyl)-pyrrolidin-3-ylidenemethyl]-1a,2,3,3a,4,6b-hexahydro-1H-2,6a-diaza-cyclobut[cd]indene-6-carboxylic acid trifluoroacetate (1:0.75) as a yellow powder.

IR (KBr): 2798, 1774, 1678, 1631, 1428, 1203 cm$^{-1}$; MS (ISN): 383.9 (M−H)$^-$; 401.1 (M+NH$_3$−H).

EXAMPLE 17

(E)-(1aS,3aR,6bR)-1-Oxo-5-[1-(isobutyl)-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.7)

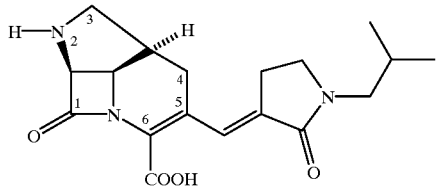

Starting from 250 mg (0.5 mmol) of di-tert-butyl (E)-(1aS,3aR,6bR)-1-oxo-5-[1-isobutyl-2-oxo-pyrrolidin-3-ylidenemethyl]-1a,2,3,3a,4,6b-hexahydro-1H-2,6a-diaza-cyclobut[cd]-indene-2,6-dicarboxylate (Example 5) there were obtained 218 mg (88%) of (E)-(1aS,3aR,6bR)-1-oxo-5-[1-(isobutyl)-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.7) as a brownish powder.

IR (KBr): 1775, 1677, 1632, 1202 cm$^{-1}$; MS (ISP): 346.3 (M+H)$^+$.

EXAMPLE 18

(E)-(1aS,3aR,6bR)-1-Oxo-5-[1-(3-nitrophenyl)-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.7)

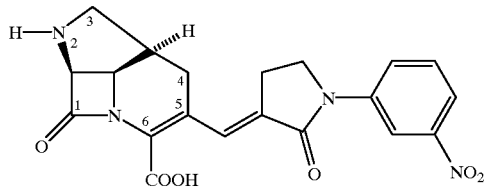

Starting from 460 mg (0.81 mmol) of di-tert-butyl (E)-(1aS,3aR,6bR)-1-oxo-5-[1-(3-nitro-phenyl)-2-oxo-pyrrolidin-3-ylidenemethyl]-1a,2,3,3a,4,6b-hexahydro-1H-2,6a-diaza-cyclobut[cd]indene-2,6-dicarboxylate (Example 11) (460 mg; 0.81 mmol) there were obtained 280 mg (71%) of (E)-(1aS,3aR, 6bR)-1-oxo-5-[1-(3-nitrophenyl)-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.7) as a yellow powder.

IR (KBr): 1774, 1678, 1630, 1527, 1387, 1212 cm$^{-1}$; MS (ISP): 411.3 (M+H)$^+$.

EXAMPLE 19

(E)-(1aS,3aR,6bR)-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.82)

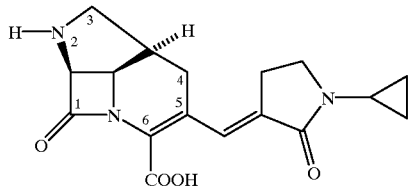

Starting from 690 mg (1.4 mmol) of di-tert-butyl (E)-(1aS,3aR,6bR)-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-2,6-dicarboxylate (Example 6) there were obtained 355 mg (59%) of (E)-(1aS,3aR,6bR)-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.82) as a beige powder.

IR (KBr): 1777, 1678, 1632, 1425, 1199 cm$^{-1}$; MS (ISP): 330.3 (M+H)$^+$; 347.3 (M+NH$_4$)$^+$; 352.3 (M+Na)$^+$.

EXAMPLE 20

(E)-(1aS,3aR,6bR)-1-Oxo-5-[2-oxo-1-phenyl-pyrrolidin-3-ylidenemethyl]-1a,2,3,3a,4,6b-hexahydro-1H-2,6a-diaza-cyclobut[cd]indene-6-carboxylic acid trifluoroacetate (1:0.77)

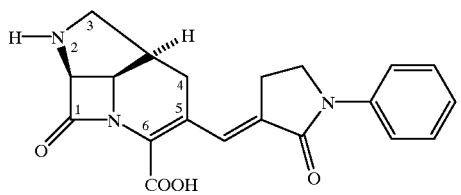

Starting from 255 mg (0.49 mmol) of di-tert-butyl (E)-(1aS,3aR,6bR)-1-oxo-5-[1-phenyl-2-oxo-pyrrolidin-3-ylidenemethyl]-1a,2,3,3a,4,6b-hexahydro-1H-2,6a-diaza-cyclobut[cd]-indene-2,6-dicarboxylate (Example 7) there were obtained 215 mg (97%) of (E)-(1aS,3aR,6bR)-1-oxo-5-[2-oxo-1-phenyl-pyrrolidin-3-ylidenemethyl]-1a,2,3,3a,4,6b-hexahydro-1H-2,6a-diaza-cyclobut[cd]indene-6-carboxylic acid trifluoroacetate (1:0.77) as a beige powder.

IR (KBr): 3435, 2933, 1771, 1679, 1628, 1597, 1496, 1397, 1206 cm$^{-1}$; MS (ISP): 366.2 (M+H)$^+$; 388.2 (M+Na)$^+$.

EXAMPLE 21

(E)-(1aS,3aR,6bR)-1-Oxo-5-[1-(1-ethoxycarbonyl-piperidin-4-yl)-2-oxo-pyrrolidin-3-ylidenemethyl]-1a,2,3, 3a,4, 6b-hexahydro-1H-2,6a-diaza-cyclobut[cd]indene-6-carboxylic acid trifluoroacetate (1:0.73)

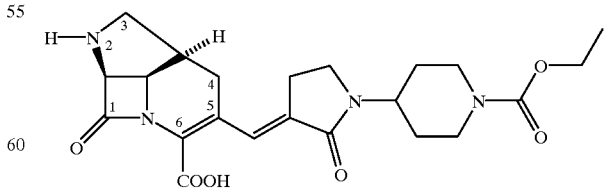

Starting from 418 mg (0.696 mmol) of di-tert-butyl (E)-(1aS,3aR,6bR)-1-oxo-5-[1-(1-ethoxycarbonyl-piperidin-4-yl)-2-oxo-pyrrolidin-3-ylidenemethyl]-1a,2,3,3a,4,6b-hexahydro-1H-2,6a-diaza-cyclobut[cd]indene-2,6- dicarboxylate (Example 8) there were obtained 310 mg (84%) of (E)-(1aS,3aR,6bR)-1-oxo-5-[1-(1-ethoxycarbonyl-piperidin-4-yl)-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.73) as a beige powder.

IR (KBr): 3433, 1773, 1685, 1630, 1279, 1206 cm$^{-1}$; MS (ISP): 445.5 (M+H)$^+$; 462.4 (M+NH$_4$)$^+$; 467.2 (M+Na)$^+$.

EXAMPLE 22

(E)-(1aS,3aR,6bR)-1-Oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-6-carboxylic acid trifluoroacetate (1:1.4)

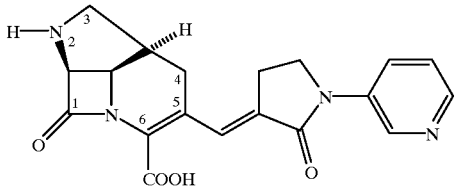

Starting from 262 mg (0.5 mmol) of di-tert-butyl (E)-(1aS,3aR,6bR)-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-2,6-dicarboxylate (Example 9) there were obtained 263 mg (100%) of (E)-(1aS,3aR,6bR)-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-6-carboxylic acid trifluoroacetate (1:1,4) as a yellow powder.

IR (KBr): 1775, 1682, 1627, 1555, 1394, 1205 cm$^{-1}$; MS (ISN): 365.2 (M–H)$^-$.

Acylation, Scheme 1, (4)→(5)

EXAMPLE 23

(E)-(1aS,3aR,6bR)-2-(4-Carbamoyl-phenylcarbamoyl)-1-oxo-5-[2-oxo-1-(2,2,2-trifluoroethyl)-pyrrolidin-3-ylidenemethyl]-1a,2,3,3a,4,6b-hexahydro-1H-2,6a-diaza-cyclobut[cd]indene-6-carboxylic acid sodium salt (1:1)

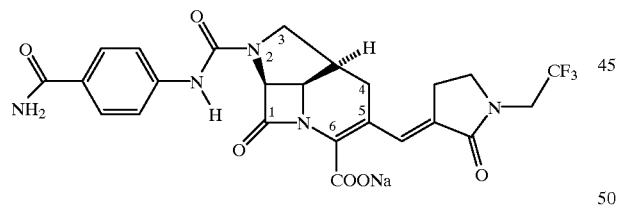

48 mg, 0.10 mmol of (E)-(1aS,3aR,6bR)-1-oxo-5-[2-oxo-1-(2,2,2-trifluoroethyl)-pyrrolidin-3-ylidenemethyl]-1a,2,3,3a, 4,6b-hexahydro-1H-2,6a-diaza-cyclobut[cd]indene-6-carboxylic acid trifluoroacetate (1:1) (Example 14) were placed in aceto-nitrile/water 1:1 (2 ml) and cooled to 0° C. The solution was treated with sodium bicarbonate (16 mg; 0.2 mmol) and 2,5-dioxo-pyrrolidin-1-yl 4-carbamoyl-phenylcarbamate (30 mg, 0.11 mmol). The mixture was stirred for 10 minutes at 0° C. Then, it was stirred for a further 1 to 2 hours at room temperature. The reaction mixture was subsequently diluted with water (2 ml), washed with methylene chloride (3×3 ml) and lyophilized. The residue was dissolved in a small amount of water and chromatographed over a polymeric hydrophobic gel with water and lyophilized. Yield: 34 mg (61%) as a yellowish lyophilizate.

MS (ISP): 556.4 ((M+H)$^+$, 45); 551.5 ((M–Na+H+NH$_4$)$^+$, 70); 534.5 ((M–Na+2H)$^+$, 100). IR (KBr): 3429, 1753, 1663, 1605, 1525, 1389, 1152.

EXAMPLE 24

(E)-(1aS,3aR,6bR)-2-Acetyl-1-oxo-5-[2-oxo-1-(4-hydroxyphenyl)-pyrrolidin-3-ylidenemethyl]-1a,2,3,3a,4,6b-hexahydro-1H-2,6a-diaza-cyclobut[cd]indene-6-carboxylic acid sodium salt (1:1)

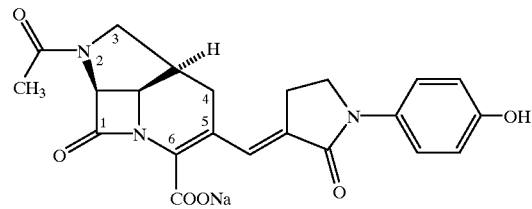

Acetyl chloride (59 µl; 0.81 mmol) was added to a solution of 0.32 g; 0.675 mmol of (E)-(1aS,3aR,6bR)-1-oxo-5-[2-oxo-1-(4-hydroxyphenyl)-pyrrolidin-3-ylidenemethyl]-1a,2,3,3a,4,6b-hexahydro-1H-2,6a-diaza-cyclobut[cd]indene-6-carboxylic acid trifluoroacetate (1:0.8) (Example 13) and sodium hydrogen carbonate (181 mg; 2.16 mmol) in DMF (8 ml) at (–10)° C. The reaction mixture was stirred at (–10)° C. for 2.5 hours and then concentrated. The residue was dissolved in a small amount of water and chromatographed over a polymeric hydrophobic gel (eluent: water/acetonitrile). There were obtained 113 mg (38%) of (E)-(1aS,3aR,6bR)-2-acetyl-1-oxo-5-[2-oxo-1-(4-hydroxyphenyl)-pyrrolidin-3-ylidenemethyl]-1a,2,3,3a, 4,6b-hexahydro- 1H-2,6a-diaza-cyclobut[cd]indene-6-carboxylic acid sodium salt (1:1) as] a yellowish powder.

IR (KBr): 1752, 1621, 1393, 837 cm$^{-1}$; MS (ISP): 468.2 (M+H)$^+$.

In analogy thereto there were prepared:

EXAMPLE 25

(E)-(1aS,3aR,6bR)-2-Acetyl-1-oxo-5-[2-oxo-1-(2,2,2-trifluoroethyl)-pyrrolidin-3-ylidenemethyl]-1a,2,3,3a,4,6b-hexahydro-1H-2,6a-diaza-cyclobut[cd]indene-6-carboxylic acid sodium salt (1:1)

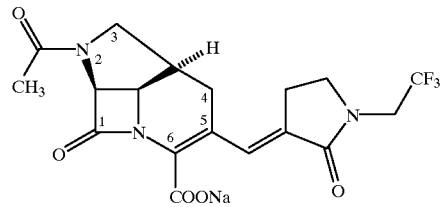

Starting from 80 mg (0.165 mmol) of (E)-(1aS,3aR,6bR)-1-oxo-5-[2-oxo-1-(2,2,2-trifluoroethyl)-pyrrolidin-3-ylidenemethyl]-1a,2,3,3a,4,6b-hexahydro-1H-2,6a-diaza-cyclobut[cd]indene-6-carboxylic acid trifluoroacetate (1:1) (Example 14) and acetyl chloride (12 µl, 0.165 mmol) there were obtained 29 mg (40%) of (E)-(1aS,3aR,6bR)-2-acetyl-1-oxo-5-[2-oxo-1-(2,2,2-trifluoroethyl)-pyrrolidin-3-ylidenemethyl]-1a,2,3,3a,4,6b-hexahydro-1H-2,6a-diaza-cyclobut[cd]indene-6-carboxylic acid sodium salt (1:1) as a yellowish lyophilizate.

IR (KBr): 1756, 1690, 1623, 1395, 1151 cm$^{-1}$; MS (ISN): 429.5 (M–Na+NH$_3$)$^-$; 412.4 (M–Na)$^-$.

EXAMPLE 26

(E)-(1aS,3aR,6bR)-2-Acetyl-1-oxo-5-[2-oxo-1-(4-nitrobenzyl)-pyrrolidin-3-ylidenemethyl]-1a,2,3,3a,4,6b-hexahydro-1H-2,6a-diaza-cyclobut[cd]indene-6-carboxylic acid sodium salt (1:1)

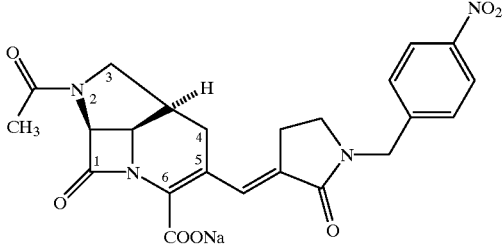

Starting from 122 mg (0.238 mmol) of (E)-(1aS,3aR,6bR)-1-oxo-5-[2-oxo-1-(4-nitrobenzyl)-pyrrolidin-3-ylidenemethyl]-1a,2,3,3a,4,6b-hexahydro-1H-2,6a-diaza-cyclobut[cd]indene-6-carboxylic acid trifluoroacetate (1:0.77) (Example 15) and acetyl chloride (21 µl, 0.286 mmol) there were obtained 61 mg (53%) of (E)-(1aS,3aR,6bR)-2-acetyl-1-oxo-5-[2-oxo-1-(4-nitrobenzyl)-pyrrolidin-3-ylidenemethyl]-1a,2,3,3a,4,6b-hexahydro-1H-2,6a-diaza-cyclobut[cd]indene-6-carboxylic acid sodium salt (1:1) as a reddish lyophilizate.

IR (KBr): 1752, 1626, 1520, 1394, 1345 cm$^{-1}$. MS (ISP): 467.3 (M+H)$^+$; 484.2 (M+NH$_4$)$^+$; 489.2 (M+Na)$^+$.

EXAMPLE 27

(E)-(1aS,3aR,6bR)-2-Acetyl-1-oxo-5-[2-oxo-1-(thiophen-2-ylmethyl)-pyrrolidin-3-ylidenemethyl]-1a,2,3,3a,4,6b-hexahydro-1H-2,6a-diaza-cyclobut[cd]indene-6-carboxylic acid sodium salt (1:1)

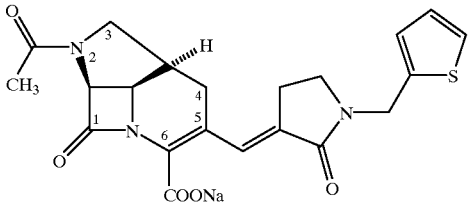

Starting from 80 mg (0.17 mmol) of (E)-(1aS,3aR,6bR)-1-oxo-5-[2-oxo-1-(thiophen-2-ylmethyl)-pyrrolidin-3-ylidenemethyl]-1a,2,3,3a,4,6b-hexahydro-1H-2,6a-diaza-cyclobut[cd]indene-6-carboxylic acid trifluoroacetate (1:0.75) (Example 16) and acetyl chloride (15 µl, 0.204 mmol) there were obtained 50 mg (65%) of (E)-(1aS,3aR,6bR)-2-acetyl-1-oxo-5-[2-oxo-1-(thiophen-2-ylmethyl)-pyrrolidin-3-ylidenemethyl]-1a,2,3,3a, 4,6b-hexahydro-1H-2,6a-diaza-cyclobut[cd]indene-6-carboxylic acid sodium salt (1:1) as a yellow lyophilizate.

IR (KBr): 1753, 1624, 1395 cm$^{-1}$. MS (ISP): 428.4 (M+H)$^+$; 445.4 (M+NH$_4$)$^+$; 450.4 (M+Na)$^+$.

EXAMPLE 28

(E)-(1aS,3aR,6bR)-2-Acetyl-1-oxo-5-[2-oxo-1-isobutyl-pyrrolidin-3-ylidenemethyl]-1a,2,3,3a,4,6b-hexahydro-1H-2,6a-diaza-cyclobut[cd]indene-6-carboxylic acid sodium salt (1:1)

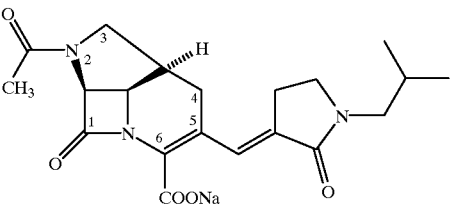

Starting from 142 mg (0.334 mmol) of (E)-(1aS,3aR,6bR)-1-oxo-5-[1-(Isobutyl)-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.7) (Example 17) and acetyl chloride (30 µl, 0.4 mmol) there were obtained 63 mg (46%) of (E)-(1aS,3aR,6bR)-2-acetyl-1-oxo-5-[2-oxo-1-isobutyl-pyrrolidin-3-ylidenemethyl]-1a,2,3,3a,4,6b-hexahydro-1H-2,6a-diaza-cyclobut[cd]indene-6-carboxylic acid sodium salt (1:1) as a reddish lyophilizate.

IR (KBr): 1753, 1625, 1392 cm$^{-1}$. MS (ISP): 388.2 (M+H)$^+$; 405.3 (M+NH$_4$)$^+$; 410.3 (M+Na)$^+$.

EXAMPLE 29

(E)-(1aS,3aR,6bR)-2-Acetyl-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-6-carboxylic acid sodium salt (1:1)

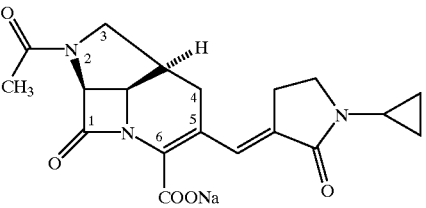

Starting from 150 mg (0.355 mmol) of (E)-(1aS,3aR,6bR)-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.82) (Example 19) and acetyl chloride (32 µl, 0.426 mmol) there were obtained 49 mg (35%) of (E)-(1aS,3aR,6bR)-2-acetyl-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-6-carboxylic acid sodium salt (1:1) as an orange powder.

IR (KBr): 1754, 1624, 1392 cm$^{-1}$. MS (ISP): 372.2 (M+H)$^+$; 389.2 (M+NH$_4$)$^+$; 394.2 (M+Na)$^+$.

EXAMPLE 30

(E)-(1aS,3aR,6bR)-2-Acetyl-1-oxo-5-[1-(3-nitrophenyl)-2-oxo-pyrrolidin-3-ylidenemethyl]-1a,2,3,3a,4,6b-hexahydro-1H-2,6a-diaza-cyclobut[cd]indene-6-carboxylic acid sodium salt (1:1)

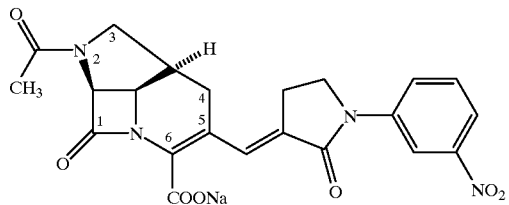

Starting from 130 mg (0.265 mmol) of (E)-(1aS,3aR,6bR)-1-oxo-5-[1-(3-nitrophenyl)-2-oxo-pyrrolidin-3-ylidenemethyl]-1a,2,3,3a,4,6b-hexahydro-1H-2,6a-diazacyclobut[cd]indene-6-carboxylic acid trifluoroacetate (1:0.7) (Example 18) and acetyl chloride (24 µl, 0.318 mmol) there were obtained 73 mg (58%) of (E)-(1aS,3aR,6bR)-2-acetyl-1-oxo-5-[1-(3-nitrophenyl)-2-oxo-pyrrolidin-3-ylidenemethyl]-1a,2,3,3a,4,6b-hexahydro-1H-2,6a-diazacyclobut[cd]indene-6-carboxylic acid sodium salt (1:1) as a yellow powder.

IR (KBr): 1756, 1680, 1617, 1528, 1390, 1347 cm$^{-1}$. MS (ISN): 468.2 (M−Na+NH$_3$)$^-$.

EXAMPLE 31

(E)-(1aS,3aR,6bR)-2-Acetyl-1-oxo-5-[2-oxo-1-phenyl-pyrrolidin-3-ylidenemethyl]-1a,2,3,3a,4,6b-hexahydro-1H-2,6a-diaza-cyclobut[cd]indene-6-carboxylic acid sodium salt (1:1)

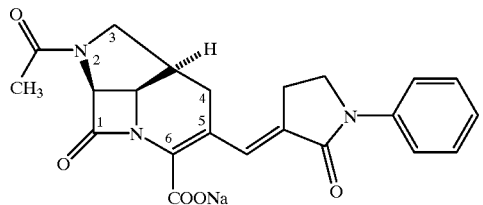

Starting from 91 mg (0.2 mmol) of (E)-(1aS,3aR,6bR)-1-oxo-5-[2-oxo-1-phenyl-pyrrolidin-3-ylidenemethyl]-1a,2,3,3a,4,6b-hexahydro-1H-2,6a-diaza-cyclobut[cd]indene-6-carboxylic acid trifluoroacetate (1:0.77) (Example 20) and acetyl chloride (18 µl, 0.24 mmol) there were obtained 41 mg (48%) of (E)-(1aS,3aR,6bR)-2-acetyl-1-oxo-5-[2-oxo-1-phenyl-pyrrolidin-3-ylidenemethyl]-1a,2,3,3a,4,6b-hexahydro-1H-2,6a-diaza-cyclobut[cd]indene-6-carboxylic acid sodium salt (1:1) as a yellow powder.

IR (KBr): 1751, 1670, 1622, 1600, 1391 cm$^{-1}$. MS (ISP): 408.3 (M−Na+2H)$^+$; 425.5 (M−Na+H+NH$_4$)$^+$; 430.4 (M+H)$^+$.

EXAMPLE 32

(E)-(1aS,3aR,6bR)-2-Acetyl-1-oxo-5-[1-(1-ethoxycarbonyl-piperidin-4-yl)-2-oxo-pyrrolidin-3-ylidenemethyl]-1a,2,3,3a,4,6b-hexahydro-1H-2,6a-diazacyclobut[cd]indene-6-carboxylic acid sodium salt (1:1)

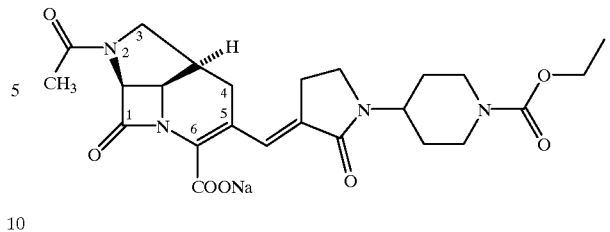

Starting from 107 mg (0.2 mmol) of (E)-(1aS,3aR,6bR)-1-oxo-5-[1-(1-ethoxycarbonyl-piperidin-4-yl)-2-oxo-pyrrolidin-3-ylidenemethyl]-1a,2,3,3a,4,6b-hexahydro-1H-2,6a-diazacyclobut[cd]indene-6-carboxylic acid trifluoroacetate (1:0.73) (Example 21) and acetyl chloride (18 µl, 0.24 mmol) there were obtained 60 mg (59%) of (E)-(1aS,3aR,6bR)-2-acetyl-1-oxo-5-[1-(1-ethoxycarbonyl-piperidin-4-yl)-2-oxo-pyrrolidin-3-ylidenemethyl]-1a,2,3,3a,4,6b-hexahydro-1H-2,6a-diaza-cyclobut[cd]indene-6-carboxylic acid sodium salt (1:1) as a red powder.

IR (KBr): 1756, 1690, 1625, 1600, 1386, 1212 cm$^{-1}$. MS (ISP): 487.2 (M−Na+2H)$^+$; 504.2 (M−Na+H+NH$_4$)$^+$; 509.1 (M+H)$^+$.

EXAMPLE 33

(E)-(1aS,3aR,6bR)-2-Acetyl-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-6-carboxylic acid sodium salt (1:1)

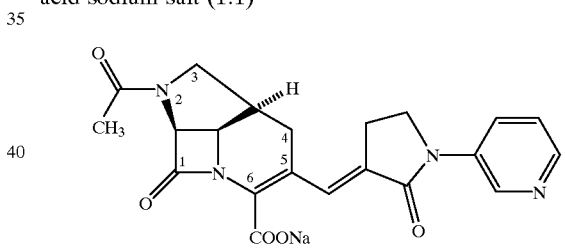

Starting from 108 mg (0.2 mmol) of (E)-(1aS,3aR,6bR)-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-6-carboxylic acid trifluoroacetate (1:1.4) (Example 22) and acetyl chloride (18 µl, 0.24 mmol) there were obtained 58 mg (67%) of (E)-(1aS,3aR,6bR)-2-acetyl-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-6-carboxylic acid sodium salt (1:1) as a yellow powder.

IR (KBr): 1754, 1680, 1623, 1387 cm$^{-1}$. MS (ISP): 409.3 (M+H)$^+$; 431.4 (M+Na)$^+$.

EXAMPLE 34

(E)-(1aS,3aR,6bR)-1-Oxo-5-[2-oxo-1-(3-nitro-phenyl)-pyrrolidin-3-ylidenemethyl]-2-trifluoroacetyl-1a,2,3,3a,4,6b-hexahydro-1H-2,6a-diaza-cyclobut[cd]indene-6-carboxylic acid sodium salt (1:1)

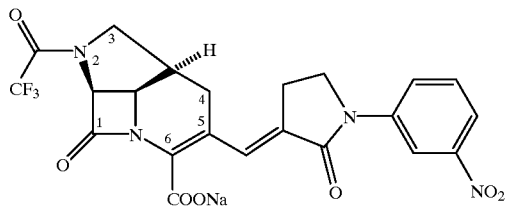

A solution of 135 mg (0.275 mmol) of (E)-(1aS,3aR,6bR)-1-oxo-5-[2-oxo-1-(3-nitrophenyl)-pyrrolidin-3-ylidenemethyl]-1a,2,3,3a,4,6b-hexahydro-1H-2,6a-diaza-cyclobut[cd]indene-6-carboxylic acid trifluoroacetate (Example 18) in DMF (3 ml) was treated with concentrated trifluoroacetic acid (21 µl; 0.275 mmol) and dicyclohexyl-carbodiimide (67 mg; 0.324 mmol) and stirred for 1hour at room temperature. Subsequently, the reaction mixture was suction filtered, the mother liquor was evaporated and the residue was treated with water (4 ml). The pH value was adjusted to 7.5 with a saturated sodium hydrogen carbonate solution and the solution obtained was chromatographed over a hydrophobic polymer.

Yield: 64 mg (44%) as a yellow powder. IR (KBr): 1764, 1691, 1614, 1529, 1483, 1390, 1347, 1214, 1151 cm$^{-1}$; MS (ISN): 522.0 (M−Na+NH$_3$)$^-$.

In analogy thereto there were prepared:

EXAMPLE 35

(E)-(1aS,3aR,6bR)-1-Oxo-5-[2-oxo-1-(thiophen-2-ylmethyl)-pyrrolidin-3-ylidenemethyl]-2-trifluoroacetyl-1a,2,3,3a,4,6b-hexahydro-1H-2,6a-diaza-cyclobut[cd]indene-6-carboxylic acid sodium salt (1:1)

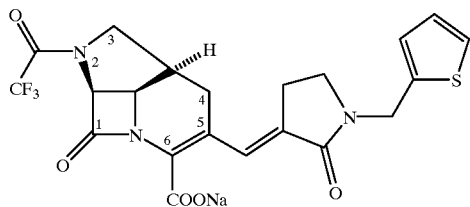

Starting from 80 mg (0.17 mmol) of (E)-(1aS,3aR,6bR)-1-oxo-5-[2-oxo-1-(thiophen-2-ylmethyl)-pyrrolidin-3-ylidenemethyl]-1a,2,3,3a,4,6b-hexahydro-1H-2,6a-diaza-cyclobut[cd]indene-6-carboxylic acid trifluoroacetate (1:0.75) (Example 16) there were obtained 36 mg (42%) of (E)-(1aS,3aR,6bR)-1-oxo-5-[2-oxo-1-(thiophen-2-ylmethyl)-pyrrolidin-3-ylidenemethyl]-2-trifluoroacetyl-1a,2,3,3a,4,6b-hexahydro-1H-2,6a-diaza-cyclobut[cd]indene-6-carboxylic acid sodium salt (1:1) as a yellow powder.

IR (KBr): 1763, 1691, 1618, 1393, 1366, 1153 cm$^{-1}$; MS (ISP): 482.2 (M+H)$^+$; 504.1 (M+Na)$^+$.

EXAMPLE 36

(E)-(1aS,3aR,6bR)-1-Oxo-5-[2-oxo-1-cyclopropyl-pyrrolidin-3-ylidenemethyl]-2-trifluoroacetyl-1a,2,3,3a,4,6b-hexahydro-1H-2,6a-diaza-cyclobut[cd]indene-6-carboxylic acid sodium salt (1:1)

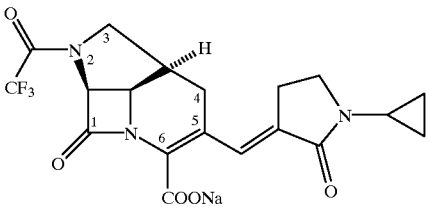

Starting from 164 mg (0.387 mmol) of (E)-(1aS,3aR,6bR)-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-6-carboxylic acid trifluoroacetate (1:0.82) (Example 19) there were obtained 72 mg (42%) of (E)-(1aS,3aR,6bR)-1-oxo-5-[2-oxo-1-cyclopropyl-pyrrolidin-3-ylidenemethyl]-2-trifluoroacetyl-1a,2,3,3a,4,6b-hexahydro-1H-2,6a-diaza-cyclobut[cd]indene-6-carboxylic acid sodium salt (1:1) as a beige powder.

IR (KBr): 1764, 1693, 1620, 1393, 1178, 1152 cm$^{-1}$; MS (ISP): 426.4 (M+H)$^+$; 448.4 (M+Na)$^+$.

EXAMPLE 37

(E)-(1aS,3aR,6bR)-1-Oxo-5-[2-oxo-1-phenyl-pyrrolidin-3-ylidenemethyl]-2-trifluoroacetyl-1a,2,3,3a,4,6b-hexahydro-1H-2,6a-diaza-cyclobut[cd]indene-6-carboxylic acid sodium salt (1:1)

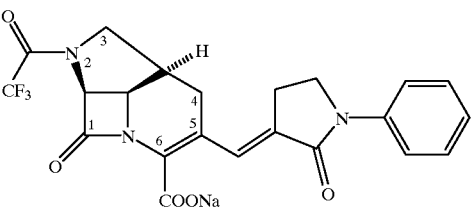

Starting from 86 mg (0.189 mmol) of (E)-(1aS,3aR,6bR)-1-oxo-5-[2-oxo-1-phenyl-pyrrolidin-3-ylidenemethyl]-1a,2,3,3a,4,6b-hexahydro-1H-2,6a-diaza-cyclobut[cd]indene-6-carboxylic acid trifluoroacetate (1:0.77) (Example 20) there were obtained 34 mg (38%) of (E)-(1aS,3aR,6bR)-1-oxo-5-[2-oxo-1-phenyl-pyrrolidin- 3-ylidenemethyl]-2-trifluoroacetyl-1a,2,3,3a,4,6b-hexahydro-1H-2,6a-diaza-cyclobut[cd]indene-6-carboxylic acid sodium salt (1:1) as a yellow powder.

IR (KBr): 1760, 1690, 1616, 1600, 1391, 1180, 760, 700 cm$^{-1}$; MS (ISP): 462.3 (M−Na+2H)$^+$; 484.2 (M+H)$^+$.

EXAMPLE 38

(E)-(1aS,3aR,6bR)-1-Oxo-5-[2-oxo-1-pyridin-3-yl-pyrrolidin-3-ylidenemethyl]-2-trifluoroacetyl-1a,2,3,3a,4,6b-hexahydro-1H-2,6a-diaza-cyclobut[cd]indene-6-carboxylic acid sodium salt (1:1)

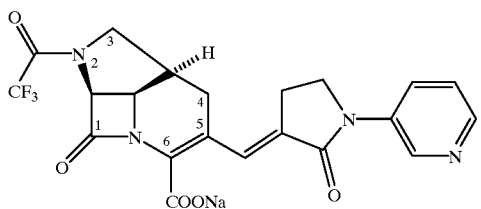

Starting from 108 mg (0.2 mmol) of (E)-(1aS,3aR,6bR)-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-6-carboxylic acid trifluoroacetate (1:1.4) (Example 22) there were obtained 52 mg (54%) of (E)-(1aS,3aR,6bR)-1-oxo-5-[2-oxo-1-pyridin-3-yl-pyrrolidin-3-ylidenemethyl]-2-trifluoroacetyl-1a,2,3,3a,4,6b-hexahydro-1H-2,6a-diaza-cyclobut[cd]indene-6-carboxylic acid sodium salt (1:1) as a yellow powder.

IR (KBr): 1766, 1690, 1616, 1600, 1485, 1388, 1179 cm$^{-1}$; MS (ISN): 478.1 (M+NH$_3$–Na)$^-$.

Quaternisation, Scheme 1, (5)→(6)

EXAMPLE 39

(E)-(1aS,3aR,6bR)-2-Acetyl-5-[1-(1-benzyl-pyridin-1-ium-3-yl)-2-oxo-pyrrolidin-3-ylidenemethyl]-1-oxo-1a,2,3,3a,4,6b-hexahydro-1H-2,6a-diaza-cyclobut[cd]indene-6-carboxylate acid

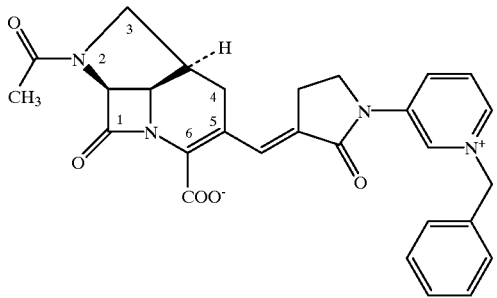

75 mg (0.174 mmol) of (E)-(1aS,3aR,6bR)-2-acetyl-1-oxo-5-[2-oxo-1-(3-pyridinyl)-pyrrolidin-3-ylidenemethyl]-1a,2,3,3a,4,6b-hexahydro-1H-2,6a-diaza-cyclobut[cd]indene-6-carboxylic acid sodium salt (1:1) (Example 33) were dissolved in dimethylformamide (1.5 ml) and treated with a 0.142 molar trifluoroacetic acid solution in DMF (1.23 ml; 0.174 mmol). After stirring for 10 minutes at room temperature benzyl bromide (41 μl; 0.348 mmol) was added and the mixture was subsequently stirred at room temperature for a further 21 hours. The reaction mixture was concentrated, the residue was taken up in water (2 ml) and some acetonitrile and chromatographed over a hydrophobic polymer with water/acetonitrile. There were obtained 54 mg (62%) of (E)-(1aS,3aR,6bR)-2-acetyl-5-[1-(1-benzyl-pyridin-1-ium-3-yl)-2-oxo-pyrrolidin-3-ylidenemethyl]-1-oxo-1a,2,3,3a,4,6b-hexahydro-1H-2,6a-diaza-cyclobut[cd]indene-6-carboxylic acid sodium salt (1:1) as a yellow powder.

IR (KBr): 1758, 1687, 1622, 1388 cm$^{-1}$; MS (ISP): 499.4 (M+H)$^+$.

In analogy thereto there was prepared:

EXAMPLE 40

(E)-(1aS,3aR,6bR)-2-Acetyl-5-[1-(1-carbamoylmethyl-pyridin-1-ium-3-yl)-2-oxo-pyrrolidin-3-ylidenemethyl]-1-oxo-1a,2,3,3a,4,6b-hexahydro-1H-2,6a-diaza-cyclobut[cd]indene-6-carboxylate

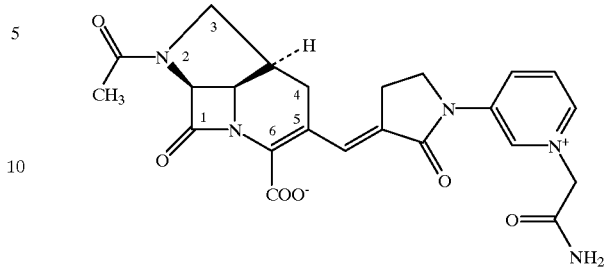

Starting from 75 mg (0.174 mmol) of (E)-(1aS,3aR,6bR)-2-acetyl-1-oxo-5-[2-oxo-1-(3-pyridinyl)-pyrrolidin-3-ylidene-methyl]-1a,2,3,3a,4,6b-hexahydro-1H-2,6a-diaza-cyclobut[cd]-indene-6-carboxylic acid sodium salt (1:1) (Example 33) and 2-bromo-acetamide (50 mg; 0.348 mmol) there were obtained 53 mg (66%) of (E)-(1aS,3aR,6bR)-2-acetyl-5-[1-(1-carbamoylmethyl-pyridin-1-ium-3-yl)-2-oxo-pyrrolidin-3-ylidenemethyl]-1-oxo-1a,2,3,3a,4,6b-hexahydro-1H-2,6a-diaza-cyclobut[cd]indene-6-carboxylic acid sodium salt (1:1) as an orange powder.

IR (KBr): 1757, 1694, 1624, 1390, 1215 cm$^{-1}$; MS (ISP): 466.3 (M+H)$^+$.

EXAMPLE 41

Scheme 2, (1)→(7)

Di-tert-butyl (1aS,3aR,6bR)-5-triphenylphosphoniummethyl-1-oxo-1a,2,3,3a,4,6b-hexahydro-1H-2,6a-diaza-cyclobut[cd]indene-2,6-dicarboxylate bromide

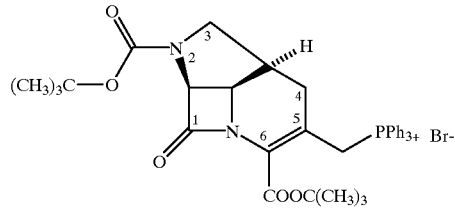

11.4 g (30 mmol) of di-tert-butyl (1aS,3aR,6bR)-5-hydroxy-methyl-1-oxo-1a,2,3,3a,4,6b-hexahydro-1H-2,6a-diaza-cyclobut[cd]indene-2,6-dicarboxylate were dissolved in methylene chloride (100 ml), treated with molecular sieve 4 Å (10 g) and cooled to (–40)° C. The reaction mixture was treated with triethylamine (6.0 ml; 42 mmol) and methanesulphonyl chloride (3.3 ml; 42 mmol), with the temperature rising to (–14)° C. As soon as the temperature has again fallen to (–40° C., a solution of calcium iodide (10.98 g; 30 mmol) in dimethyl sulphoxide (300 ml) was added in one portion, with the temperature rising to +10° C. The reaction mixture was cooled to 0° C. and stirred for a further hour. Subsequently, the solution was poured into 500 ml of ice-cold 1 N HCl and extracted with ethyl acetate (2×700 ml). The combined organic phases were washed in succession with 5% sodium thiosulphate solution (250 ml and 100 ml), saturated sodium hydrogen sulphate solution (100 ml) and saturated sodium chloride solution (2×100 ml), dried over magnesium sulphate, suction filtered and concentrated. The white residue obtained was triturated briefly with pentane (150 ml), filtered off under suction and dried to constant weight in a high vacuum. The white powder obtained (8.95 g) was taken up immediately in DMSO (90 ml) and acetonitrile (90 ml), treated with triphenylphosphine (9.55 g; 36.5 mmol) and stirred for 20 hours at 50° C. The reaction mixture was cooled to room temperature and extracted with water (300 ml) and ether (500 ml). The separated aqueous phase was back-washed with ether (300 ml). The two organic phases were back-extracted with water (100 ml). The combined aqueous phases were extracted with methylene chloride (2×300 ml) after saturation with NaCl. The methylene chloride phases were subsequently washed with a saturated sodium chloride solution (300 ml), dried over magnesium sulphate suction filtered and concentrated. The colorless resin obtained was triturated with ether (500 ml), filtered off under suction and dried to constant weight in a high vacuum. There were obtained 13.45 g (98%) of di-tert-butyl (1aS,3aR,6bR)-5-triphenylphosphoniummethyl-1-oxo-1a,2,3,3a, 4,6b-hexahydro-1H-2,6a-diaza-cyclobut[cd] indene-2,6-dicarboxylate bromide as a white powder.

IR (KBr): 1773, 1699, 1621, 1590, 1439, 1164, 1111 cm$^{-1}$; MS (ISP): 625.4 (M$^+$).

Wittig Reaction, Scheme 2, (7)→(8)

EXAMPLE 42

Di-tert-butyl (E)-(1aS,3aR,6bR)-5-(2-pyridin-3-yl-vinyl)-1-oxo-1a,2,3,3a,4,6b-hexahydro-1H-2,6a-diaza-cyclobut[cd]Indene-2,6-dicarboxylate

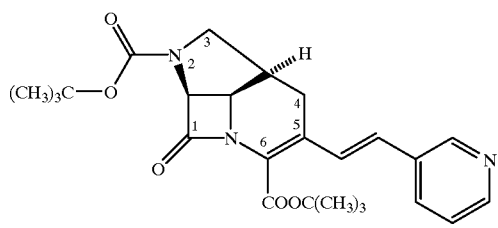

2.41 g (3.2 mmol) of di-tert-butyl (1aS,3aR,6bR)-5-triphenylphosphoniummethyl-1-oxo-1a,2,3,3a,4,6b-hexahydro-1H-2,6a-diaza-cyclobut[cd]indene-2,6-dicarboxylate (Example 41) were dissolved in 80 ml of abs. dimethyl sulphoxide and treated with pyridine-3-aldehyde (0.62 ml; 6.4 mmol) and triethylamine (1.12 ml; 8.0 mmol). After 24 hours at room temperature the reaction mixture was poured into 400 ml of phosphate buffer solution (pH 7) and extracted with ethyl acetate (2×200 ml). The combined organic 30 phases were subsequently washed with water (2×100 ml) and saturated sodium chloride solution (100 ml), dried over magnesium sulphate, suction filtered and concentrated. The residue obtained was chromatographed over silica gel (275 g; particle size 0.063–0.2 mm) with ethyl acetate/hexane 1:1. There were obtained 1.42 g (98%) of di-tert-butyl (E)-(1aS,3aR,6bR)-5-(2-pyridin-3-yl-vinyl)-1-oxo-1a,2,3,3a,4,6b-hexahydro-1H-2,6a-diaza-cyclobut[cd]indene-2,6-dicarboxylate as a yellow powder.

IR (KBr): 1769, 1704, 1634, 1162 cm$^{-1}$; MS (ISP): 454.5 (M+H)$^+$.

In analogy thereto there were prepared:

EXAMPLE 43

Di-tert-butyl (E)-(1aS,3aR,6bR)-5-styryl-1-oxo-1a,2,3, 3a,4,6b-hexahydro-1H-2,6a-diaza-cyclobut[cd]indene-2,6-dicarboxylate

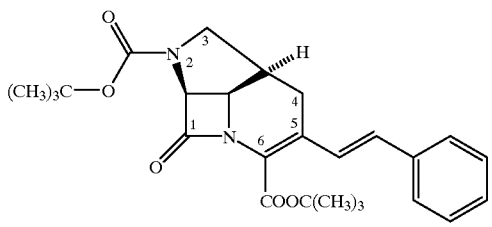

From di-tert-butyl (1aS,3aR,6bR)-5-triphenylphosphonium-methyl-1-oxo-1a,2,3,3a,4,6b-hexahydro-1H-2,6a-diaza-cyclobut[cd]indene-2,6-dicarboxylate bromide (151 mg; 0.2 mmol) (Example 41) and benzaldehyde (40 μl; 0.4 mmol).

Yield: 81 mg (90%) as a colorless powder. IR (KBr): 1764, 1704, 1580, 1478, 1250, 970 cm$^{-1}$; MS (ISP): 453.5 (M+H)$^+$.

EXAMPLE 44

Di-tert-butyl (E)-(1aS,3aR,6bR)-5-(2-pyridin-2-yl-vinyl)-1-oxo-1a,2,3,3a,4,6b-hexahydro-1H-2,6a-diaza-cyclobut[cd]indene-2,6-dicarboxylate

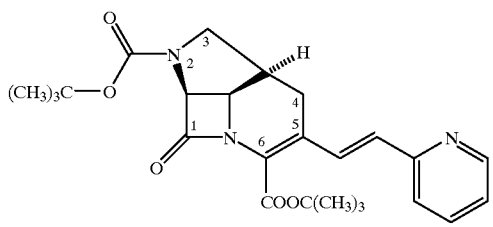

From di-tert-butyl (1aS,3aR,6bR)-5-triphenylphosphonium-methyl-1-oxo-1a,2,3,3a,4,6b-hexahydro-1H-2,6a-diaza-cyclobut[cd]indene-2,6-dicarboxylate bromide (2.41 g; 3.2 mmol) (Example 41) and pyridine-2-carboxaldehyde (0.63 ml; 6.4 mmol).

Yield: 1.13 g (78%) as a colorless powder. IR (KBr): 1774, 1706, 1622, 1581, 1243, 1161 cm$^{-1}$; MS (ISP): 454.5 (M+H)$^+$.

EXAMPLE 45

Di-tert-butyl (E)-(1aS,3aR,6bR)-5-(2-pyridin-4-yl-vinyl)-1-oxo-1a,2,3,3a,4,6b-hexahydro-1H-2,6a-diaza-cyclobut[cd]indene-2,6-dicarboxylate

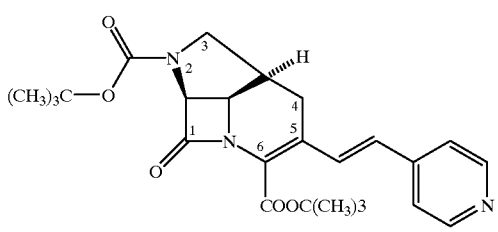

From di-tert-butyl (1aS,3aR,6bR)-5-triphenylphosphonium-methyl-1-oxo-1a,2,3,3a,4,6b-hexahydro-1H-2,6a-diaza-cyclobut[cd]indene-2,6-dicarboxylate bromide (2.41 g; 3.2 mmol) (Example 41) and pyridine-4-carboxaldehyde (0.63 ml; 6.4 mmol).

Yield: 1.20 g (80%) as a colorless powder. IR (KBr): 1773, 1705, 1594, 1439, 1161 cm$^{-1}$; MS (ISP): 454.5 (M+H)$^+$.

EXAMPLE 46

Di-tert-butyl (E)-(1aS,3aR,6bR)-5-[2-(4-tert-butoxy-carbonyloxy-phenyl)-vinyl]-1-oxo-1a,2,3,3a,4,6b-hexahydro-1H-2,6a-diaza-cyclobut[cd]indene-2,6-dicarboxylate

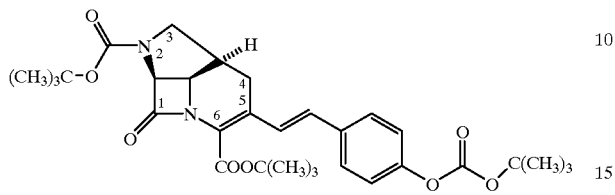

From di-tert-butyl (1aS,3aR,6bR)-5-triphenylphosphonium-methyl-1-oxo-1a,2,3,3a,4,6b-hexahydro-1H-2,6a-diaza-cyclobut[cd]indene-2,6-dicarboxylate bromide (1.2 g; 1.6 mmol) (Example 41) and carboxylic acid tert-butyl ester 4-formyl-phenyl ester (711 mg; 3.2 mmol).

Yield: 0.6 g (66%) as a colorless powder. IR (KBr): 1762, 1706, 1507, 1254, 1153 cm$^{-1}$; MS (ISP): 569.5 (M+H)$^+$.

EXAMPLE 47

Di-tert-butyl (E)-(1aS,3aR,6bR)-1-oxo-5-(2-quinolin-2-yl-vinyl)-1a,2,3,3a,4,6b-hexahydro-1H-2,6a-diaza-cyclobut[cd]indene-2,6-dicarboxylate

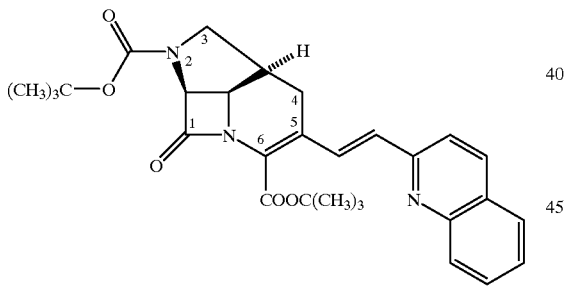

From di-tert-butyl (1aS,3aR,6bR)-5-triphenylphosphonium-methyl-1-oxo-1a,2,3,3a,4,6b-hexahydro-1H-2,6a-diaza-cyclobut[cd]indene-2,6-dicarboxylate bromide (2.41 g; 3.2 mmol) (Example 41) and quinoline-2-carbaldehyde (1.0; 6.4 mmol).

Yield: 1.5 g (94%) as a yellow foam-like resin. IR (KBr): 1775, 1706, 1246, 1160 cm$^{-1}$; MS (ISP): 504.5 (M+H)$^+$.

EXAMPLE 48

Di-tert-butyl (E)-(1aS,3aR,6bR)-1-oxo-5-[2-quinolin-3-yl-vinyl)-1a,2,3,3a,4,6b-hexahydro-1H-2,6a-diaza-cyclobut[cd]indene-2,6-dicarboxylate

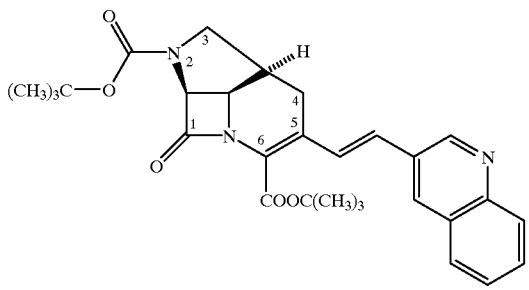

From di-tert-butyl (1aS,3aR,6bR)-5-triphenylphosphonium-methyl-1-oxo-1a,2,3,3a,4,6b-hexahydro-1H-2,6a-diaza-cyclobut[cd]indene-2,6-dicarboxylate bromide (2.41 g; 3.2 mmol) (Example 41) and quinoline-3-carbaldehyde (1.0; 6.4 mmol). Yield: 1.5 g (94%) as a yellow powder.

IR (KBr): 1770, 1705, 1621, 1476, 1161, 946 cm$^{-1}$; MS (ISP): 504.4 (M+H)$^+$.

Removal of the protecting group, Scheme 2, (8)→(9)

The following Examples were performed analogously to Example 13 (Scheme 1 (3)→(4)):

EXAMPLE 49

(E)-(1aS,3aR,6bR)-1-Oxo-5-styryl-1a,2,3,3a,4,6b-hexahydro-1H-2,6a-diaza-cyclobut[cd]indene-6-carboxylic acid trifluoroacetate

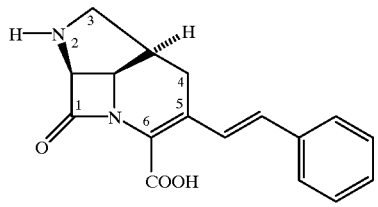

Starting from 100 mg (0.22 mmol) of di-tert-butyl (E)-(1aS,3aR,6bR)-5-styryl-1-oxo-1a,2,3,3a,4,6b-hexahydro-1H-2,6a-diaza-cyclobut[cd]indene-2,6-dicarboxylate (Example 43) there were obtained 83 mg (98%) of (E)-(1aS, 3aR,6bR)-1-oxo-5-styryl-1a,2,3,3a,4,6b-hexahydro-1H-2, 6a-diaza-cyclobut[cd]indene-6-carboxylic acid trifluoroacetate as a colorless powder.

IR (KBr): 3432, 1773, 1678, 1619, 1200, 966, 750, 693 cm$^{-1}$; MS (ISN): 295.3 (M−H)$^-$.

EXAMPLE 50

(E)-(1aS,3aR,6bR)-1-Oxo-5-(2-pyridin-2-yl-vinyl)-1a,2, 3,3a,4,6b-hexahydro-1H-2,6a-diaza-cyclobut[cd]indene-6-carboxylic acid trifluoroacetate (1:1.58)

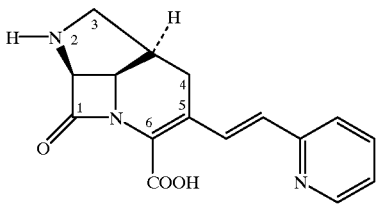

Starting from 303 mg (0.668 mmol) of di-tert-butyl (E)-(1aS,3aR,6bR)-5-(2-pyridin-2-yl-vinyl)-1-oxo-1a,2,3,3a,4,6b-hexahydro-1H-2,6a-diaza-cyclobut[cd]indene-2,6-dicarboxylate (Example 44) there were obtained 300 mg (94%) of (E)-(1aS,3aR,6bR)-1-oxo-5-(2-pyridin-2-yl-vinyl)-1a,2,3,3a,4,6b-hexahydro-1H-2,6a-diaza-cyclobut[cd]indene-6-carboxylic acid trifluoroacetate (1:1.58) as an orange powder.

IR (KBr): 1780, 1678, 1633, 1576, 1410, 1201 cm$^{-1}$; MS (ISP): 298.2 (M+H)$^+$.

EXAMPLE 51

(E)-(1aS,3aR,6bR)-1-Oxo-5-(2-pyridin-4-yl-vinyl)-1a,2,3,3a,4,6b-hexahydro-1H-2,6a-diaza-cyclobut[cd]indene-6-carboxylic acid trifluoroacetate (1:1.45)

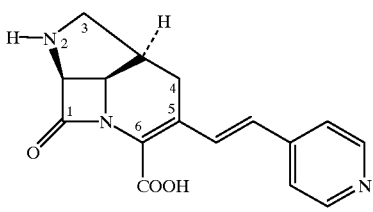

Starting from 363 mg (0.8 mmol) of di-tert-butyl (E)-(1aS,3aR,6bR)-5-(2-pyridin-4-yl-vinyl)-1-oxo-1a,2,3,3a,4,6b-hexahydro-1H-2,6a-diaza-cyclobut[cd]indene-2,6-dicarboxylate (Example 45) there were obtained 203 mg (55%) of (E)-(1aS,3aR,6bR)-1-oxo-5-(2-pyridin-4-yl-vinyl)-1a,2,3,3a,4,6b-hexahydro-1H-2,6a-diaza-cyclobut[cd]indene-6-carboxylic acid trifluoroacetate (1:1.45) as an orange powder.

IR (KBr): 1775, 1679, 1638,1 613, 1198 cm$^{-1}$; MS (ISP): 298.3 (M+H)$^+$.

EXAMPLE 52

(E)-(1aS,3aR,6bR)-1-Oxo-5-[2-(4-hydroxy-phenyl)-vinyl]-1a,2,3,3a,4,6b-hexahydro-1H-2,6a-diaza-cyclobut[cd]indene-6-carboxylic acid trifluoroacetate (1:0.83)

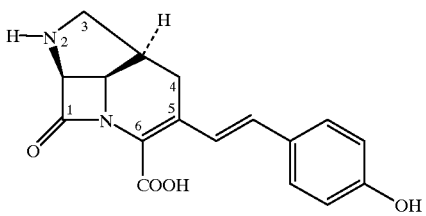

Starting from 571 mg (1mmol) of di-tert-butyl (E)-(1aS,3aR,6bR)-5-[2-(4-tert-butoxycarbonyloxy-phenyl)-vinyl]-1-oxo-1a,2,3,3a,4,6b-hexahydro-1H-2,6a-diaza-cyclobut[cd]indene-2,6-dicarboxylate (Example 46) there were obtained 375 mg (92%) of (E)-(1aS,3aR,6bR)-1-oxo-5-[2-(4-hydroxy-phenyl)-vinyl]- 1a,2,3,3a,4,6b-hexahydro-1H-2,6a-diaza-cyclobut[cd]indene-6-carboxylic acid trifluoroacetate (1:0.83) as a yellow powder.

IR (KBr): 1769, 1677, 1602, 1512, 1200 cm$^{-1}$; MS (ISN): 311.3 (M–H)$^-$.

EXAMPLE 53

(E)-(1aS,3aR,6bR)-1-Oxo-5-(2-pyridin-3-yl-vinyl)-1a,2,3,3a,4,6b-hexahydro-1H-2,6a-diaza-cyclobut[cd]indene-6-carboxylic acid trifluoroacetate (1:1.5)

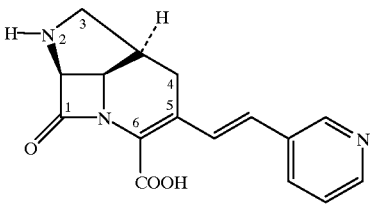

Starting from 1.42 g (3.13 mmol) of di-tert-butyl (E)-(1aS,3aR,6bR)-5-(2-pyridin-3-yl-vinyl)-1-oxo-1a,2,3,3a,4,6b-hexahydro-1H-2,6a-diaza-cyclobut[cd]indene-2,6-dicarboxylate (Example 42) there were obtained 1.05 g (72%) of (E)-(1aS,3aR,6bR)-1-oxo-5-(2-pyridin-3-yl-vinyl)-1a,2,3,3a,4,6b-hexahydro-1H-2,6a-diaza-cyclobut[cd]indene-6-carboxylic acid trifluoroacetate (1:1.5) as a yellow powder.

IR (KBr): 1773, 1679, 1631, 1202, 970 cm$^{-1}$; MS (ISP): 279.4 (M+H)$^+$; 298.4 (M+NH$_4$)$^+$; 301.3 (M+Na)$^+$.

EXAMPLE 54

(E)-(1aS,3aR,6bR)-1-Oxo-5-(2-quinolin-2-yl-vinyl)-1a,2,3,3a,4,6b-hexahydro-1H-2,6a-diaza-cyclobut[cd]indene-6-carboxylic acid trifluoroacetate (1:1.5)

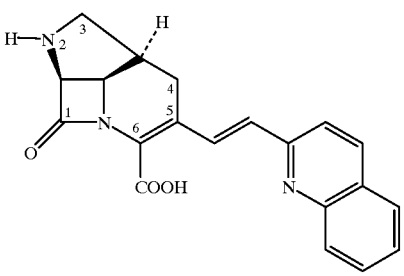

Starting from 1.5 g (2.97 mmol) of di-tert-butyl (E)-(1aS,3aR,6bR)-1-oxo-5-(2-quinolin-2-yl-vinyl)-1a,2,3,3a,4,6b-hexahydro-1H-2,6a-diaza-cyclobut[cd]indene-2,6-dicarboxylate (Example 47) there were obtained 1.3 g (86%) of (E)-(1aS,3aR,6bR)-1-oxo-5-(2-quinolin-2-yl-vinyl)-1a,2,3,3a,4,6b-hexahydro-1H-2,6a-diaza-cyclobut[cd]indene-6-carboxylic acid trifluoroacetate (1:1.5) as a dark red powder.

IR (KBr): 1772, 1677, 1644, 1619, 1204, 960, 725 cm$^{-1}$; MS (ISP): 348.4 (M+H)$^+$; 366.4 (M+NH$_4$)$^+$; 370.3 (M+Na)$^+$.

EXAMPLE 55

(E)-(1aS,3aR,6bR)-1-Oxo-5-(2-quinolin-3-yl-vinyl)-1a,2,3,3a,4,6b-hexahydro-1H-2,6a-diaza-cyclobut[cd]indene-6-carboxylic acid trifluoroacetate (1:1.4)

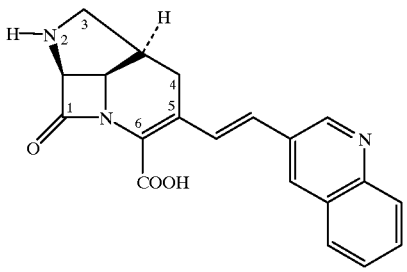

Starting from 1.5 g; (3 mmol) of di-tert-butyl (E)-(1aS,3aR,6bR)-1-oxo-5-[2-quinolin-3-yl-vinyl]-1a,2,3,3a,4,6b-hexahydro-1H-2,6a-diaza-cyclobut[cd]indene-2,6-dicarboxylate (Example 48) there were obtained 1.25 g (82%) of (E)-(1aS,3aR,6bR)-1-oxo-5-( 2-quinolin-3-yl-vinyl)-1a,2,3,3a,4,6b-hexahydro-1H-2,6a-diaza-cyclobut[cd]indene-6-carboxylic acid trifluoroacetate (1:1.4) as an orange powder.

IR (KBr): 1771, 1679, 1633, 1203, 970, 722 cm$^{-1}$; MS (ISP): 348.2 (M+H)$^+$.

Acylation, Scheme 1, (9)→(10)

EXAMPLE 56

(E)-(1aS,3aR,6bR)-2-Formyl-1-oxo-5-(2-pyridin-2-yl-vinyl)-1a,2,3,3a,4,6b-hexahydro-1H-2,6a-diaza-cyclobut[cd]indene-6-carboxylic acid sodium salt (1:1)

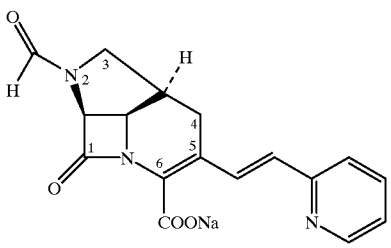

198 mg (0.4 mmol) of (E)-(1aS,3aR,6bR)-1-oxo-5-(2-pyridin-2-yl-vinyl)-1a,2,3,3a,4,6b-hexahydro-1H-2,6a-diaza-cyclobut[cd]indene-6-carboxylic acid trifluoroacetate (1:1.58) (Example 50) were dissolved in 4 ml of dimethylformamide, cooled to 0° C. and treated with concentrated formic acid (0.3 ml; 8 mmol) and dicyclohexylcarbodiimide (181 mg; 0.88 mmol). After 2 hours at 0° C. the precipitated material was filtered off under suction and the mother liquor was concentrated. The residue was suspended in 5 ml of water and the pH was adjusted to 7.5 with a saturated sodium hydrogen carbonate solution. The dissolved material was chromatographed over a hydrophobic polymer with water/acetonitrile 4:1. There were obtained 82 mg (59%) of (E)-(1aS,3aR,6bR)-2-formyl-1-oxo-5-(2-pyridin-2-yl-vinyl)- 1a,2,3,3a,4,6b-hexahydro-1H-2,6a-diaza-cyclobut[cd]indene-6-carboxylic acid sodium salt (1:1) as a red powder.

IR (KBr): 1754, 1659, 1602, 1390, 975, 769 cm$^{-1}$; MS (ISP): 326.3 (M+2H−Na)$^+$; 348.3 (M+H)$^+$.

The following Examples were performed in analogy to Example 24 (Scheme 1 (4)→(5)):

EXAMPLE 57

(E)-(1aS,3aR,6bR)-2-Acetyl-1-oxo-5-styryl-1a,2,3,3a,4,6b-hexahydro-1H-2,6a-diaza-cyclobut[cd]indene-6-carboxylic acid sodium salt (1:1)

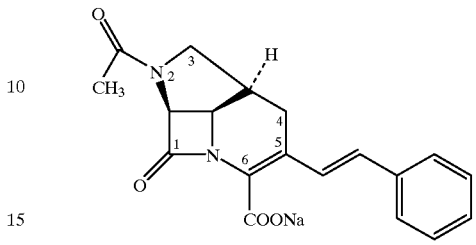

Starting from 65 mg (0.168 mmol) of (E)-(1aS,3aR,6bR)-1-oxo-5-styryl-1a,2,3,3a,4,6b-hexahydro-1H-2,6a-diaza-cyclobut[cd]indene-6-carboxylic acid trifluoroacetate (Example 49) and acetyl chloride (15 µl; 0.2 mmol) there were obtained 27 mg (45%) of (E)-(1aS,3aR,6bR)-2-acetyl-1-oxo-5-styryl-1a,2,3,3a, 4,6b-hexahydro-1H-2,6a-diaza-cyclobut[cd]indene-6-carboxylic acid sodium salt(1:1) as a colorless powder.

IR (KBr): 1748, 1619, 1605, 1394, 970, 751, 695 cm$^{-1}$; MS (ISP): 339.2 (M+H)$^+$; 356.3 (M+NH$_4$)$^+$; 361.2 (M+Na)$^+$.

EXAMPLE 58

(E)-(1aS,3aR,6bR)-2-Acetyl-1-oxo-5-(2-pyridin-2-yl-vinyl)-1a,2,3,3a,4,6b-hexahydro-1H-2,6a-diaza-cyclobut[cd]indene-6-carboxylic acid sodium salt (1:1)

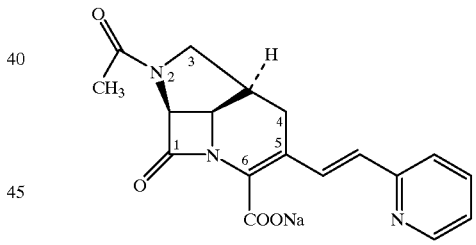

Starting from 141 mg (0.295 mmol) of (E)-(1aS,3aR,6bR)-1-oxo-5-(2-pyridin-2-yl-vinyl)-1a,2,3,3a,4,6b-hexahydro-1H-2,6a-diaza-cyclobut[cd]indene-6-carboxylic acid trifluoroacetate (1:1.58) (Example 50) and acetyl chloride (26 µl; 0.354 mmol) there were obtained 38 mg (36%) of (E)-(1aS,3aR,6bR)-2-acetyl-1-oxo-5-(2-pyridin-2-yl-vinyl)-1a,2,3,3a,4,6b-hexahydro-1H-2,6a-diaza-cyclobut[cd]indene-6-carboxylic acid sodium salt (1:1) as a colorless powder.

IR (KBr): 1751, 1650, 1621, 1390, 770 cm$^{-1}$; MS (ISP): 340.3 (M−Na+2H)$^+$; 362.3 (M+H)$^+$; 384.2 (M+Na)$^+$.

EXAMPLE 59

(E)-(1aS,3aR,6bR)-2-Acetyl-1-oxo-5-(2-pyridin-4-yl-vinyl)-1a,2,3,3a,4,6b-hexahydro-1H-2,6a-diaza-cyclobut[cd]indene-6-carboxylic acid sodium salt (1:1)

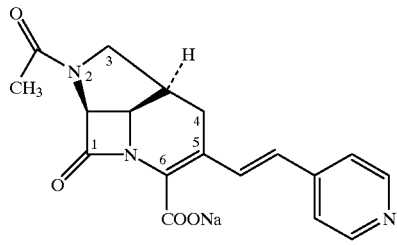

Starting from 155 mg (0.236 mmol) of (E)-(1aS,3aR,6bR)-1-oxo-5-(2-pyridin-4-yl-vinyl)-1a,2,3,3a,4,6b-hexahydro-1H-2,6a-diaza-cyclobut[cd]indene-6-carboxylic acid trifluoroacetate (1:1.45) (Example 51) and acetyl chloride (30 μl; 0.4 mmol) there were obtained 76 mg (62%) of (E)-(1aS,3aR,6bR)-2-acetyl-1-oxo-5-(2-pyridin-4-yl-vinyl)-1a,2,3,3a,4,6b-hexahydro-1H-2,6a-diaza-cyclobut[cd]indene-6-carboxylic acid sodium salt (1:1) as a red powder.

IR (KBr): 1752, 1670, 1600, 1389 cm$^{-1}$; MS (ISP): 340.3 (M+H)$^+$; 358.3 (M+NH$_4$)$^+$; 362.3 (M+Na)$^+$.

EXAMPLE 60

(E)-(1aS,3aR,6bR)-2-Acetyl-1-oxo-5-[2-(4-hydroxyphenyl)-vinyl]-1a,2,3,3a,4,6b-hexahydro-1H-2,6a-diaza-cyclobut[cd]indene-6-carboxylic acid sodium salt (1:1)

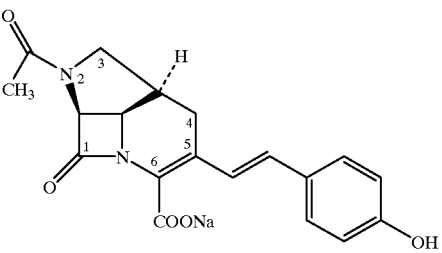

Starting from 122 mg (0.3 mmol) of (E)-(1aS,3aR,6bR)-1-oxo-5-[2-(4-hydroxy-phenyl)-vinyl]-1a,2,3,3a,4,6b-hexahydro-1H-2,6a-diaza-cyclobut[cd]indene-6-carboxylic acid trifluoroacetate (1:0.83) (Example 52) and acetyl chloride (27 μl; 0.36 mmol) there were obtained 82 mg (72%) of (E)-(1aS,3aR,6bR)-2-acetyl-1-oxo-5-[2-(4-hydroxy-phenyl)-vinyl]-1a,2,3,3a,4,6b-hexahydro-1H-2,6a-diaza-cyclobut[cd]indene-6-carboxylic acid sodium salt (1:1) as a yellow powder.

IR (KBr): 1744, 1640, 1604, 1511, 1447, 1245, 1170, 1013, 968 cm$^{-1}$; MS (ISP): 355.3 (M–Na+2H)$^+$; 372.3 (M–Na+H+NH$_4$)$^+$; 377.2 (M+H)$^+$.

EXAMPLE 61

(E)-(1aS,3aR,6bR)-2-Acetyl-1-oxo-5-(2-quinolin-2-yl-vinyl)-1a,2,3,3a,4,6b-hexahydro-1H-2,6a-diaza-cyclobut[cd]indene-6-carboxylic acid sodium salt (1:1)

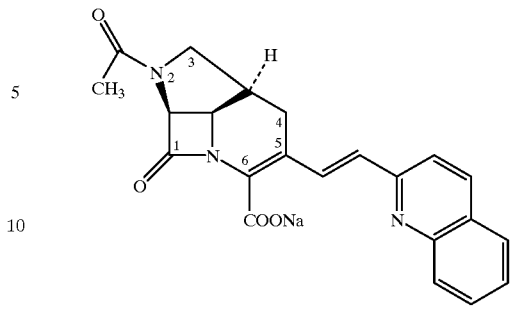

Starting from 1.3 g (2.55 mmol) of (E)-(1aS,3aR,6bR)-1-oxo-5-(2-quinolin-2-yl-vinyl)-1a,2,3,3a,4,6b-hexahydro-1H-2,6a-diaza-cyclobut[cd]indene-6-carboxylic acid trifluoroacetate (1:1.5) (Example 54) and acetyl chloride (225 μl; 3.06 mmol) there were obtained 231 mg (22%) of (E)-(1aS,3aR,6bR)-2-acetyl-1-oxo-5-(2-quinolin-2-yl-vinyl)-1a,2,3,3a,4,6b-hexahydro-1H-2,6a-diaza-cyclobut[cd]indene-6-carboxylic acid sodium salt (1:1) as a red powder.

IR (KBr): 1750, 1611, 1453, 970, 750 cm$^{-1}$; MS (ISP): 390.4 (M–Na+2H)$^+$; 412.2 (M+H)$^+$.

EXAMPLE 62

(E)-(1aS,3aR,6bR)-2-Acetyl-1-oxo-5-(2-pyridin-3-yl-vinyl)-1a,2,3,3a,4,6b-hexahydro-1H-2,6a-diaza-cyclobut[cd]indene-6-carboxylic acid sodium salt (1:1)

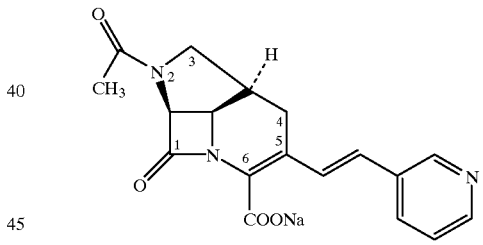

Starting from 1.03 g (2.2 mmol) of (E)-(1aS,3aR,6bR)-1-oxo-5-(2-pyridin-3-yl-vinyl)-1a,2,3,3a,4,6b-hexahydro-1H-2,6a-diaza-cyclobut[cd]indene-6-carboxylic acid trifluoroacetate (1:1.5) (Example 53) and acetyl chloride (194 μl; 2.64 mmol) there were obtained 434 mg (55%) of (E)-(1aS,3aR,6bR)-2-acetyl-1-oxo-5-(2-pyridin-3-yl-vinyl)-1a,2,3,3a,4,6b-hexahydro-1H-2,6a-diaza-cyclobut[cd]indene-6-carboxylic acid sodium salt (1:1) as an orange powder.

IR (KBr): 1749, 1650, 1622, 1418, 1392, 1361, 968 cm$^{-1}$; MS (ISP): 340.4 (M–Na+2H)$^+$; 362.3 (M+H)$^+$.

EXAMPLE 63

(E)-(1aS,3aR,6bR)-2-Acetyl-1-oxo-5-(2-quinolin-3-yl-vinyl)-1a,2,3,3a,4,6b-hexahydro-1H-2,6a-diaza-cyclobut[cd]indene-6-carboxylic acid sodium salt (1:1)

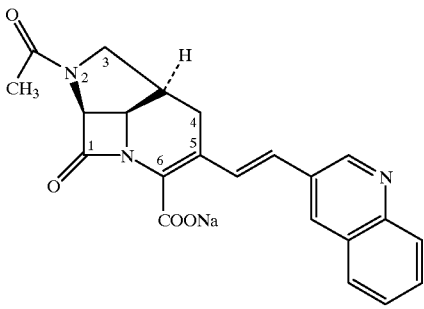

Starting from 507 mg (1mmol) of (E)-(1aS,3aR,6bR)-1-oxo-5-(2-quinolin-3-yl-vinyl)-1a,2,3,3a,4,6b-hexahydro-1H-2,6a-diaza-cyclobut[cd]indene-6-carboxylic acid trifluoroacetate (1:1.4) (Example 55) and acetyl chloride (88 μl; 1.2 mmol) there were obtained 234 mg (57%) of (E)-(1aS,3aR,6bR)-2-acetyl-1-oxo-5-(2-quinolin-3-yl-vinyl)-1a,2,3,3a,4,6b-hexahydro-1H-2,6a-diaza-cyclobut[cd]indene-6-carboxylic acid sodium salt (1:1) as a yellow powder.

IR (KBr): 1749, 1660, 1621, 1490, 1393, 960, 754 cm$^{-1}$; MS (ISP): 390.4 (M+H)$^+$; 412.3 (M+Na)$^+$.

The following Example was performed analogously to Example 34 (Scheme 1, (4)→(5)):

EXAMPLE 64

(E)-(1aS,3aR,6bR)-1-Oxo-5-(2-pyridin-2-yl-vinyl)-2-trifluoroacetyl-1a,2,3,3a,4,6b-hexahydro-1H-2,6a-diaza-cyclobut[cd]indene-6-carboxylic acid sodium salt (1:1)

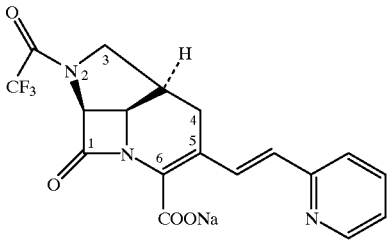

Starting from 141 mg () of (E)-(1aS,3aR,6bR)-1-oxo-5-(2-pyridin-2-yl-vinyl)-1a,2,3,3a,4,6b-hexahydro-1H-2,6a-diaza-cyclobut[cd]indene-6-carboxylic acid trifluoroacetate (1:1.58) (Example 50) there were obtained 51 mg (42%) of (E)-(1aS,3aR,6bR)-1-oxo-5-(2-pyridin-2-yl-vinyl)-2-trifluoroacetyl-1a,2,3,3a,4,6b-hexahydro-1H-2,6a-diaza-cyclobut[cd]indene-6-carboxylic acid sodium salt (1:1) as an orange powder.

IR (KBr): 1761, 1693, 1622, 1393, 1154 cm$^{-1}$; MS (ISP): 394.2 (M+2H−Na)$^+$; 416.3 (M+H)$^+$.

Quaternisation, Scheme 2, (10)→(11)

The following Examples were performed analogously to Example 39, (Scheme 1, (5)→(6)):

EXAMPLE 65

(E)-(1aS,3aR,6bR)-2-Acetyl-5-[2-(1-benzyl-pyridin-1-ium-2-yl)-vinyl]-1-oxo-1a,2,3,3a,4,6b-hexahydro-1H-2,6a-diaza-cyclobut[cd]indene-6-carboxylate

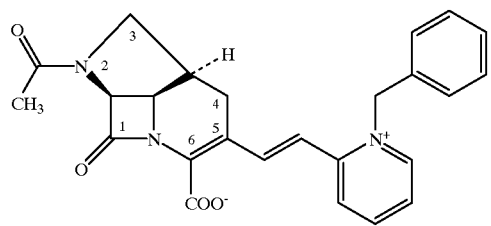

Starting from 75 mg (0.207 mmol) of (E)-(1aS,3aR,6bR)-2-acetyl-1-oxo-5-(2-pyridin-2-yl-vinyl)-1a,2,3,3a,4,6b-hexahydro-1H-2,6a-diaza-cyclobut[cd]indene-6-carboxylic acid sodium salt (Example 58) there were obtained 41 mg (47%) of (E)-(1aS,3aR,6bR)-2-acetyl-5-[2-(1-benzyl-pyridin-1-ium-2-yl)-vinyl]-1-oxo-1a,2,3,3a,4,6b-hexahydro-1H-2,6a-diaza-cyclobut[cd]indene-6-carboxylic acid sodium salt (1:1) as a yellow powder.

IR (KBr): 1769, 1714, 1645, 1429, 970, 740, 700 cm$^{-1}$; MS (ISP): 430.5 (M+H)$^+$.

EXAMPLE 66

(E)-(1aS,3aR,6bR)-2-Acetyl-5-[2-(1-benzyl-pyridin-1-ium-3-yl)-vinyl]-1-oxo-1a,2,3,3a,4,6b-hexahydro-1H-2,6a-diaza-cyclobut[cd]indene-6-carboxylate

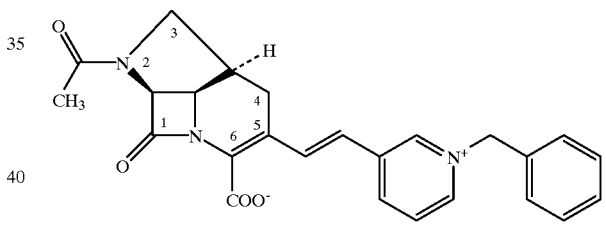

Starting from 75 mg (0.207 mmol) of (E)-(1aS,3aR,6bR)-2-acetyl-1-oxo-5-(2-pyridin-3-yl-vinyl)-1a,2,3,3a,4,6b-hexahydro-1H-2,6a-diaza-cyclobut[cd]indene-6-carboxylic acid sodium salt (Example 62) there were obtained 65 mg (74%) of (E)-(1aS,3aR,6bR)-2-acetyl-5-[2-(1-benzyl-pyridin-1-ium-3-yl)-vinyl]-1-oxo-1a,2,3,3a,4,6b-hexahydro-1H-2,6a-diaza-cyclobut[cd]indene-6-carboxylic acid sodium salt (1:1) as an orange powder.

IR (KBr): 1768, 1710, 1643 cm$^{-1}$; MS (ISP): 430.5 M$^+$.

The following Examples were performed analogously to Example 40 (Scheme 1, (5)→(6)):

EXAMPLE 67

(E)-(1aS,3aR,6bR)-2-Acetyl-5-[2-(1-carbamoylmethyl-pyridin-1-ium-3-yl)-vinyl]-1-oxo-1a,2,3,3a,4,6b-hexahydro-1H-2,6a-diaza-cyclobut[cd]indene-6-carboxylate

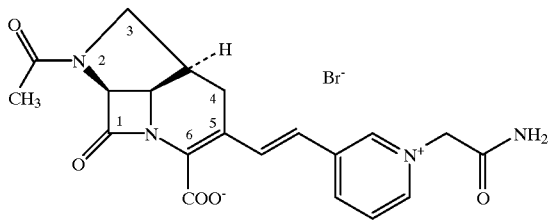

Starting from 75 mg (0.207 mmol) of (E)-(1aS,3aR,6bR)-2-acetyl-1-oxo-5-(2-pyridin-3-yl-vinyl)-1a,2,3,3a,4,6b-hexahydro-1H-2,6a-diaza-cyclobut[cd]-indene-6-carboxylic acid sodium salt (1:1) (Example 62) there were obtained 39 mg (39%) of (E)-(1aS,3aR,6bR)-2-acetyl-5-[2-(1-carbamoylmethyl-pyridin-1-ium-3-yl)-vinyl]-1-oxo-1a,2,3,3a,4,6b-hexahydro-1H-2,6a-diaza-cyclobut[cd]indene-6-carboxylic acid sodium salt (1:1) as an orange powder.

IR (KBr): 1754, 1695, 1618, 1505, 1207, 970 cm$^{-1}$; MS (ISP): 397.4 M$^+$.

EXAMPLE 68

(E)-(1aS,3aR,6bR)-2-Acetyl-5-[2-(1-carbamoylmethyl-quinolin-1-ium-3-yl)-vinyl]-1-oxo-1a,2,3,3a,4,6b-hexahydro-1H-2,6a-diaza-cyclobut[cd]indene-6-carboxylate

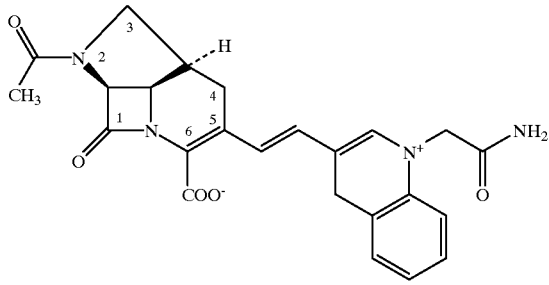

Starting from 82 mg (0.2 mmol) of (E)-(1aS,3aR,6bR)-2-acetyl-1-oxo-5-(2-quinolin-2-yl-vinyl)-1a,2,3,3a,4,6b-hexahydro-1H-2,6a-diaza-cyclobut[cd]indene-6-carboxylic acid sodium salt (1:1) (Example 63) there were obtained 20 mg (22%) of (E)-(1aS,3aR,6bR)-2-acetyl-5-[2-(1-carbamoylmethyl-quinolin-1-ium-3-yl)-vinyl]-1-oxo-1a,2,3,3a,4,6b-hexahydro-1H-2,6a-diaza-cyclobut[cd]indene-6-carboxylic acid sodium salt (1:1) as a brown powder.

IR (KBr): 1754, 1696, 1621, 1530, 1389, 780 cm$^{-1}$; MS (ISP): 447.5 (M+H)$^+$.

EXAMPLE 69

(1aS,3aR,6bR)-2-Acetyl-1-oxo-5-[(E)-2-[1-[(E)-3-phenylallyl]-pyridin-1-ium-3-yl)-vinyl]-1a,2,3,3a,4,6b-hexahydro-1H-2,6a-diaza-cyclobut[cd]indene-6-carboxylate

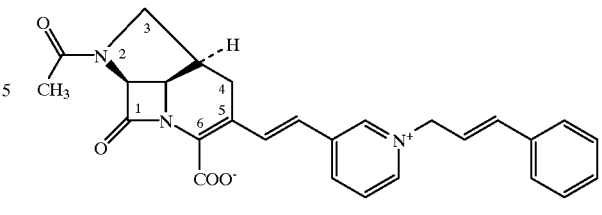

Analogously to Example 39, starting from 55 mg (0.152 mmol) of (E)-(1aS,3aR,6bR)-2-acetyl-1-oxo-5-(2-pyridin-3-yl-vinyl)-1a,2,3,3a,4,6b-hexahydro-1H-2,6a-diaza-cyclobut[cd]indene-6-carboxylic acid sodium salt (1:1) (Example 62) and 3-bromo-1-phenyl-1-propene (61 mg; 0.304 mmol).

Yield: 44 mg (64%) as an orange powder. IR (KBr): 1754, 1621, 1400, 970 cm$^{-1}$; MS (ISP) 456.4 (M+H)$^+$.

EXAMPLE 70

(E)-(1aS,3aR,6bR)-2-Acetyl-5-[2-[1-[(4-hydroxyphenylcarbamoyl)-methyl]-pyridin-1-ium-3-yl)-vinyl]-1-oxo-1a,2,3,3a,4,6b-hexahydro-1H-2,6a-diaza-cyclobut[cd]indene-6-carboxylate

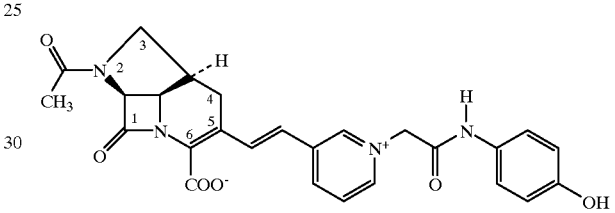

Analogously to Example 39, starting from 55 mg (0.152 mmol) of (E)-(1aS,3aR,6bR)-2-acetyl-1-oxo-5-(2-pyridin-3-yl-vinyl)-1a,2,3,3a,4,6b-hexahydro-1H-2,6a-diaza-cyclobut[cd]indene-6-carboxylic acid sodium salt (1:1) (Example 62) and 2-bromo-4'-hydroxyacetanilide (70 mg; 0.304 mmol). Yield: 42 mg (57%) as an orange powder.

IR (KBr): 1754, 1683, 1625, 1577, 1513, 1392, 1363, 1252 cm$^{-1}$; MS (ISP): 489.2 (M+H)$^+$.

EXAMPLE 71

(E)-(1aS,3aR,6bR)-2-Acetyl-1-oxo-5-[2-[1-[(4-trifluoromethoxy-benzyl)-pyridin-1-ium-3-yl]-vinyl]-1a,2,3,3a,4,6b-hexahydro-1H-2,6a-diaza-cyclobut[cd]indene-6-carboxylate

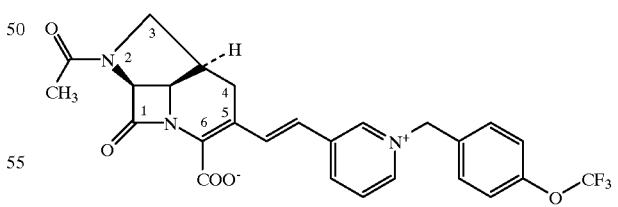

Analogously to Example 39, starting from 55 mg (0.1 52 mmol) of (E)-(1aS,3aR,6bR)-2-acetyl-1-oxo-5-(2-pyridin-3-yl-vinyl)-1a,2,3,3a,4,6b-hexahydro-1H-2,6a-diaza-cyclobut[cd]indene-6-carboxylic acid sodium salt (1:1) (Example 62) and 4-trifluoromethoxy-benzyl bromide (78 mg; 0.304 mmol).

Yield: 40 mg (51%) as an orange powder. IR (KBr): 1756, 1619, 1507, 1421, 1389, 1362, 1315, 1259, 1217, 1166, 960 cm$^{-1}$; MS (ISP): 514.3 (M+H)$^+$.

EXAMPLE 72

(E)-(1aS,3aR,6bR)-2-Acetyl-5-[2-(1-carbamoylmethyl-pyridin-1-ium-2-yl)-vinyl]-1-oxo-1a,2,3,3a,4,6b-hexahydro-1H-2,6a-diaza-cyclobut[cd]indene-6-carboxylate

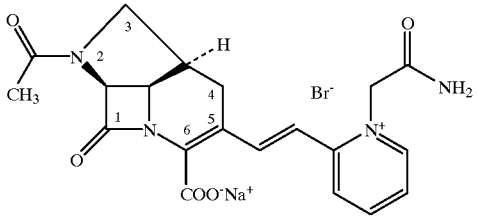

Starting from 50 mg (0.138 mmol) of (E)-(1aS,3aR,6bR)-2-acetyl-1-oxo-5-(2-pyridin-2-yl-vinyl)-1a,2,3,3a,4,6b-hexahydro-1H-2,6a-diaza-cyclobut[cd]indene-6-carboxylic acid sodium salt (1:1) (Example 58) there were obtained 26 mg (37%) of (E)-(1aS,3aR,6bR)-2-acetyl-5-[2-(1-carbamoylmethyl-pyridin-1-ium-2-yl)-vinyl]-1-oxo-1a,2,3,3a,4,6b-hexahydro-1H-2,6a-diaza-cyclobut[cd]indene-6-carboxylic acid sodium salt (1:1) as an orange powder.

IR (KBr): 1753, 1677, 1621, 980 cm$^{-1}$; MS (ISP): 397.4 M$^+$.

EXAMPLE 73

Production of dry ampoules for intramuscular administration:

A lyophilizate of 0.5 g of (E)-(1aS,3aR,6bR)-2-acetyl-1-oxo-5-[2-oxo-1-(4-hydroxyphenyl)-pyrrolidin-3-ylidenmethyl]-1a,2,3,3a,4,6b-hexahydro-1H-2,6a-diaza-cyclobut[cd]indene-6-carboxylic acid sodium salt (Example 24) and 1 g of ceftriaxone is prepared and filled into an ampoule. Prior to administration the lyophilizate is treated with 4 ml of a 2% aqueous lidocaine hydrochloride solution.

If desired, the two active substances can be filled separately into two different ampoules.

A different compound of formula I can also be used as the active substance. In addition to ceftriaxone, other known β-lactam antibiotics come into consideration as the β-lactam antibiotic.

What is claimed is:
1. A compound of formula I

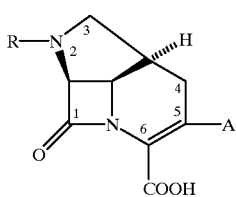

wherein
R is hydrogen, unsubstituted lower (cyclo)alkyl or lower (cyclo)alkyl substituted by carboxy, lower alkoxycarbonyl, carbamoyl, lower alkylcarbamoyl, phenylcarbamoyl or hydroxyphenylcarbamoyl; lower alkenylmethyl; lower alkenylmethoxycarbonyl; formyl; unsubstituted lower (cyclo)alkanoyl; or lower (cyclo)alkanoyl substituted by halogen, cyano, carbamoyl-lower alkoxy, carbamoyl-lower alkylthio or carbamoyl-lower alkylamino, unsubstituted lower (cyclo)alkylsulphonyl; or lower (cyclo)alkylsulphonyl substituted by halogen, cyano, carbamoyl-lower alkoxy, carbamoyl-lower alkylthio or carbamoyl-lower alkylamino; unsubstituted carbamoyl or carbamoyl substituted by lower (cyclo)alkyl, lower alkoxycarbonyl-lower alkyl, benzyloxy-carbonyl-lower alkyl, carboxy-lower alkyl, hydroxyphenyl or carbamoylphenyl; or a ring structure of the formula Q—X—CO— (a1)

or

Q—X—SO$_2$— (a2)

Q is a 5- or 6-membered ring optionally containing nitrogen, sulphur and/or oxygen;
X is a direct bond or a group —CH$_2$—, —CH$_2$CH$_2$—, —CH=CH—, —NH—, —NHCH$_2$—, —CH$_2$NH—, —CH(NH$_2$)—, —CH$_2$CH$_2$NH—, —C(=NOCH$_3$)—, —OCH$_2$— or —SCH$_2$—; and
A is a group of formula (b1) or (b2)

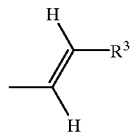

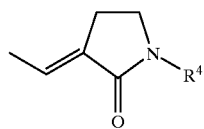

wherein
R$^3$ is unsubstituted aryl or aryl substituted by one or two substituents selected from halogen, hydroxy, cyano, nitro, lower alkyl, lower alkoxy, aralkyl, —CONR$^5$R$^6$, —CH$_2$—CONR$^5$R$^6$, —N(R$^6$)COOR$^7$, R$^6$CO—, R$^6$OCO— or R$^6$COO— in which R$^5$ is hydrogen, lower alkyl or lower cycloalkyl; R$^6$ is hydrogen or lower alkyl; and R$^7$ is hydrogen, lower alkyl, lower alkenyl or a carboxylic acid protecting group selected from benzhydryl, p-nitrobenzyl, and p-methoxybenzyl; an unsubstituted heterocyclyl which is a 5- or 6-membered ring optionally containing nitrogen, sulfur and/or oxygen; a heterocyclyl which is a 5- or 6-membered ring optionally containing nitrogen, sulfur and/or oxygen substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, lower alkenyl substituted phenyl, —CONR$^5$R$^6$, —CH$_2$—CONR$^5$R$^6$, —N(R$^6$)COOR$^7$, R$^6$CO—, R$^6$OCO— or R$^6$COO— in which R$^5$ is hydrogen, lower alkyl or lower cycloalkyl; R$^6$ is hydrogen or lower alkyl; and R$^7$ is hydrogen, lower alkyl, lower alkenyl or a carboxylic acid protecting group selected from benzhydryl, p-nitrobenzyl and p-methoxybenzyl; or a heterocyclyl which is a 5- or 6-membered ring optionally containing nitrogen, sulfur and/or oxygen having a phenyl ring fused thereto, the heterocyclyl thereof being unsubstituted or substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, or lower alkenyl substituted phenyl; and $R^4$ is hydrogen, hydroxy, lower (cyclo)alkyl, lower alkoxy, lower (cyclo)alkenyl, lower alkynyl, aralkyl, aryl, aryloxy, aralkyloxy, heterocyclyl which is a 5- or 6-membered ring optionally containing nitrogen, sulfur and/or oxygen or lower alkyl substituted with a heterocyclyl which is a 5- or 6-membered ring optionally containing nitrogen, sulfur and/or oxygen, with each of lower (cyclo)alkyl, lower alkoxy, lower (cyclo)alkenyl, aralkyl, aryl, aryloxy, aralkyloxy or heterocyclyl ring which is a 5- or 6-membered ring optionally containing nitrogen, sulfur and/or oxygen being unsubstituted or substituted by carboxy, amino, nitro, cyano, lower alkyl, benzyl, lower alkoxy, hydroxy, halogen, —CONR$^5$R$^6$, —CH$_2$—CONR$^5$R$^6$, —N(R$^6$)COOR$^7$, R$^6$CO—, R$^6$OCO— or R$^6$COO— in which $R^5$ is hydrogen, lower alkyl or lower cycloalkyl; $R^6$ is hydrogen or lower alkyl; and $R^7$ is hydrogen, lower alkyl, lower alkenyl or a carboxylic acid protecting group selected from benzhydryl, p-nitrobenzyl, and p-methoxybenzyl; and pharmaceutically compatible, readily hydrolyzable esters thereof selected from lower alkanoyloxyalkyl esters, lower alkoxycarbonyloxyalkyl esters, 1-cyclohexyloxycarbonyloxyethyl ester, (5-methyl-2-oxo-1,3-dioxol-4-yl)-methyl ester, phthalidyl esters, thiophthalidyl esters, lower alkoxymethyl esters, lower alkanoylaminomethyl esters, benzyl esters, cyanomethyl esters, (2,2-dimethyl-1-oxopropoxy)methyl ester, [2-[(2-mehtylpropoxy)carbonyl]-2-pentenyl]2-(2-methylpropoxy)carbonyl]-2-pentenyl ester, 1-(1-methylethoxy)carbonyl]oxy]ethyl ester and 3-3-dimethyl-2-oxobutyl ester, and salts of these compounds.

2. The compound of claim 1, wherein R is hydrogen, formyl, unsubstituted lower alkanoyl, lower alkanoyl substituted by halogen, unsubstituted carbamoyl, or carbamoyl substituted by hydroxyphenyl or carbamoylphenyl.

3. The compound of claim 2, wherein R is hydrogen, formyl, unsubstituted lower alkanoyl, lower alkanoyl substituted by halogen, or carbamoyl substituted by hydroxyphenyl or carbamoylphenyl.

4. The compound of claim 3, wherein R is hydrogen.

5. The compound of claim 4, wherein A is formula (b1).

6. The compound of claim 5, wherein $R^3$ is unsubstituted aryl or aryl substituted by hydroxy.

7. The compound of claim 6, wherein $R^3$ is unsubstituted aryl.

8. The compound of claim 7, (E)-(1aS,3aR,6bR)-1-oxo-5-styryl-1a,2,3,3a,4,6b-hexahydro-1H-2,6a-diaza-cyclobut[cd]indene-6-carboxylic acid.

9. The compound of claim 6, wherein $R^3$ is aryl substituted by hydroxy.

10. The compound of claim 9, (E)-(1aS,3aR,6bR)-1-oxo-5-[2-(4-hydroxy-phenyl)-vinyl]-1a,2,3,3a,4,6b-hexahydro-1H-2,6a-diaza-cyclobut[cd]indene-6-carboxylic acid.

11. The compound of claim 5, wherein $R^3$ is unsubstituted heterocyclyl or heterocyclyl having a phenyl ring fused thereto.

12. The compound of claim 11, wherein $R^3$ is unsubstituted heterocyclyl.

13. The compound of claim 12, wherein the unsubstituted heterocyclyl is selected from pyridin-2-yl, pyridin-3-yl, and pyridin-4-yl.

14. The compound of claim 13, (E)-(1aS,3aR,6bR)-1-oxo-5-(2-pyridin-2-yl-vinyl)-1a,2,3,3a,4,6b-hexahydro-1H-2,6a-diaza-cyclobut[cd]indene-6-carboxylic acid.

15. The compound of claim 13, (E)-(1aS,3aR,6bR)-1-oxo-5-(2-pyridin-3-yl-vinyl)-1a,2,3,3a,4,6b-hexahydro-1H-2,6a-diaza-cyclobut[cd]indene-6-carboxylic acid.

16. The compound of claim 13, (E)-(1aS,3aR,6bR)-1-oxo-5-(2-pyridin-4-yl-vinyl)-1a,2,3,3a,4,6b-hexahydro-1H-2,6a-diaza-cyclobut[cd]indene-6-carboxylic acid.

17. The compound of claim 11, wherein $R^3$ is heterocyclyl having a phenyl ring fused thereto.

18. The compound of claim 17, wherein heterocyclyl having a phenyl ring fused thereto is selected from quinolin-2-yl, quinolin-3-yl, and quinolin-4-yl.

19. The compound of claim 18, (E)-(1aS,3aR,6bR)-1-oxo-5-(2-quinolin-2-yl-vinyl)-1a,2,3,3a,4,6b-hexahydro-1H-2,6a-diaza-cyclobut[cd]indene-6-carboxylic acid.

20. The compound of claim 18, (E)-(1aS,3aR,6bR)-1-oxo-5-(2-quinolin-3-yl-vinyl)-1a,2,3,3a,4,6b-hexahydro-1H-2,6a-diaza-cyclobut[cd]indene-6-carboxylic acid.

21. The compound of claim 3, wherein R is formyl.

22. The compound of claim 21, wherein A is formula (b1).

23. The compound of claim 22, wherein $R^3$ is unsubstituted heterocyclyl or heterocyclyl having a phenyl ring is fused thereto.

24. The compound of claim 23, wherein $R^3$ is unsubstituted heterocyclyl.

25. The compound of claim 24, wherein unsubstituted heterocyclyl is selected from pyridin-2-yl, pyridin-3-yl, and pyridin-4-yl.

26. The compound of claim 25, (E)-(1aS,3aR,6bR)-2-formyl-1-oxo-5-(2-pyridin-2-yl-vinyl)-1a,2,3,3a,4,6b-hexahydro-1H-2,6a-diaza-cyclobut[cd]indene-6-carboxylic acid.

27. The compound of claim 3, wherein R is unsubstituted lower alkanoyl.

28. The compound of claim 27, wherein A is formula (b1).

29. The compound of claim 28, wherein $R^3$ is unsubstituted aryl or aryl substituted by hydroxy.

30. The compound of claim 29, wherein $R^3$ is unsubstituted aryl.

31. The compound of claim 30, (E)-(1aS,3aR,6bR)-2-acetyl-1-oxo-5-styryl-1a,2,3,3a,4,6b-hexahydro-1H-2,6a-diaza-cyclobut[cd]indene-6-carboxylic acid.

32. The compound of claim 29, wherein $R^3$ is aryl substituted by hydroxy.

33. The compound of claim 32, (E)-(1aS,3aR,6bR)-2-acetyl-1-oxo-5-[2-(4-hydroxy-phenyl)-vinyl]-1a,2,3,3a,4,6b-hexahydro-1H-2,6a-diaza-cyclobut[cd]indene-6-carboxylic acid.

34. The compound of claim 28, wherein $R^3$ is unsubstituted heterocyclyl; heterocyclyl substituted by hydroxyphenylcarbamoyl, carbamoylmethyl, unsubstituted benzyl, halo lower alkoxy substituted benzyl, or phenyl substituted lower alkenyl; or heterocyclyl having a phenyl ring fused thereto, the heterocyclyl thereof being unsubstituted or substituted by carbamoylmethyl.

35. The compound of claim 34, wherein $R^3$ is unsubstituted heterocyclyl.

36. The compound of claim 35, wherein the unsubstituted heterocyclyl is selected from pyridin-2-yl, pyridin-3-yl, and pyridin-4-yl.

37. The compound of claim 36, (E)-(1aS,3aR,6bR)-2-Acetyl-1-oxo-5-(2-pyridin-2-yl-vinyl)-1a,2,3,3a,4,6b-hexahydro-1H-2,6a-diaza-cyclobut[cd]indene-6-carboxylic acid.

38. The compound of claim 36, (E)-(1aS,3aR,6bR)-2-acetyl-1-oxo-5-(2-pyridin-3-yl-vinyl)-1a,2,3,3a,4,6b-hexahydro-1H-2,6a-diaza-cyclobut[cd]indene-6-carboxylic acid.

39. The compound of claim 36, (E)-(1aS,3aR,6bR)-2-acetyl-1-oxo-5-(2-pyridin-4-yl-vinyl)-1a,2,3,3a,4,6b-hexahydro-1H-2,6a-diaza-cyclobut[cd]indene-6-carboxylic acid.

40. The compound of claim 34, wherein $R^3$ is heterocyclyl having a phenyl ring fused thereto.

41. The compound of claim 40, wherein heterocyclyl having a phenyl ring fused thereto is selected from quinolin-2-yl, quinolin-3-yl, and quinolin-4-yl.

42. The compound of claim 41, (E)-(1aS,3aR,6bR)-2-acetyl-1-oxo-5-(2-quinolin-2-yl-vinyl)-1a,2,3,3a,4,6b-hexahydro-1H-2,6a-diaza-cyclobut[cd]indene-6-carboxylic acid.

43. The compound of claim 41, (E)-(1aS,3aR,6bR)-2-acetyl-1-oxo-5-(2-quinolin-2-yl-vinyl)-1a,2,3,3a,4,6b-hexahydro-1H-2,6a-diaza-cyclobut[cd]indene-6-carboxylic acid.

44. The compound of claim 34, wherein $R^3$ is a heterocyclyl substituted by hydroxyphenylcarbamoyl, carbamoylmethyl, unsubstituted benzyl, halo lower alkoxy substituted benzyl, or phenyl substituted lower alkenyl.

45. The compound of claim 3, wherein R is carbamoyl substituted by carbamoylphenyl.

46. The compound of claim 45, wherein A is formula (b2).

47. The compound of claim 44, wherein the heterocyclyl is substituted by carbamoylmethyl or unsubstituted benzyl.

48. The compound of claim 46, wherein $R^4$ is selected from unsubstituted lower alkyl, lower alkyl substituted by halogen, lower cycloalkyl, unsubstituted aryl, aryl substituted by hydroxy or nitro, unsubstituted aralkyl or aralkyl substituted by nitro, heterocyclylalkyl, unsubstituted heterocyclyl, heterocyclyl substituted by benzyl, $R^6OCO$— or —$CH_2$—$CONR^5R^6$ where $R^5$ is hydrogen or lower alkyl and $R^6$ is hydrogen or lower alkyl.

49. The compound of claim 48, wherein $R^4$ is selected from unsubstituted lower alkyl or lower alkyl substituted by halogen.

50. The compound of claim 49, wherein $R^4$ is lower alkyl substituted by halogen.

51. The compound of claim 44, wherein the heterocyclyl is substituted by unsubstituted benzyl, carbamoylmethyl, hydroxyphenylcarbamoyl, halo lower alkoxy substituted benzyl, or phenyl substituted lower alkenyl.

52. The compound of claim 50, (E)-(1aS,3aR,6bR)-2-(4-carbamoyl-phenylcarbamoyl)-1-oxo-5-[2-oxo-1-(2,2,2-trifluoro-ethyl)-pyrrolidin-3-ylidenemethyl]-1a,2,3,3a,4,6b-hexahydro-1H-2,6a-diaza-cyclobut[cd]indene-6-carboxylic acid.

53. A compound of formula II

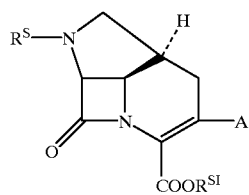

II wherein
A is a group of formula (b1) or (b2)

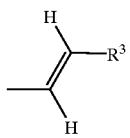

(b1)

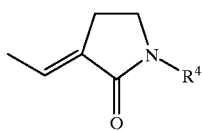

(b2)

wherein
$R^3$ is unsubstituted aryl or aryl substituted by one or two substituents selected from halogen, hydroxy, cyano, nitro, lower alkyl, lower alkoxy, aralkyl, —$CONR^5R^6$, —$CH_2$—$CONR^5R^6$, —$N(R^6)COOR^7$, $R^6CO$—, $R^6OCO$— or $R^6COO$— in which $R^5$ is hydrogen, lower alkyl or lower cycloalkyl; $R^6$ is hydrogen or lower alkyl; and $R^7$ is hydrogen, lower alkyl, lower alkenyl or a carboxylic acid protecting group selected from benzhydryl, p-nitrobenzyl and p-methoxybenzyl; an unsubstituted heterocyclyl which is a 5- or 6-membered ring optionally containing nitrogen, sulfur and/or oxygen; a heterocyclyl which is a 5- or 6-membered ring optionally containing nitrogen, sulfur and/or oxygen substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, lower alkenyl substituted phenyl, —$CONR^5R^6$, —$CH_2$—$CONR^5R^6$, —$N(R^6)COOR^7$, $R^6CO$—, $R^6OCO$— or $R^6COO$— in which $R^5$ is hydrogen, lower alkyl or lower cycloalkyl, $R^6$ is hydrogen or lower alkyl; and $R^7$ is hydrogen, lower alkyl, lower alkenyl or a carboxylic acid protecting group selected from benzhydryl, p-nitrobenzyl and p-methoxybenzyl; or a heterocyclyl which is a 5- or 6-membered ring optionally containing nitrogen, sulfur and/or oxygen having a phenyl ring fused thereto, the heterocyclyl thereof being unsubstituted or substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, or lower alkenyl substituted phenyl; and $R^4$ is hydrogen, hydroxy, lower (cyclo)alkyl, lower alkoxy, lower (cyclo)alkenyl, lower alkynyl, aralkyl, aryl, aryloxy, aralkyloxy, heterocyclyl or heterocyclylalkyl, with each of lower (cyclo)alkyl, lower alkoxy, lower (cyclo)alkenyl, aralkyl, aryl, aryloxy, aralkyloxy or heterocyclyl ring being unsubstituted or substituted by carboxy, amino, nitro, cyano, lower alkyl, benzyl, lower alkoxy, hydroxy, halogen, —CONR$^5$R$^6$, —CH$_2$—CONR$^5$R$^6$, —N(R$^6$)COOR$^7$, R$^6$CO—, R$^6$OCO— or R$^6$COO— in which R$^5$ is hydrogen, lower alkyl ol lower cycloalkyl; R$^6$ is hydrogen or lower alkyl; and R$^7$ is hydrogen, lower alkyl, lower alkenyl or a carboxylic acid protecting group selected from benzhydryl, p-nitrobenzyl and p-methoxybenzyl;

R$^S$ is hydrogen, unsubstituted lower (cyclo)alkyl or lower (cyclo)alkyl substituted by carboxy, lower alkoxycarbonyl, carbamoyl, lower alkylcarbamoyl, phenylcarbamoyl or hydroxyphenylcarbamoyl; lower alkenylmethyl; lower alkenylmethoxycarbonyl; formyl; unsubstituted lower (cyclo)alkanoyl; or lower (cyclo)alkanoyl substituted by halogen, cyano, carbamoyl-lower alkoxy, carbamoyl-lower alkylthio or carbamoyl-lower alkylamino, unsubstituted lower (cyclo)alkylsulphonyl; or lower (cyclo)alkylsulphonyl substituted by halogen, cyano, carbamoyl-lower alkoxy, carbamoyl-lower alkylthio or carbamoyl-lower alkylamino; unsubstituted carbamoyl or carbamoyl substituted by lower (cyclo)alkyl, lower alkoxycarbonyl-lower alkyl, benzyloxy-carbonyl-lower alkyl, carboxy-lower alkyl, hydroxyphenyl or carbamoylphenyl; or a ring structure of the formula

(a1)

or

(a2)

Q is a 5- or 6-membered ring optionally containing nitrogen, sulphur and/or oxygen;

X is a direct bond or a group —CH$_2$—, —CH$_2$CH$_2$—, —CH=CH—, —NH—, —NHCH$_2$—, —CH$_2$NH—, —CH(NH$_2$)—, —CH$_2$CH$_2$NH—, —C(=NOCH$_3$)—, —OCH$_2$— or —SCH$_2$—; or is an amino protecting group; and R$^{S1}$ is a carboxy protecting group selected from benzhydryl, t-butyl, allyl, p-nitrobenzyl and p-methoxybenzyl.

54. A pharmaceutical composition comprising a therapeutically effective amount of a compound of formula I

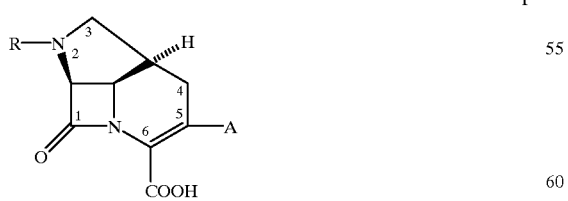

I wherein

R is hydrogen, unsubstituted lower (cyclo)alkyl or lower (cyclo)alkyl substituted by carboxy, lower alkoxycarbonyl, carbamoyl, lower alkylcarbamoyl, phenylcarbamoyl or hydroxyphenylcarbamoyl; lower alkenylmethyl; lower alkenylmethoxycarbonyl; formyl; unsubstituted lower (cyclo)alkanoyl; or lower (cyclo)alkanoyl substituted by halogen, cyano, carbamoyl-lower alkoxy, carbamoyl-lower alkylthio or carbamoyl-lower alkylamino, unsubstituted lower (cyclo)alkylsulphonyl; or lower (cyclo)alkylsulphonyl substituted by halogen, cyano, carbamoyl-lower alkoxy, carbamoyl-lower alkylthio or carbamoyl-lower alkylamino; unsubstituted carbamoyl or carbamoyl substituted by lower (cyclo)alkyl, lower alkoxycarbonyl-lower alkyl, benzyloxy-carbonyl-lower alkyl, carboxy-lower alkyl, hydroxyphenyl or carbamoylphenyl; or a ring structure of the formula

(a1)

or

(a2)

Q is a 5- or 6-membered ring optionally containing nitrogen, sulphur and/or oxygen;

X is a direct bond or a group —CH$_2$—, —CH$_2$CH$_2$—, —CH=CH—, —NH—, —NHCH$_2$—, —CH$_2$NH—, —CH(NH$_2$)—, —CH$_2$CH$_2$NH—, —C(=NOCH$_3$)—, —OCH$_2$— or —SCH$_2$—; and A is a group of formula (b1) or (b2)

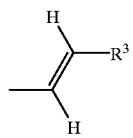

(b1)

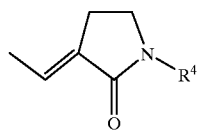

(b2)

wherein

R$^3$ is unsubstituted aryl or aryl substituted by one or two substituents selected from halogen, hydroxy, cyano, nitro, lower alkyl, lower alkoxy, aralkyl, —CONR$^5$R$^6$, —CH$_2$—CONR$^5$R$^6$, —N(R$^6$)COOR$^7$, R$^6$CO—, R$^6$OCO— or R$^6$COO— in which R$^5$ is hydrogen, lower alkyl or lower cycloalkyl; R$^6$ is hydrogen or lower alkyl; and R$^7$ is hydrogen, lower alkyl, lower alkenyl or a carboxylic acid protecting group selected from benzhydryl, p-nitrobenzyl, and p-methoxybenzyl; an unsubstituted heterocyclyl which is a 5- or 6-membered ring optionally containing nitrogen, sulfur and/or oxygen; a heterocyclyl which is a 5- or 6-membered ring optionally containing nitrogen, sulfur and/or oxygen substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, lower alkenyl substituted phenyl, —CONR$^5$R$^6$, —CH$_2$—CONR$^5$R$^6$, —N(R$^6$)COOR$^7$, R$^6$CO—, R$^6$OCO— or R$^6$COO— in which R$^5$ is hydrogen, lower alkyl or lower cycloalkyl; R$^6$ is hydrogen or lower alkyl; and $R^7$ is hydrogen, lower alkyl, lower alkenyl or a carboxylic acid protecting group selected from benzhydryl, p-nitrobenzyl, and p-methoxybenzyl; or a heterocyclyl which is a 5- or 6-membered ring optionally containing nitrogen, sulfur and/or oxygen having a phenyl ring fused thereto, the heterocyclyl thereof being unsubstituted or substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, or lower alkenyl substituted phenyl; and $R^4$ is hydrogen, hydroxy, lower (cyclo)alkyl, lower alkoxy, lower (cyclo)alkenyl, lower alkynyl, aralkyl, aryl, aryloxy, aralkyloxy, heterocyclyl which is a 5- or 6-membered ring optionally containing nitrogen, sulfur and/or oxygen or lower alkyl substituted with a heterocyclyl which is a 5- or 6-membered ring optionally containing nitrogen, sulfur and/or oxygen, with each of lower (cyclo)alkyl, lower alkoxy, lower (cyclo)alkenyl, aralkyl, aryl, aryloxy, aralkyloxy or heterocyclyl ring which is a 5- or 6-membered ring optionally containing nitrogen, sulfur and/or oxygen being unsubstituted or substituted by carboxy, amino, nitro, cyano, lower alkyl, benzyl, lower alkoxy, hydroxy, halogen, —$CONR^5R^6$, —$CH_2$—$CONR^5R^6$, —$N(R^6)COOR^7$, $R^6CO$—, $R^6OCO$— or $R^6COO$— in which $R^5$ is hydrogen, lower alkyl or lower cycloalkyl; $R^6$ is hydrogen or lower alkyl; and $R^7$ is hydrogen, lower alkyl, lower alkenyl or a carboxylic acid protecting group selected from benzhydryl, p-nitrobenzyl, and p-methoxybenzyl; and pharmaceutically compatible, readily hydrolyzable esters thereof selected from lower alkanoyloxyalkyl esters, lower alkoxycarbonyloxyalkyl esters, 1-cyclohexyloxycarbonyloxyethyl ester, (5-methyl-2-oxo-1,3-dioxol-4-yl)-methyl ester, phthalidyl esters, thiophthalidyl esters, lower alkoxymethyl esters, lower alkanoylaminomethyl esters, benzyl esters, cyanomethyl esters, (2,2-dimethyl-1-oxopropoxy)methyl ester, [2-[(2-mehtylpropoxy)carbonyl]-2-pentenyl] 2-(2-methylpropoxy) carbonyl-2-pentenyl ester, 1-[[(1-methylethoxy)carbonyl]oxy]ethyl ester and 3-3-dimethyl-2-oxobutyl ester, and salts of these compounds and a pharmaceutically acceptable carrier.

55. A method of treating bacterial infections in a mammal in need of such treatment which comprises administering a therapeutically effective amount of a compound of formula I

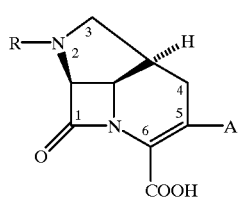

I wherein

R is hydrogen, unsubstituted lower (cyclo)alkyl or lower (cyclo)alkyl substituted by carboxy, lower alkoxycarbonyl, carbamoyl, lower alkylcarbamoyl, phenylcarbamoyl or hydroxyphenylcarbamoyl; lower alkenylmethyl; lower alkenylmethoxycarbonyl; formyl; unsubstituted lower (cyclo)alkanoyl; or lower (cyclo)alkanoyl substituted by halogen, cyano, carbamoyl-lower alkoxy, carbamoyl-lower alkylthio or carbamoyl-lower alkylamino, unsubstituted lower (cyclo)alkylsulphonyl; or lower (cyclo)alkylsulphonyl substituted by halogen, cyano, carbamoyl-lower alkoxy, carbamoyl-lower alkylthio or carbamoyl-lower alkylamino; unsubstituted carbamoyl or carbamoyl substituted by lower (cyclo)alkyl, lower alkoxycarbonyl-lower alkyl, benzyloxy-carbonyl-lower alkyl, carboxy-lower alkyl, hydroxyphenyl or carbamoylphenyl; or a ring structure of the formula

 (a1)

or

 (a2)

Q is a 5- or 6-membered ring optionally containing nitrogen, sulphur and/or oxygen;

X is a direct bond or a group —$CH_2$—, —$CH_2CH_2$—, —CH=CH—, —NH—, —$NHCH_2$—, —$CH_2NH$—, —$CH(NH_2)$—, —$CH_2CH_2NH$—, —C(=NOCH3)—, —$OCH_2$— or —$SCH_2$—; and A is a group of formula (b1) or (b2)

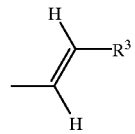 (b1)

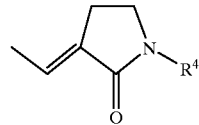 (b2)

wherein $R^3$ is unsubstituted aryl or aryl substituted by one or two substituents selected from halogen, hydroxy, cyano, nitro, lower alkyl, lower alkoxy, aralkyl, —$CONR^5R^6$, —$CH_2$—$CONR^5R^6$, —$N(R^6)COOR^7$, $R^6CO$—, $R^6OCO$— or $R^6COO$— in which $R^5$ is hydrogen, lower alkyl or lower cycloalkyl; $R^6$ is hydrogen or lower alkyl; and $R^7$ is hydrogen, lower alkyl, lower alkenyl or a carboxylic acid protecting group selected from benzhydryl, p-nitrobenzyl, and p-methoxybenzyl; an unsubstituted heterocyclyl which is a 5- or 6-membered ring optionally containing nitrogen, sulfur and/or oxygen; a heterocyclyl which is a 5- or 6-membered ring optionally containing nitrogen, sulfur and/or oxygen substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, lower alkenyl substituted phenyl, —$CONR^5R^6$, —$CH_2$—$CONR^5R^6$, —$N(R^6)COOR^7$, R⁶CO—, R⁶OCO— or R⁶COO— in which R⁵ is hydrogen, lower alkyl or lower cycloalkyl; R⁶ is hydrogen or lower alkyl; and R⁷ is hydrogen, lower alkyl, lower alkenyl or a carboxylic acid protecting group selected from benzhydryl, p-nitrobenzyl, and p-methoxybenzyl; or a heterocyclyl which is a 5- or 6-membered ring optionally containing nitrogen, sulfur and/or oxygen having a phenyl ring fused thereto, the heterocyclyl thereof being unsubstituted or substituted by lower alkyl, lower alkoxy, halogen, halo substituted alkyl, amino, mercapto, hydroxyl, carbamoyl, carboxyl, oxo, lower alkylthio, carbamoylmethyl, carbamoylamino, hydroxyphenylcarbamoyl, lower alkanoyloxy, methylamino, dimethylamino, chloroacetylamino, unsubstituted benzyl, lower alkoxy substituted benzyl, halo lower alkoxy substituted benzyl, or lower alkenyl substituted phenyl; and R⁴ is hydrogen, hydroxy, lower (cyclo)alkyl, lower alkoxy, lower (cyclo)alkenyl, lower alkynyl, aralkyl, aryl, aryloxy, aralkyloxy, heterocyclyl which is a 5- or 6-membered ring optionally containing nitrogen, sulfur and/or oxygen or lower alkyl substituted with a heterocyclyl which is a 5- or 6-membered ring optionally containing nitrogen, sulfur and/or oxygen, with each of lower (cyclo)alkyl, lower alkoxy, lower (cyclo)alkenyl, aralkyl, aryl, aryloxy, aralkyloxy or heterocyclyl ring which is a 5- or 6-membered ring optionally containing nitrogen, sulfur and/or oxygen being unsubstituted or substituted by carboxy, amino, nitro, cyano, lower alkyl, benzyl, lower alkoxy, hydroxy, halogen, —CONR⁵R⁶, —CH₂—CONR⁵R⁶, —N(R⁶)COOR⁷, R⁶CO—, R⁶OCO— or R⁶COO— in which R⁵ is hydrogen, lower alkyl or lower cycloalkyl; R⁶ is hydrogen or lower alkyl; and R⁷ is hydrogen, lower alkyl, lower alkenyl or a carboxylic acid protecting group selected from benzhydryl, p-nitrobenzyl, and p-methoxybenzyl; and pharmaceutically compatible, readily hydrolyzable esters thereof selected from lower alkanoyloxyalkyl esters, lower alkoxycarbonyloxyalkyl esters, 1-cyclohexyloxycarbonyloxyethyl ester, (5-methyl-2-oxo-1,3-dioxol-4-yl)-methyl ester, phthalidyl esters, thiophthalidyl esters, lower alkoxymethyl esters, lower alkanoylaminomethyl esters, benzyl esters, cyanomethyl esters, (2,2-dimethyl-1-oxopropoxyl)methyl ester, [2-[(2-mehtylpropoxy)carbonyl]-2-pentenyl] 2-[(2-methylpropoxy)carbonyl]-2-pentenyl ester, 1-[[(1-methylethoxy)carbonyl]oxy]ethyl ester and 3-3-dimethyl-2-oxobutyl ester, and salts of these compounds and a pharmaceutically acceptable carrier.

56. The compound of claim 27, wherein A is formula (b2).

57. The compound of claim 34, wherein the heterocyclyl of the heterocyclyl having a phenyl ring fused thereto is substituted by carbamoylmethyl.

58. The compound of claim 56, wherein R⁴ is selected from unsubstituted lower alkyl, lower alkyl substituted by halogen, lower cycloalkyl, unsubstituted aryl, aryl substituted by hydroxy or nitro, unsubstituted aralkyl or aralkyl substituted by nitro, heterocyclylalkyl, unsubstituted heterocyclyl, heterocyclyl substituted by benzyl, R⁶OCO— or —CH₂—CONR⁵R⁶ where R⁵ is hydrogen or lower alkyl and R⁶ is hydrogen or lower alkyl.

59. The compound of claim 3, wherein R is lower alkanoyl substituted by halogen.

60. The compound of claim 59, wherein A is formula (b1).

61. The compound of claim 60, wherein R³ is unsubstituted heterocyclyl.

62. The compound of claim 61, (E)-(1aS,3aR,6bR)-1-oxo-5-(2-pyridin-2-yl-vinyl)-2-trifluoroacetyl-1a,2,3,3a,4,6b-hexahydro-1H-2,6a-diaza-cyclobut[cd]indene-6-carboxylic acid.

63. The compound of claim 4, wherein A is formula (b2).

64. The compound of claim 63, wherein R⁴ is selected from unsubstituted lower alkyl, lower alkyl substituted by halogen, lower cycloalkyl, unsubstituted aryl, aryl substituted by hydroxy or nitro, unsubstituted aralkyl or aralkyl substituted by nitro, heterocyclylalkyl, unsubstituted heterocyclyl, heterocyclyl substituted by benzyl, R⁶OCO— or —CH₂—CONR⁵R⁶ where R⁵ is hydrogen or lower alkyl and R⁶ is hydrogen or lower alkyl.

65. The compound of claim 64, wherein R⁴ is aryl substituted by hydroxy.

66. The compound of claim 65, (E)-(1aS,3aR,6bR)-1-Oxo-5-[2-oxo-1-(4-hydroxyphenyl)-pyrrolidin-3-ylidenemethyl]-1a,2,3,3a,4,6b-hexahydro-1H-2,6a-diaza-cyclobut[cd]indene-6-carboxylic acid.

67. The compound of claim 64, wherein R⁴ is aryl substituted by nitro.

68. The compound of claim 67, (E)-(1aS,3aR,6bR)-1-oxo-5-[1-(3-nitrophenyl)-2-oxo-pyrrolidin-3-ylidenemethyl]-1a,2,3,3a,4,6b-hexahydro-1H-2,6a-diaza-cyclobut[cd]indene-6-carboxylic acid.

69. The compound of claim 64, wherein R⁴ is unsubstituted aryl.

70. The compound of claim 69, (E)-(1aS,3aR,6bR)-1-oxo-5-[2-oxo-1-phenyl-pyrrolidin-3-ylidenemethyl]-1a,2,3,3a,4,6b-hexahydro-1H-2,6a-diaza-cyclobut[cd]indene-6-carboxylic acid.

71. The compound of claim 64, wherein R⁴ is selected from unsubstituted lower alkyl.

72. The compound of claim 71, (E)-(1aS,3aR,6bR)-1-oxo-5-[1-(isobutyl)-2-oxo-pyrrolidin-3-ylidenemethyl]-1a,2,3,3a,4,6b-hexahydro-1H-2,6a-diaza-cyclobut[cd]indene-6-carboxylic acid.

73. The compound of claim 64, wherein R⁴ is selected from lower alkyl substituted by halogen.

74. The compound of claim 73, (E)-(1aS,3aR,6bR)-1-oxo-5-[2-oxo-1-(2,2,2-trifluoro-ethyl)-pyrrolidin-3-ylidenemethyl]-1a,2,3,3a,4,6b-hexahydro-1H-2,6a-diaza-cyclobut[cd]indene-6-carboxylic acid.

75. The compound of claim 64, wherein R⁴ is lower cycloalkyl.

76. The compound of claim 75, (E)-(1aS,3aR,6bR)-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-6-carboxylic acid.

77. The compound of claim 64, wherein R⁴ is aralkyl substituted by nitro.

78. The compound of claim 77, (E)-(1aS,3aR,6bR)-1-oxo-5-2-oxo-1-(4-nitrobenzyl)-pyrrolidin-3-ylidenemethyl]-1a,2,3,3a,4,6b-hexahydro-1H-2,6a-diaza-cyclobut[cd]indene-6-carboxylic acid.

79. The compound of claim 64, wherein R⁴ is unsubstituted heterocyclyl.

80. The compound of claim 79, (E)-(1aS,3aR,6bR)-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-6-carboxylic acid.

81. The compound of claim 64, wherein R⁴ is heterocyclyl substituted by benzyl, R⁶OCO— or —CH₂—CONR⁵R⁶ where R⁵ is hydrogen or lower alkyl and R⁶ is hydrogen or lower alkyl, or heterocyclylalkyl.

82. The compound of claim 81, wherein the heterocyclyl is substituted by $R^6OCO$— where $R^6$ is hydrogen or lower alkyl.

83. The compound of claim 82, wherein $R^6$ is lower alkyl.

84. The compound of claim 83, (E)-(1aS,3aR,6bR)-1-oxo-5-[1-(1-ethoxycarbonyl-piperidin-4-yl)-2-oxo-pyrrolidin-3-ylidenemethyl]-1a,2,3,3a,4, 6b-hexahydro-1H-2,6a-diaza-cyclobut[cd]indene-6-carboxylic acid.

85. The compound of claim 64, wherein $R^4$ is heterocyclylalkyl.

86. The compound of claim 85, (E)-(1aS,3aR,6bR)-1-oxo-5-[2-oxo-1-(thiophen-2-ylmethyl)-pyrrolidin-3-ylidenemethyl]-1a,2,3,3a,4,6b-hexahydro-1H-2,6a-diaza-cyclobut[cd]indene-6-carboxylic acid.

87. The compound of claim 59, wherein A is formula (b2).

88. The compound of claim 87, wherein $R^4$ is selected from unsubstituted lower alkyl, lower alkyl substituted by halogen, lower cycloalkyl, unsubstituted aryl, aryl substituted by hydroxy or nitro, unsubstituted aralkyl or aralkyl substituted by nitro, heterocyclylalkyl, unsubstituted heterocyclyl, heterocyclyl substituted by benzyl, $R^6OCO$— or —$CH_2$—$CONR^5R^6$ where $R^5$ is hydrogen or lower alkyl and $R^6$ is hydrogen or lower alkyl.

89. The compound of claim 58, wherein $R^4$ is aryl substituted by hydroxy.

90. The compound of claim 89, (E)-(1aS,3aR,6bR)-2-acetyl-1-oxo-5-[2-oxo-1-(4-hydroxyphenyl)-pyrrolidin-3-ylidenemethyl]-1a,2,3,3a,4,6b-hexahydro-1H-2,6a-diaza-cyclobut[cd]indene-6-carboxylic acid.

91. The compound of claim 88, wherein $R^4$ is aryl substituted by nitro.

92. The compound of claim 91, (E)-(1aS,3aR,6bR)-2-acetyl-1-oxo-5-[1-(3-nitrophenyl)-2-oxo-pyrrolidin-3-ylidenemethyl]-1a,2,3,3a,4,6b-hexahydro-1H-2,6a-diaza-cyclobut[cd]indene-6-carboxylic acid.

93. The compound of claim 88, wherein $R^4$ is unsubstituted aryl.

94. The compound of claim 93, (E)-(1aS,3aR,6bR)-2-acetyl-1-oxo-5-[2-oxo-1-phenyl-pyrrolidin-3-ylidenemethyl]-1a,2,3,3a,4,6b-hexahydro-1H-2,6a-diaza-cyclobut[cd]indene-6-carboxylic acid.

95. The compound of claim 88, wherein $R^4$ is selected from unsubstituted lower alkyl.

96. The compound of claim 95, (E)-(1aS,3aR,6bR)-2-acetyl-1-oxo-5-[2-oxo-1-isobutyl-pyrrolidin-3-ylidenemethyl]-1a,2,3,3a,4,6b-hexahydro-1H-2,6a-diaza-cyclobut[cd]indene-6-carboxylic acid.

97. The compound of claim 88, wherein $R^4$ is selected from lower alkyl substituted by halogen.

98. The compound of claim 97, (E)-(1aS,3aR,6bR)-2-acetyl-1-oxo-5-[2-oxo-1-(2,2,2-trifluoroethyl)-pyrrolidin-3-ylidenemethyl]-1a,2,3,3a,4,6b-hexahydro-1H-2,6a-diaza-cyclobut[cd]indene-6-carboxylic acid.

99. The compound of claim 88, wherein $R^4$ is lower cycloalkyl.

100. The compound of claim 99, (E)-(1aS,3aR,6bR)-2-acetyl-1-oxo-5-[1-cyclopropyl-2-oxo-pyrrolidin-3-ylidenemethyl]-1a,2,3,3a,4,6b-hexahydro-1H-2,6a-diaza-cyclobut[cd]indene-6-carboxylic acid.

101. The compound of claim 88, wherein $R^4$ is aralkyl substituted by nitro.

102. The compound of claim 101, (E)-(1aS,3aR,6bR)-2-acetyl-1-oxo-5-[2-oxo-1-(4-nitrobenzyl)-pyrrolidin-3-ylidenemethyl]-1a,2,3,3a,4,6b-hexahydro-1H-2,6a-diaza-cyclobut[cd]indene-6-carboxylic acid.

103. The compound of claim 88, wherein $R^4$ is unsubstituted heterocyclyl.

104. The compound of claim 103, (E)-(1aS,3aR,6bR)-2-acetyl-1-oxo-5-[2-oxo-1-pyridin-3-yl-pyrrolidin-3-ylidenemethyl]-1a,2,3,3a,4,6b-hexahydro-1H-2,6a-diaza-cyclobut[cd]indene-6-carboxylic acid.

105. The compound of claim 88, wherein $R^4$ is heterocyclyl substituted by benzyl, $R^6OCO$— or —$CH_2$—$CONR^5R^6$ where $R^5$ is hydrogen or lower alkyl and $R^6$ is hydrogen or lower alkyl, or heterocyclylalkyl.

106. The compound of claim 105, wherein the heterocyclyl is substituted by $R^6OCO$— where $R^6$ is hydrogen or lower alkyl.

107. The compound of claim 106, wherein $R^6$ is lower alkyl.

108. The compound of claim 107, (E)-(1aS,3aR,6bR)-2-acetyl-1-oxo-5-[1-(1-ethoxycarbonyl-piperidin-4-yl)-2-oxo-pyrrolidin-3-ylidenemethyl]-1a,2,3,3a,4, 6b-hexahydro-1H-2,6a-diaza-cyclobut[cd]indene-6-carboxylic acid.

109. The compound of claim 88, wherein $R^4$ is heterocyclylalkyl.

110. The compound of claim 109, (E)-(1aS,3aR,6bR)-2-acetyl-1-oxo-5-[2-oxo-1-(thiophen-2-yl-methyl)-pyrrolidin-3-ylidenemethyl]-1a,2,3,3a,4,6b-hexahydro-1H-2,6a-diaza-cyclobut[cd]indene-6-carboxylic acid.

111. The compound of claim 88, wherein $R^4$ is heterocyclylalkyl.

112. The compound of claim 111, (E)-(1aS,3aR,6bR)-1-oxo-5-[2-oxo-1-(thiophen-2-yl-methyl)-pyrrolidin-3-ylidenemethyl]-2-trifluoroacetyl-1a,2,3,3a,4,6b-hexahydro-1H-2,6a-diaza-cyclobut[cd]indene-6-carboxylic acid.

113. The compound of claim 88, wherein $R^4$ is aryl substituted by nitro.

114. The compound of claim 113, (E)-(1aS,3aR,6bR)-1-oxo-5-[2-oxo-1-(3-nitro-phenyl)-pyrrolidin-3-ylidenemethyl]-2-trifluoro-acetyl-1a,2,3,3a,4,6b-hexahydro-1H-2,6a-diaza-cyclobut[cd]indene-6-carboxylic acid.

115. The compound of claim 88, wherein $R^4$ is unsubstituted aryl.

116. The compound of claim 115, (E)-(1aS,3aR,6bR)-1-oxo-5-[2-oxo-1-phenyl-pyrrolidin-3-ylidenemethyl]-2-trifluoroacetyl-1a,2,3,3a,4,6b-hexahydro-1H-2,6a-diaza-cyclobut[cd]indene-6-carboxylic acid.

117. The compound of claim 88, wherein $R^4$ is lower cycloalkyl.

118. The compound of claim 117, (E)-(1aS,3aR,6bR)-1-oxo-5-[2-oxo-1-cyclopropyl-pyrrolidin-3-ylidenemethyl]-2-trifluoro-acetyl-1a,2,3,3a,4,6b-hexahydro-1H-2,6a-diaza-cyclobut[cd]indene-6-carboxylic acid.

119. The compound of claim 88, wherein $R^4$ is unsubstituted heterocyclyl.

120. The compound of claim 119, (E)-(1aS,3aR,6bR)-1-oxo-5-[2-oxo-1-pyridin-3-yl-pyrrolidin-3-ylidenemethyl]-2-trifluoro-acetyl-1a,2,3,3a,4,6b-hexahydro-1H-2,6a-diaza-cyclobut[cd]indene-6-carboxylic acid.

121. The compound of claim 88, wherein $R^4$ is heterocyclyl substituted by benzyl, $R^6OCO$— or —$CH_2$—$CONR^5R^6$ where $R^5$ is hydrogen or lower alkyl and $R^6$ is hydrogen or lower alkyl.

122. The compound of claim 121, wherein the heterocyclyl is substituted by —$CH_2$—$CONR^5R^6$ where $R^5$ is hydrogen or lower alkyl and $R^6$ is hydrogen or lower alkyl.

123. The compound of claim 121, wherein the heterocyclyl is substituted by benzyl.

124. The compound of claim 122, wherein $R^6$ is hydrogen and $R^5$ is hydrogen.

* * * * *

UNITED STATES PATENT AND TRADEMARK OFFICE
CERTIFICATE OF CORRECTION

PATENT NO. : 6,218,379 B1
DATED : April 17, 2001
INVENTOR(S) : Böhringer et al.

It is certified that error appears in the above-identified patent and that said Letters Patent is hereby corrected as shown below:

<u>Column 61, claim 1,</u>
Lines 41-42, delete "[2-[(2-mehtylpropoxy) carbonyl]".

Signed and Sealed this

Twenty-sixth Day of March, 2002

Attest:

*Attesting Officer*

JAMES E. ROGAN
*Director of the United States Patent and Trademark Office*